(12) United States Patent
Hammond et al.

(10) Patent No.: US 10,702,420 B2
(45) Date of Patent: Jul. 7, 2020

(54) WOUND CLOSURE DEVICE

(71) Applicant: Smith & Nephew PLC, Watford, Hertfordshire (GB)

(72) Inventors: Victoria Jody Hammond, Hull (GB); Edward Yerbury Hartwell, Hull (GB); John Kenneth Hicks, York (GB); Carl Saxby, Brough (GB)

(73) Assignee: Smith & Nephew PLC, Watford (GB)

( * ) Notice: Subject to any disclaimer, the term of this patent is extended or adjusted under 35 U.S.C. 154(b) by 344 days.

(21) Appl. No.: 15/837,948

(22) Filed: Dec. 11, 2017

(65) Prior Publication Data

US 2018/0161212 A1 Jun. 14, 2018

Related U.S. Application Data

(63) Continuation of application No. 14/402,674, filed as application No. PCT/IB2013/002485 on May 21, 2013, now Pat. No. 9,844,472.

(Continued)

(51) Int. Cl.
*A61F 13/00* (2006.01)
*A61M 1/00* (2006.01)
(Continued)

(52) U.S. Cl.
CPC ...... *A61F 13/00068* (2013.01); *A61F 15/008* (2013.01); *A61M 1/0088* (2013.01); *A61B 17/085* (2013.01)

(58) Field of Classification Search
CPC ................ A61M 1/0088; A61F 15/008; A61F 13/00068; A61B 17/085
See application file for complete search history.

(56) References Cited

U.S. PATENT DOCUMENTS 3,014,483 A * 12/1961 McCarthy .......... A61B 17/0466
606/233
3,194,239 A 7/1965 Sullivan
(Continued)

FOREIGN PATENT DOCUMENTS

AU 2012261793 B2 11/2014
AU 2013206230 B2 5/2016
(Continued)

OTHER PUBLICATIONS

Definition of "Adhere", The Free Dictionary, accessed Mar. 23, 2017, in 6 pages. URL: http://www.thefreedictionary.com/adhere.
(Continued)

*Primary Examiner* — Adam Marcetich
(74) *Attorney, Agent, or Firm* — Knobbe, Martens, Olson & Bear, LLP

(57) ABSTRACT

A wound dressing for use in the application of negative pressure to a wound, comprising a support member and a cover member positionable over the wound in use. The support member can have a first support element having a first portion aligned with a first axis and a body portion coupled with and extending away from the first portion, and a second support element having a first portion aligned with the first axis and a body portion coupled with and extending away from the first portion of the second support element. At least the body portion of each of the first support element and the second support element can be independently rotatable about the first axis. The support member can support at least a middle portion of the cover member above a surface of the wound so as to define a space between the wound cover and the wound.

17 Claims, 31 Drawing Sheets

Related U.S. Application Data

(60) Provisional application No. 61/784,304, filed on Mar. 14, 2013, provisional application No. 61/681,037, filed on Aug. 8, 2012, provisional application No. 61/651,483, filed on May 24, 2012, provisional application No. 61/650,391, filed on May 22, 2012.

(51) Int. Cl.
*A61F 15/00* (2006.01)
*A61B 17/08* (2006.01)

(56) References Cited

U.S. PATENT DOCUMENTS

| | | | |
|---|---|---|---|
| 3,578,003 A * | 5/1971 | Everett | E04H 15/006 135/137 |
| 3,789,851 A | 2/1974 | LeVeen | |
| 3,812,616 A * | 5/1974 | Koziol | A01G 13/0231 52/63 |
| 4,467,805 A | 8/1984 | Fukuda | |
| 4,608,041 A | 8/1986 | Nielsen | |
| 4,699,134 A | 10/1987 | Samuelsen | |
| 4,815,468 A | 3/1989 | Annand | |
| 5,176,663 A | 1/1993 | Svedman et al. | |
| 5,264,218 A | 11/1993 | Rogozinski | |
| 5,376,067 A | 12/1994 | Daneshvar | |
| 5,409,472 A | 4/1995 | Rawlings et al. | |
| 5,415,715 A | 5/1995 | Delage et al. | |
| 5,423,857 A | 6/1995 | Rosenman et al. | |
| 5,512,041 A | 4/1996 | Bogart | |
| 5,562,107 A | 10/1996 | Lavendar et al. | |
| 5,584,859 A | 12/1996 | Brotz | |
| 5,636,643 A | 6/1997 | Argenta et al. | |
| 5,695,777 A | 12/1997 | Donovan et al. | |
| 5,960,497 A | 10/1999 | Castellino et al. | |
| 6,080,168 A | 6/2000 | Levin et al. | |
| 6,086,591 A | 7/2000 | Bojarski | |
| 6,142,982 A | 11/2000 | Hunt et al. | |
| 6,176,868 B1 | 1/2001 | Detour | |
| 6,503,208 B1 | 1/2003 | Skovlund | |
| 6,530,941 B1 * | 3/2003 | Muller | A61F 5/05833 606/201 |
| 6,548,727 B1 | 4/2003 | Swenson | |
| 6,553,998 B2 | 4/2003 | Heaton et al. | |
| 6,566,575 B1 | 5/2003 | Stickels et al. | |
| 6,685,681 B2 | 2/2004 | Lockwood et al. | |
| 6,695,823 B1 | 2/2004 | Lina et al. | |
| 6,712,830 B2 | 3/2004 | Esplin | |
| 6,712,839 B1 * | 3/2004 | Lonne | A61B 17/085 606/233 |
| 6,767,334 B1 | 7/2004 | Randolph | |
| 6,770,794 B2 | 8/2004 | Fleischmann | |
| 6,776,769 B2 | 8/2004 | Smith | |
| 6,787,682 B2 | 9/2004 | Gilman | |
| 6,814,079 B2 | 11/2004 | Heaton et al. | |
| 6,883,531 B1 * | 4/2005 | Perttu | E04H 15/001 135/115 |
| 6,893,452 B2 | 5/2005 | Jacobs | |
| 6,936,037 B2 | 8/2005 | Bubb et al. | |
| 6,951,553 B2 | 10/2005 | Bubb et al. | |
| 6,977,323 B1 | 12/2005 | Swenson | |
| 6,994,702 B1 | 2/2006 | Johnson | |
| 7,004,915 B2 | 2/2006 | Boynton et al. | |
| 7,025,755 B2 | 4/2006 | Epstein | |
| 7,070,584 B2 | 7/2006 | Johnson et al. | |
| 7,117,869 B2 | 10/2006 | Heaton et al. | |
| 7,128,735 B2 | 10/2006 | Weston | |
| 7,144,390 B1 | 12/2006 | Hannigan et al. | |
| 7,153,312 B1 | 12/2006 | Torrie et al. | |
| 7,156,862 B2 | 1/2007 | Jacobs et al. | |
| 7,172,615 B2 | 2/2007 | Morriss et al. | |
| 7,189,238 B2 | 3/2007 | Lombardo et al. | |
| 7,196,054 B1 | 3/2007 | Drohan et al. | |
| 7,198,046 B1 | 4/2007 | Argenta et al. | |
| 7,216,651 B2 | 5/2007 | Argenta et al. | |
| D544,092 S | 6/2007 | Lewis | |
| 7,262,174 B2 | 8/2007 | Jiang et al. | |
| 7,279,612 B1 | 10/2007 | Heaton et al. | |
| 7,315,183 B2 | 1/2008 | Hinterscher | |
| 7,351,250 B2 | 4/2008 | Zamierowski | |
| 7,361,184 B2 | 4/2008 | Joshi | |
| 7,367,342 B2 | 5/2008 | Butler | |
| 7,381,211 B2 | 6/2008 | Zamierowski | |
| 7,381,859 B2 | 6/2008 | Hunt et al. | |
| 7,413,571 B2 | 8/2008 | Zamierowski | |
| 7,438,705 B2 | 10/2008 | Karpowicz et al. | |
| 7,494,482 B2 | 2/2009 | Orgill et al. | |
| 7,534,240 B1 | 5/2009 | Johnson | |
| 7,540,848 B2 | 6/2009 | Hannigan et al. | |
| 7,553,306 B1 | 6/2009 | Hunt et al. | |
| 7,553,923 B2 | 6/2009 | Williams et al. | |
| 7,569,742 B2 | 8/2009 | Haggstrom et al. | |
| 7,578,532 B2 | 8/2009 | Schiebler | |
| D602,583 S | 10/2009 | Pidgeon et al. | |
| 7,611,500 B1 | 11/2009 | Lina et al. | |
| 7,615,036 B2 | 11/2009 | Joshi et al. | |
| 7,617,762 B1 * | 11/2009 | Ragner | F16J 3/06 92/37 |
| 7,618,382 B2 | 11/2009 | Vogel et al. | |
| 7,622,629 B2 | 11/2009 | Aali | |
| 7,625,362 B2 | 12/2009 | Boehringer et al. | |
| 7,645,269 B2 | 1/2010 | Zamierowski | |
| 7,651,484 B2 | 1/2010 | Heaton et al. | |
| 7,670,323 B2 | 3/2010 | Hunt et al. | |
| 7,678,102 B1 | 3/2010 | Heaton | |
| 7,683,667 B2 | 3/2010 | Kim | |
| 7,699,823 B2 | 4/2010 | Haggstrom et al. | |
| 7,699,830 B2 | 4/2010 | Martin | |
| 7,699,831 B2 | 4/2010 | Bengtson et al. | |
| 7,700,819 B2 | 4/2010 | Ambrosio et al. | |
| 7,708,724 B2 | 5/2010 | Weston | |
| 7,713,743 B2 | 5/2010 | Villanueva et al. | |
| 7,722,528 B2 | 5/2010 | Arnal et al. | |
| 7,723,560 B2 | 5/2010 | Lockwood et al. | |
| 7,754,937 B2 | 7/2010 | Boehringer et al. | |
| 7,776,028 B2 | 8/2010 | Miller et al. | |
| 7,777,522 B2 | 8/2010 | Yang | |
| 7,779,625 B2 | 8/2010 | Joshi et al. | |
| D625,801 S | 10/2010 | Pidgeon et al. | |
| 7,815,616 B2 | 10/2010 | Boehringer et al. | |
| 7,820,453 B2 | 10/2010 | Heylen et al. | |
| 7,846,141 B2 | 12/2010 | Weston | |
| 7,857,806 B2 | 12/2010 | Karpowicz et al. | |
| 7,863,495 B2 | 1/2011 | Aali | |
| 7,892,181 B2 | 2/2011 | Christensen et al. | |
| 7,896,856 B2 | 3/2011 | Petrosenko et al. | |
| 7,909,805 B2 | 3/2011 | Weston | |
| 7,910,789 B2 | 3/2011 | Sinyagin | |
| 7,931,774 B2 | 4/2011 | Hall et al. | |
| 7,942,866 B2 | 5/2011 | Radl et al. | |
| 7,951,124 B2 | 5/2011 | Boehringer et al. | |
| 7,964,766 B2 | 6/2011 | Blott et al. | |
| 7,976,519 B2 | 7/2011 | Bubb et al. | |
| 7,976,524 B2 | 7/2011 | Kudo et al. | |
| 7,981,098 B2 | 7/2011 | Boehringer et al. | |
| 8,030,534 B2 | 10/2011 | Radl et al. | |
| 8,057,447 B2 | 11/2011 | Olson et al. | |
| 8,062,272 B2 | 11/2011 | Weston | |
| 8,062,295 B2 | 11/2011 | McDevitt et al. | |
| 8,062,331 B2 | 11/2011 | Zamierowski | |
| 8,067,662 B2 | 11/2011 | Aali et al. | |
| 8,070,773 B2 | 12/2011 | Zamierowski | |
| 8,080,702 B2 | 12/2011 | Blott et al. | |
| 8,100,887 B2 | 1/2012 | Weston et al. | |
| 8,114,126 B2 | 2/2012 | Heaton et al. | |
| 8,123,781 B2 | 2/2012 | Zamierowski | |
| 8,128,615 B2 | 3/2012 | Blott et al. | |
| 8,129,580 B2 | 3/2012 | Wilkes et al. | |
| 8,142,419 B2 | 3/2012 | Heaton et al. | |
| 8,162,909 B2 | 4/2012 | Blott et al. | |
| 8,172,816 B2 | 5/2012 | Kazala, Jr. et al. | |
| 8,182,413 B2 | 5/2012 | Browning | |
| 8,187,237 B2 | 5/2012 | Seegert | |
| 8,188,331 B2 | 5/2012 | Barta et al. | |

(56) References Cited

U.S. PATENT DOCUMENTS

| | | |
|---|---|---|
| 8,192,409 B2 | 6/2012 | Hardman et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,246,590 B2 | 8/2012 | Hu et al. |
| 8,246,606 B2 | 8/2012 | Stevenson et al. |
| 8,257,328 B2 | 9/2012 | Augustine et al. |
| 8,273,105 B2 | 9/2012 | Cohen et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,376,972 B2 | 2/2013 | Fleischmann |
| 8,399,730 B2 | 3/2013 | Kazala, Jr. et al. |
| 8,430,867 B2 | 4/2013 | Robinson et al. |
| 8,444,392 B2 | 5/2013 | Turner et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,535,296 B2 | 9/2013 | Blott et al. |
| 8,608,776 B2 | 12/2013 | Coward et al. |
| 8,622,981 B2 | 1/2014 | Hartwell et al. |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,721,629 B2 | 5/2014 | Hardman et al. |
| 8,746,662 B2 | 6/2014 | Poppe |
| 8,747,375 B2 | 6/2014 | Barta et al. |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,821,535 B2 | 9/2014 | Greener |
| 8,843,327 B2 | 9/2014 | Vernon-Harcourt et al. |
| 8,945,030 B2 | 2/2015 | Weston |
| 9,044,579 B2 | 6/2015 | Blott et al. |
| 9,050,398 B2 | 6/2015 | Armstrong et al. |
| 9,061,095 B2 | 6/2015 | Adie et al. |
| 9,180,231 B2 | 11/2015 | Greener |
| 9,204,801 B2 | 12/2015 | Locke et al. |
| 9,220,822 B2 | 12/2015 | Hartwell |
| 9,339,248 B2 | 5/2016 | Tout et al. |
| 9,408,755 B2 | 8/2016 | Larsson et al. |
| 9,421,132 B2 | 8/2016 | Dunn |
| 9,655,807 B2 | 5/2017 | Locke et al. |
| 9,757,500 B2 | 9/2017 | Locke et al. |
| 9,844,472 B2 | 12/2017 | Hammond et al. |
| 9,849,023 B2 | 12/2017 | Hall et al. |
| 10,117,782 B2 | 11/2018 | Dagger et al. |
| 10,537,657 B2 | 1/2020 | Phillips et al. |
| 2001/0029956 A1 | 10/2001 | Argenta |
| 2001/0034499 A1 | 10/2001 | Sessions et al. |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0220660 A1 | 11/2003 | Kortenbach et al. |
| 2004/0010275 A1 | 1/2004 | Jacobs et al. |
| 2004/0054346 A1 | 3/2004 | Zhu et al. |
| 2004/0064132 A1 | 4/2004 | Boehringer et al. |
| 2004/0162512 A1 | 8/2004 | Liedtke et al. |
| 2004/0267312 A1 | 12/2004 | Kanner et al. |
| 2005/0119694 A1 | 6/2005 | Jacobs et al. |
| 2005/0142331 A1 | 6/2005 | Anderson et al. |
| 2005/0182445 A1 | 8/2005 | Zamierowski |
| 2005/0222613 A1 | 10/2005 | Ryan |
| 2005/0258887 A1 | 11/2005 | Ito et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur |
| 2006/0135921 A1 | 6/2006 | Wiercinski et al. |
| 2006/0155260 A1 | 7/2006 | Blott et al. |
| 2006/0213527 A1 | 9/2006 | Argenta et al. |
| 2006/0217795 A1 | 9/2006 | Besselink et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0032755 A1 | 2/2007 | Walsh |
| 2007/0052144 A1 | 3/2007 | Knirck et al. |
| 2007/0104941 A1 | 5/2007 | Kameda et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0108977 A1 | 5/2008 | Heaton et al. |
| 2008/0243096 A1 | 10/2008 | Svedman |
| 2008/0275409 A1 | 11/2008 | Kane et al. |
| 2008/0287973 A1 | 11/2008 | Aster et al. |
| 2008/0306456 A1 | 12/2008 | Riesinger |
| 2009/0005716 A1 | 1/2009 | Abuzaina et al. |
| 2009/0005744 A1 | 1/2009 | Karpowicz et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0137973 A1 | 5/2009 | Karpowicz et al. |
| 2009/0204423 A1 | 8/2009 | DeGheest et al. |
| 2009/0227938 A1 | 9/2009 | Fasching et al. |
| 2009/0246238 A1 | 10/2009 | Gorman et al. |
| 2009/0299303 A1 | 12/2009 | Seegert |
| 2009/0299342 A1* | 12/2009 | Cavanaugh, II .. A61F 13/00017 604/543 |
| 2009/0312685 A1 | 12/2009 | Olsen et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III et al. |
| 2010/0047324 A1 | 2/2010 | Fritz et al. |
| 2010/0081983 A1 | 4/2010 | Zocher et al. |
| 2010/0106184 A1 | 4/2010 | Coward et al. |
| 2010/0121287 A1 | 5/2010 | Smith et al. |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0211030 A1 | 8/2010 | Turner et al. |
| 2010/0256672 A1 | 10/2010 | Weinberg et al. |
| 2010/0262126 A1 | 10/2010 | Hu et al. |
| 2010/0280468 A1 | 11/2010 | Haggstrom et al. |
| 2010/0292717 A1 | 11/2010 | Petter-Puchner et al. |
| 2010/0312159 A1 | 12/2010 | Aali et al. |
| 2011/0009838 A1 | 1/2011 | Greener |
| 2011/0021965 A1 | 1/2011 | Karp et al. |
| 2011/0022082 A1 | 1/2011 | Burke et al. |
| 2011/0054283 A1 | 3/2011 | Shuler |
| 2011/0054365 A1* | 3/2011 | Greener ............. A61M 1/0088 601/6 |
| 2011/0059291 A1 | 3/2011 | Boyce et al. |

(56) References Cited

U.S. PATENT DOCUMENTS

| | | |
|---|---|---|
| 2011/0066096 A1 | 3/2011 | Svedman |
| 2011/0077605 A1 | 3/2011 | Karpowicz et al. |
| 2011/0082480 A1 | 4/2011 | Viola |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0130774 A1 | 6/2011 | Criscuolo et al. |
| 2011/0178451 A1 | 7/2011 | Robinson et al. |
| 2011/0213319 A1 | 9/2011 | Blott et al. |
| 2011/0224631 A1 | 9/2011 | Simmons |
| 2011/0224632 A1 | 9/2011 | Zimnitsky et al. |
| 2011/0224634 A1 | 9/2011 | Locke et al. |
| 2011/0238095 A1 | 9/2011 | Browning |
| 2011/0264138 A1 | 10/2011 | Avelar et al. |
| 2011/0282136 A1 | 11/2011 | Browning |
| 2011/0282310 A1 | 11/2011 | Boehringer et al. |
| 2011/0305736 A1 | 12/2011 | Wieland et al. |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0059399 A1 | 3/2012 | Hoke et al. |
| 2012/0059412 A1 | 3/2012 | Fleischmann |
| 2012/0071841 A1 | 3/2012 | Bengtson |
| 2012/0109188 A1 | 5/2012 | Viola |
| 2012/0121556 A1 | 5/2012 | Fraser et al. |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0144989 A1 | 6/2012 | Du Plessis et al. |
| 2012/0150133 A1 | 6/2012 | Heaton et al. |
| 2012/0165764 A1 | 6/2012 | Allen et al. |
| 2012/0172926 A1 | 7/2012 | Hotter |
| 2012/0191054 A1 | 7/2012 | Kazala, Jr. et al. |
| 2012/0191132 A1 | 7/2012 | Sargeant |
| 2012/0197415 A1 | 8/2012 | Montanari et al. |
| 2012/0209226 A1 | 8/2012 | Simmons et al. |
| 2012/0209227 A1 | 8/2012 | Dunn |
| 2012/0238931 A1* | 9/2012 | Rastegar ............. A61F 13/0246 602/44 |
| 2012/0253302 A1 | 10/2012 | Corley |
| 2012/0277773 A1 | 11/2012 | Sargeant et al. |
| 2013/0012891 A1* | 1/2013 | Gross ................ A61M 37/0015 604/289 |
| 2013/0023842 A1 | 1/2013 | Song |
| 2013/0066365 A1* | 3/2013 | Belson .................. A61B 17/08 606/216 |
| 2013/0096518 A1 | 4/2013 | Hall et al. |
| 2013/0150813 A1 | 6/2013 | Gordon et al. |
| 2013/0150814 A1 | 6/2013 | Buan |
| 2013/0190705 A1 | 7/2013 | Vess et al. |
| 2013/0197457 A1 | 8/2013 | Kazala et al. |
| 2013/0204213 A1 | 8/2013 | Heagle et al. |
| 2013/0245527 A1 | 9/2013 | Croizat et al. |
| 2013/0253401 A1 | 9/2013 | Locke et al. |
| 2013/0325142 A1 | 12/2013 | Hunter et al. |
| 2013/0331757 A1 | 12/2013 | Belson |
| 2014/0068914 A1 | 3/2014 | Coward et al. |
| 2014/0094730 A1 | 4/2014 | Greener |
| 2014/0109560 A1* | 4/2014 | Ilievski .................. B25J 9/142 60/327 |
| 2014/0163415 A1 | 6/2014 | Zaiken et al. |
| 2014/0249495 A1 | 9/2014 | Mumby |
| 2015/0025484 A1 | 1/2015 | Simmons et al. |
| 2015/0065968 A1 | 3/2015 | Sealy et al. |
| 2015/0119837 A1 | 4/2015 | Thompson, Jr. et al. |
| 2015/0148760 A1 | 5/2015 | Dodd et al. |
| 2015/0157758 A1 | 6/2015 | Blucher et al. |
| 2015/0159066 A1 | 6/2015 | Hartwell et al. |
| 2015/0174304 A1 | 6/2015 | Askem et al. |
| 2015/0190288 A1 | 7/2015 | Dunn et al. |
| 2015/0196431 A1 | 7/2015 | Dunn et al. |
| 2015/0320602 A1 | 11/2015 | Locke et al. |
| 2016/0166744 A1 | 6/2016 | Hartwell et al. |
| 2017/0065751 A1 | 3/2017 | Toth |
| 2017/0156611 A1 | 6/2017 | Burnett et al. |

FOREIGN PATENT DOCUMENTS

| | | |
|---|---|---|
| CN | 1438904 | 8/2003 |
| CN | 101112326 A | 1/2008 |
| CN | 101123930 | 2/2008 |
| CN | 101588836 | 11/2009 |
| CN | 101744688 A | 6/2010 |
| CN | 201519362 U | 7/2010 |
| CN | 102038575 A | 5/2011 |
| CN | 102046117 | 5/2011 |
| CN | 102196830 | 9/2011 |
| CN | 102256637 | 11/2011 |
| CN | 102781380 | 11/2012 |
| CN | 202568632 U | 12/2012 |
| CN | 103071197 A | 5/2013 |
| CN | 203408163 | 1/2014 |
| DE | 2 949 920 | 3/1981 |
| DE | 10 2005 00701 | 8/2006 |
| EP | 1 320 342 | 6/2003 |
| EP | 2 279 016 | 2/2011 |
| EP | 2 366 721 | 9/2011 |
| EP | 2 368 523 | 9/2011 |
| EP | 2 404 626 | 1/2012 |
| EP | 2 341 955 | 12/2012 |
| EP | 2547375 A1 | 1/2013 |
| EP | 2 567 682 | 3/2013 |
| EP | 2 567 717 | 3/2013 |
| EP | 2 594 299 | 5/2013 |
| EP | 2 601 984 A2 | 6/2013 |
| EP | 2 623 137 | 8/2013 |
| EP | 2 367 517 | 9/2013 |
| EP | 3 225 261 | 10/2017 |
| GB | 2389794 | 12/2003 |
| GB | 2378392 B | 6/2004 |
| GB | 2423019 | 8/2006 |
| GB | 2489947 | 10/2012 |
| GB | 2496310 | 5/2013 |
| JP | S62-57560 A | 3/1987 |
| JP | 2006-528038 A | 12/2006 |
| JP | 2007-505678 | 3/2007 |
| JP | 2008-529618 | 8/2008 |
| JP | 2009-525087 A | 7/2009 |
| JP | 2009-536851 | 10/2009 |
| JP | 2011-523575 | 8/2011 |
| JP | 2012-105840 A | 6/2012 |
| RU | 62504 | 4/2007 |
| SU | 1818103 | 5/1993 |
| WO | WO 2001/085248 | 11/2001 |
| WO | WO 2001/089392 | 11/2001 |
| WO | WO 2002/05737 | 1/2002 |
| WO | WO 2003/003948 | 1/2003 |
| WO | WO 03/049598 A2 | 6/2003 |
| WO | WO 2004/018020 | 3/2004 |
| WO | WO 2004/037334 | 5/2004 |
| WO | WO 2005/046761 | 5/2005 |
| WO | WO 2005/105174 | 11/2005 |
| WO | WO 2006/041496 A1 | 4/2006 |
| WO | WO 2006/046060 | 5/2006 |
| WO | WO 2007/030601 | 3/2007 |
| WO | WO 2007/133618 | 11/2007 |
| WO | WO 2008/027449 A2 | 3/2008 |
| WO | WO 2008/039223 | 4/2008 |
| WO | WO 2008/064502 | 6/2008 |
| WO | WO 2008/091521 | 7/2008 |
| WO | WO 2008/104609 | 9/2008 |
| WO | WO 2009/019495 | 2/2009 |
| WO | WO 2009/071926 | 6/2009 |
| WO | WO 2009/071933 | 6/2009 |
| WO | WO 2009/112062 | 9/2009 |
| WO | WO 2009/112848 | 9/2009 |
| WO | WO 2009/114624 | 9/2009 |
| WO | WO 2009/156709 | 12/2009 |
| WO | WO 2009/158132 | 12/2009 |
| WO | WO 2010/033725 | 3/2010 |

(56) References Cited

FOREIGN PATENT DOCUMENTS

| | | |
|---|---|---|
| WO | WO 2010/051073 | 5/2010 |
| WO | WO 2010/059612 | 5/2010 |
| WO | WO 2010/075180 | 7/2010 |
| WO | WO 2010/078349 | 7/2010 |
| WO | WO 2010/092334 | 8/2010 |
| WO | WO 2010/097570 | 9/2010 |
| WO | WO 2011/023384 | 3/2011 |
| WO | WO 2011/087871 | 7/2011 |
| WO | WO 2011/091169 | 7/2011 |
| WO | WO 2011/106722 | 9/2011 |
| WO | WO 2011/135284 | 11/2011 |
| WO | WO 2011/135286 | 11/2011 |
| WO | WO 2011/135287 | 11/2011 |
| WO | WO 2011/137230 | 11/2011 |
| WO | WO 2011/144888 | 11/2011 |
| WO | WO 2012/021553 | 2/2012 |
| WO | WO 2012/038727 | 3/2012 |
| WO | WO 2012/069793 A1 | 5/2012 |
| WO | WO 2012/082716 | 6/2012 |
| WO | WO 2012/082876 | 6/2012 |
| WO | WO 2012/112204 | 8/2012 |
| WO | WO 2012/136707 | 10/2012 |
| WO | WO 2012/142473 | 10/2012 |
| WO | WO 2012/156655 | 11/2012 |
| WO | WO 2012/168678 | 12/2012 |
| WO | WO 2013/007973 | 1/2013 |
| WO | WO 2013/012381 | 1/2013 |
| WO | WO 2013/043258 | 3/2013 |
| WO | WO 2013/071243 | 5/2013 |
| WO | WO 2013/079947 | 6/2013 |
| WO | WO 2013/175309 | 11/2013 |
| WO | WO 2013/175310 | 11/2013 |
| WO | WO 2014/013348 | 1/2014 |
| WO | WO 2014/014842 | 1/2014 |
| WO | WO 2014/014871 | 1/2014 |
| WO | WO 2014/014922 | 1/2014 |
| WO | WO 2014/024048 | 2/2014 |
| WO | WO 2014/140578 | 9/2014 |
| WO | WO 2014/158526 | 10/2014 |
| WO | WO 2014/165275 | 10/2014 |
| WO | WO 2014/178945 A1 | 11/2014 |
| WO | WO 2015/008054 | 1/2015 |
| WO | WO 2015/061352 | 4/2015 |
| WO | WO 2015/109359 | 7/2015 |
| WO | WO 2015/110409 | 7/2015 |
| WO | WO 2015/110410 | 7/2015 |
| WO | WO 2016/176513 | 11/2016 |

OTHER PUBLICATIONS

Definition of "Throughout", Merriam-Webster Dictionary, accessed Aug. 29, 2017, in 11 pages. URL: https://www.merriam-webster.com/dictionary/throughout.

Hougaard, et al., "The open abdomen: temporary closure with a modified negative pressure therapy technique", International Wound Journal, (2014), ISSN 1742-4801, pp. 13-16.

International Search Report and Written Opinion, re PCT Application No. PCT/IB2013/002485, dated Apr. 23, 2014.

International Preliminary Report on Patentability, re PCT Application No. PCT/IB2013/002485, dated Dec. 4, 2014.

Kapischke, et al., "Self-fixating mesh for the Lichtenstein procedure-a prestudy", Langenbecks Arch Surg (2010), 395 pp. 317-322.

Definition of "3D Printer", American Heritage Dictionary of the English Language, Fifth Edition, 2016, accessed Feb. 22, 2018, in 1 page. URL: https://www.thefreedictionary.co.

\* cited by examiner

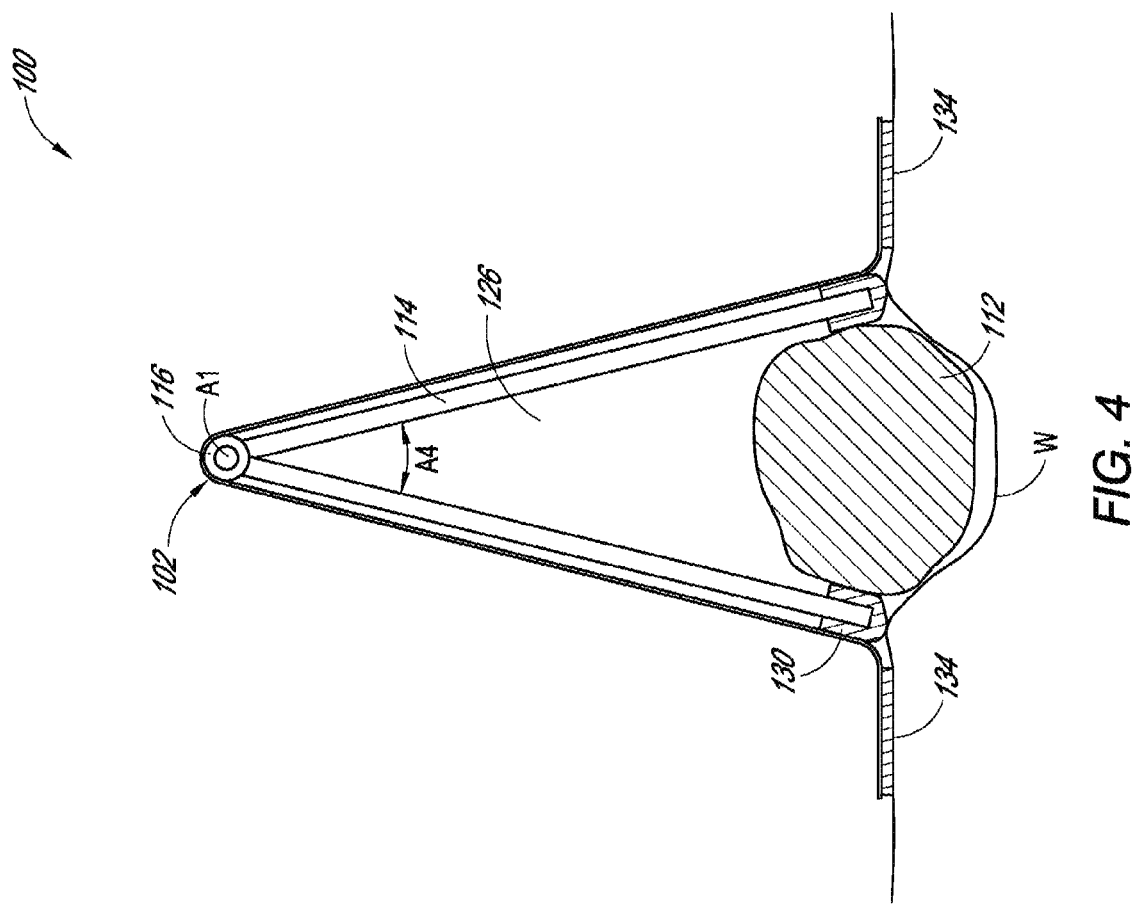

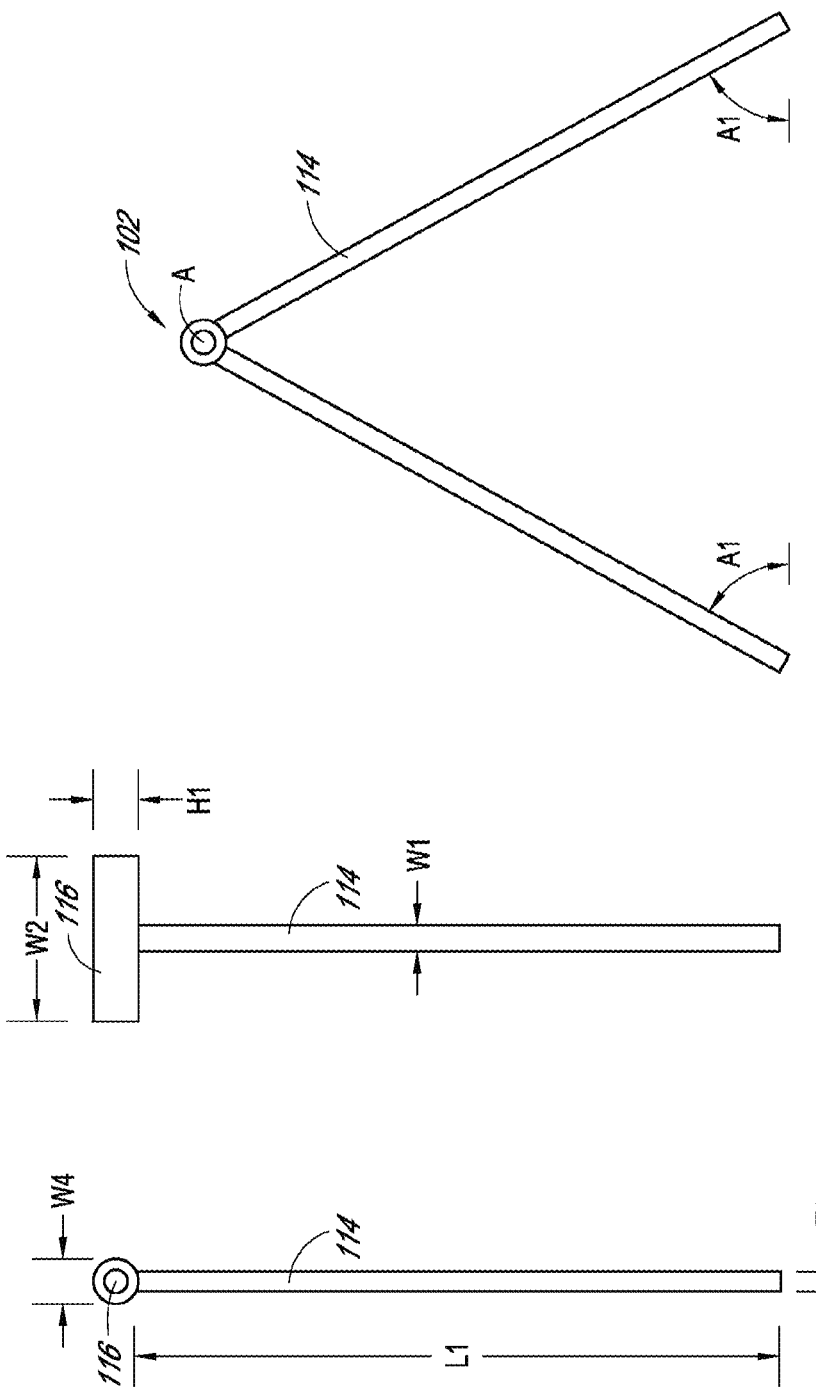

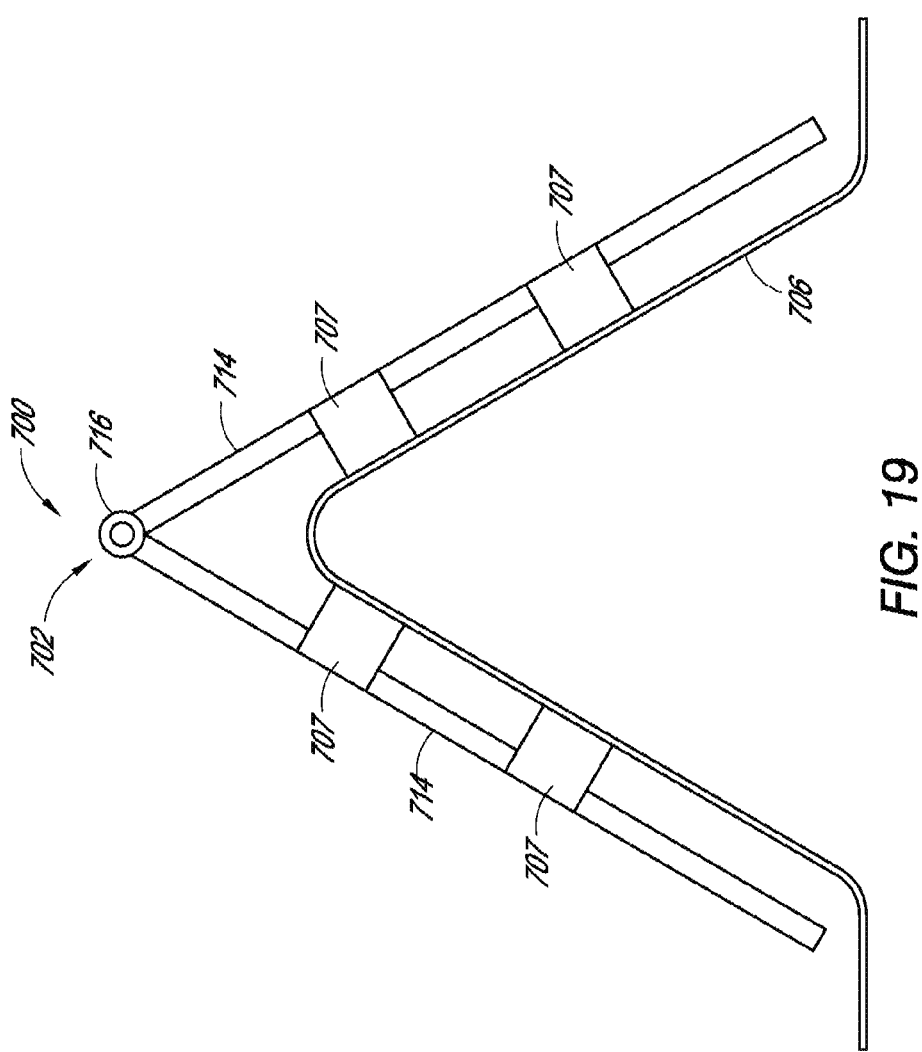

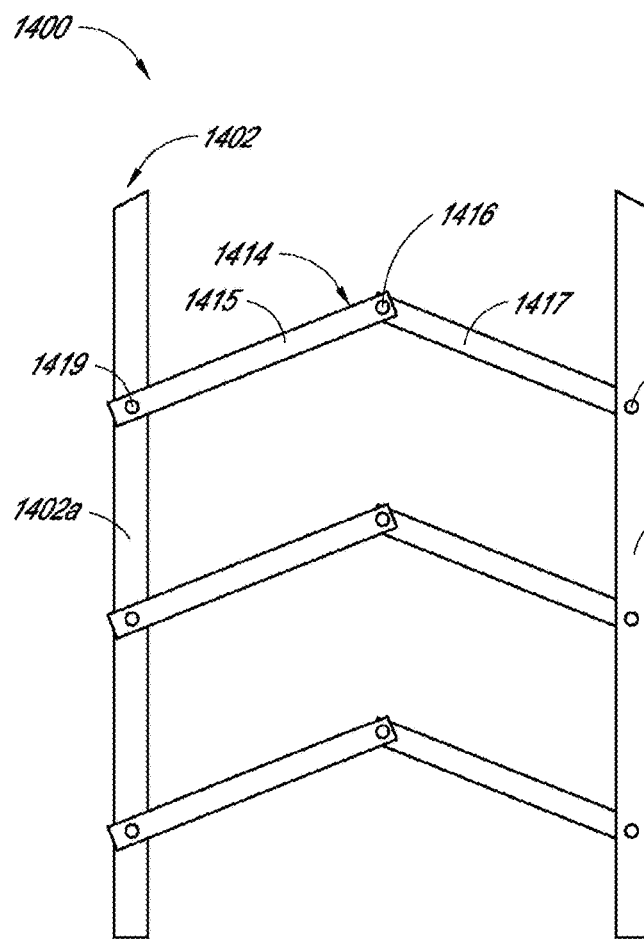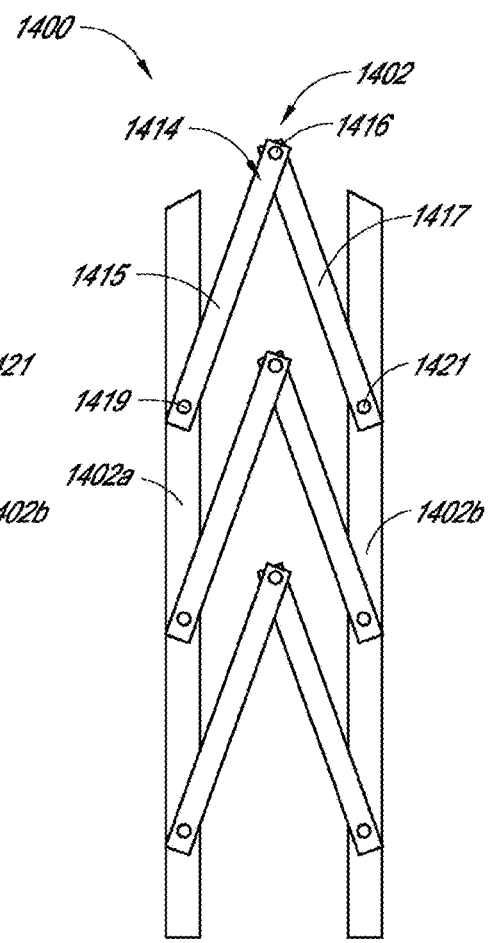
FIG. 28A                    FIG. 28B

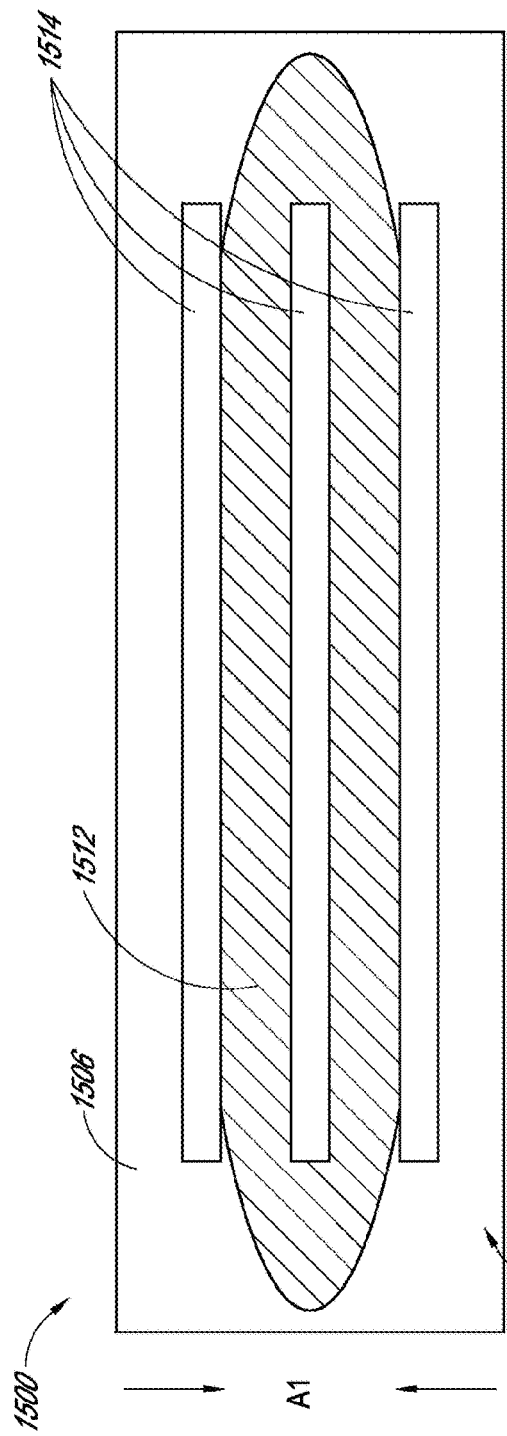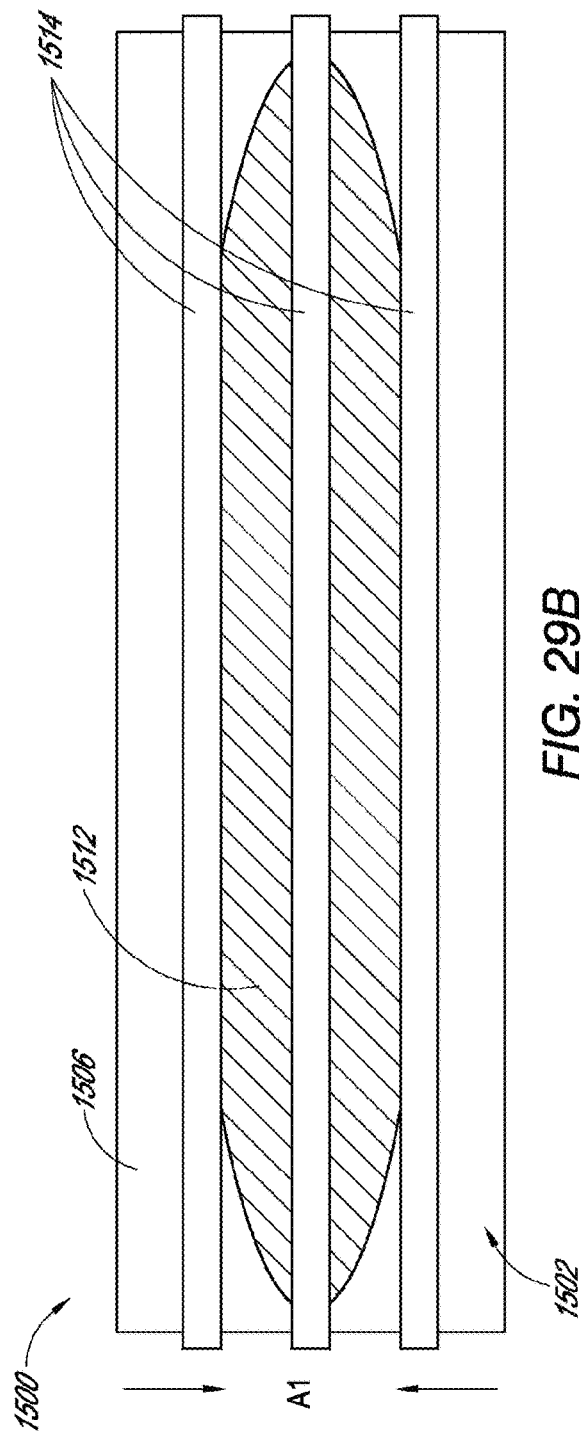

[1]

WOUND CLOSURE DEVICE

INCORPORATION BY REFERENCE AND CROSS-REFERENCE TO RELATED APPLICATIONS

This application is a continuation application of U.S. patent application Ser. No. 14/402674, filed Nov. 20, 2014, which is a National Phase Application of PCT Patent Application PCT/1132013/002485, filed on May 21, 2013, which claims the benefit of U.S. Provisional Application Nos. 61/650,391, filed May 22, 2012, 61/681,037, filed Aug. 8, 2012, 61/784,304, filed Mar. 14, 2013, and 61/651,483, filed May 24, 2012, the contents of which are hereby incorporated by reference in their entireties as if fully set forth herein. The benefit of priority to the foregoing applications is claimed under the appropriate legal basis including, without limitation, under 35 U.S.C. § 119(e).

BACKGROUND OF THE DISCLOSURE

Field of the Disclosure

Embodiments or arrangements disclosed herein relate to methods and apparatuses for dressing and treating a wound with topical negative pressure (TNP) therapy. For example but without limitation, some embodiments disclosed herein relate to treating a wound with reduced pressure provided from a pump. As another non-limiting example, some embodiments disclosed herein relate to apparatuses and methods for controlling the operation of a TNP system.

Description of the Related Art

A number of techniques have been developed for treatment of wounds, including wounds resulting from accident and wounds resulting from surgery. Often, wounds are closed using sutures or staples. However, inserting these mechanical closure techniques requires making additional punctures or wounds to the skin, which can result in tissue injury and in the case of excess swelling, possible ischemia and tissue loss. Also, mechanical wound closures such as staples and sutures can cause highly-localized stresses at the insertion points that can impede and damage the normal wound healing processes of the skin.

In recent years, there has been increased interest in using negative pressure devices for the treatment of wounds. Negative pressure wound treatment utilizes devices that remove wound fluids by applying negative pressure suction to the wound. It is believed that such negative pressures promote wound healing by facilitating the formation of granulation tissue at the wound site and assisting the body's normal inflammatory process while simultaneously removing excess fluid, which may contain adverse cytokines bacteria. However, further improvements in negative pressure wound therapy are needed to fully realize the benefits of treatment.

Many different types of wound dressings are known for aiding in the healing process of a human or animal. These different types of wound dressings include many different types of materials and layers, for example, gauze, pads, foam pads or multi-layer wound dressings. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates and may reduce bacterial load and thus, infection to the wound. Furthermore, TNP therapy permits less outside disturbance of the wound and promotes more rapid healing.

Surgeons have described open wounds that are difficult to close such as open abdominal wounds after surgery and fasciotomy wounds. These wounds cannot always be closed and can require skin grafts to aid the closure. In some cases, the dressing itself may hinder the closure of the wound by creating a stiffened layer of material over the wound that is resistant to contraction.

SUMMARY OF THE SOME EMBODIMENTS

Embodiments of the present disclosure relate to wound dressings configured to provide a sealed cover over a wound, providing a sealed space over the wound suitable for maintaining a desired level of reduced pressure within the sealed space over the wound.

Some embodiments are directed to a wound dressing for use in the application of negative pressure to a wound of a patient's body, comprising a support member having a plurality of legs (also referred to herein as arms or body portions) and a top portion (also referred to herein as a top portion), the legs projecting from the top portion and being positionable adjacent a periphery of the wound, and a cover member positionable over the support member. Each leg can be configured to be rotabable relative to an axis axially through the top portion so that a rotational position of each leg of the support member can be adjusted and such that the width of the support member can be adjusted.

Some embodiments comprise a wound dressing for use in the application of negative pressure to a wound of a patient's body, comprising a support member having a first side support and a second side support coupled with a top portion, and a cover member positionable over the support member. In some embodiments, the first side support can be rotatable about the top portion, the second side support can be rotatable about the top portion, and the first side support can be rotatable relative to the second side support so that a rotational position of the first side support and the second side support can be adjusted and such that the width of the support member can be adjusted.

Some embodiments are directed to a method of treating a wound, comprising positioning a support member having a first side support and a second side support both rotatably coupled to a top portion at a location adjacent the wound such that the first side support and the second side support are positioned adjacent the periphery of the wound, positioning a wound cover over the wound, sealing the wound cover to the skin surrounding the wound so that a substantially fluid-tight space is created over the wound, and applying negative pressure to the space over the wound through a conduit in fluid communication with the space over the wound. In some embodiments, the application of negative pressure can cause the first side support and the second side support to rotate relative to an axis through the top portion to decrease a width of the support member and draw edges of the wound closer together.

Some embodiments comprise a support structure for placement in a wound, comprising an elongate top portion extending along a longitudinal axis, and a plurality of side supports connected to the elongate top portion and rotatable about the longitudinal axis, wherein at least one of the side supports is configured to be positioned adjacent one side of a wound and at least another of the side supports is configured to be positioned adjacent another side of the wound.

Any of the features, components, or details of any of the arrangements or embodiments disclosed in this application, including those disclosed below, are interchangeably combinable with any other features, components, or details of any of the arrangements or embodiments disclosed herein to form new arrangements and embodiments. With that, the following arrangements are disclosed herein, inter alia.

1. A wound dressing for use in the application of negative pressure to a wound, comprising:
   a support member comprising:
      first support element having a first portion aligned with a first axis and a body portion coupled with and extending away from the first portion; and
      a second support element having a first portion aligned with the first axis and a body portion coupled with and extending away from the first portion of the second support element;
   a cover member positionable over the wound in use;
   wherein:
      at least the body portion of each of the first support element and the second support element are independently rotatable about the first axis;
      the support member is configured to support at least a middle portion of the cover member above a surface of the wound out of contact with the wound so as to define a space between the wound cover and the wound.

2. The wound dressing of arrangement 1, wherein the support member is configured such that, in use, the body portion of the first support element is adjustable so as to extend in a first direction away from the first axis and the body portion of the second support element is adjustable so as to extend in a second direction away from the first axis, the second direction being different than the first direction such that an angle is defined between the body portion of the first support element and the body portion of the second support element.

3. The wound dressing of arrangement 2, wherein the angle between the body portion of the first support element and the body portion of the second support element is from approximately 50 degrees to approximately 90 degrees, or from approximately 50 degrees to approximately 70 degrees, before reduced pressure has been supplied to the space between the cover member and the wound and wherein the angle between the body portion of the first support element and the body portion of the second support element is from approximately 0 degrees to approximately 40 degrees, or from approximately 0 degrees to approximately 20 degrees, or from approximately 10 degrees to approximately 20 degrees, after reduced pressure has been supplied to the space between the cover member and the wound.

4. The wound dressing of any one of the previous arrangements, wherein:
   the support member is positionable over the wound such that, in use, the body portion of the first support element extends toward a first side edge of the wound and the body portion of the second support element extends toward a second side edge of the wound;
   the second side edge of the wound is approximately opposite to the first side edge of the wound; and
   the support member is configured such that the body portion of the first support element and the body portion of the second support element can rotate toward each other so as to reduce an angle between the body portion of the first support element and the body portion of the second support element.

5. The wound dressing of any one of arrangements 2-3, wherein the wound dressing is configured such that, when reduced pressure is supplied to the space between the cover member and the wound, the body portion of the first support element is configured to rotate about the first axis toward the body portion of the second support element so as to reduce the angle between body portion of the first support element and the body portion of the second support element.

6. The wound dressing of any one of the previous arrangements, wherein the cover member is configured to adhere to a skin surface surrounding the wound and to provide a substantially gas-tight sealed space over the wound, and wherein the cover member does not have adhesive in a middle portion of the cover member.

7. The wound dressing of any one of the previous arrangements, wherein the support member further comprises a shaft member coaxial with the first axis, and wherein the first support element and the second support element are configured to rotate about the shaft member.

8. The wound dressing of any one of the previous arrangements, wherein the first portion of at least one of the first support element and the second support element defines a cylindrical shape and has an opening axially therethrough, the opening being coaxial with the first axis.

9. The wound dressing of any one of the previous arrangements, wherein a length of the body portion of the first support element is adjustable in the first direction relative to the first axis and/or a length of the body portion of the second support element is adjustable in the second direction relative to the first axis.

10. The wound dressing of any one of the previous arrangements, wherein the cover member is positioned between the support member and the wound in use.

11. The wound dressing of any one of the previous arrangements, wherein the cover member is positioned between the support member and the wound in use, the cover member being tethered to the support member so that the support member maintains the cover member out of contact with the wound.

12. The wound dressing of any one of the previous arrangements, wherein the cover member is configured to be positioned over the support member in use.

13. The wound dressing of any one of the previous arrangements, further comprising:
   a third support element having a first portion aligned with the first axis and a body portion coupled with and extending away from the first portion thereof; and
   a fourth support element having a first portion aligned with the first axis and a body portion coupled with and extending away from the first portion thereof.

14. The wound dressing of any one of the previous arrangements, further comprising a conduit in fluid communication with the space between the cover member and the wound, the conduit being configured to provide reduced pressure to said space.

15. The wound dressing of any one of the previous arrangements, further comprising a wound filler positionable between the cover member and the wound in use.

16. The wound dressing of any one of the previous arrangements, comprising a wound filler positionable between the cover member and the wound in use, the filler comprising at least one of foam, gauze, a deflatable hollow member, a sealed enclosure, a sealed enclosure having a collapsible structure therein, and any combination of the foregoing.

17. The wound dressing of any one of the previous arrangements, comprising a collapsible wound filler positionable between the cover member and the wound in use, the collapsible wound filler comprising at least one of foam, gauze, a deflatable hollow member, a sealed enclosure, a sealed enclosure having a collapsible structure therein, and any combination of the foregoing.

18. The wound dressing of any one of the previous arrangements, comprising a collapsible wound filler positionable between the cover member and the wound in use, the collapsible wound filler comprising at least one of foam, gauze, a deflatable hollow member, a sealed enclosure, a sealed enclosure having a collapsible structure therein, and any combination of the foregoing, wherein the collapsible wound filler is configured to be more flexible and, hence, more collapsible, in a lateral direction than in a vertical direction.

19. The wound dressing of any one of the previous arrangements, comprising a collapsible wound filler positionable between the cover member and the wound in use, wherein the wound filler is configured to support an end portion of the body portion of the first support element and an end portion of the body portion of the second support element in use.

20. The wound dressing of any one of the previous arrangements, comprising from 4 to 8 first support elements and from 4 to 8 second support elements.

21. The wound dressing of any one of the previous arrangements, wherein at least one of the first support element and the second support element is wider in a direction parallel to the first axis than it is longer in a direction away from the first axis.

22. The wound dressing of any one of the previous arrangements, comprising:
a plurality of first support elements and a first connector fixed to the body portion of each of the plurality of first support elements, thereby connecting the body portion of each of the plurality of first support elements together; and
a plurality of second support elements and a second connector fixed to the body portion of each of the plurality of second support elements, thereby connecting the body portion of each of the plurality of second support elements together.

23. The wound dressing of any one of the previous arrangements, comprising a pad positioned at an end portion of the body portion of at least one of the first and the second support elements.

24. A wound dressing kit, comprising the wound dressing of any one of the preceding arrangements and a vacuum pump.

25. A wound dressing kit, comprising the wound dressing of any one of the preceding arrangements, a vacuum pump, and a collection canister for collection of wound exudate removed from the wound.

26. A wound dressing for use in the application of negative pressure to a wound of a patient's body, comprising:
a support member having a plurality of legs and a body portion, the legs projecting from the body portion and being positionable adjacent a periphery of the wound; and
a cover member positionable over the support member;
wherein each leg is rotatable relative to an axis extending axially through the body portion so that a rotational position of each leg of the support member can be adjusted and such that the width of the support member can be adjusted.

27. The wound dressing of arrangement 26, wherein portions of the body portion can be rotated independently.

28. The wound dressing of any one of arrangements 26-27, wherein each portion of the body portion supports at least one leg.

29. The wound dressing of any one of arrangements 26-28, further comprising foam or other wound packing positionable between the wound and the cover member.

30. The wound dressing of any one of arrangements 26-29, wherein one or more of the legs has an adjustable length.

31. The wound dressing of any one of arrangements 26-30, wherein at least a portion of one or more of the legs is extendible to adjust the length thereof.

32. The wound dressing of any one of arrangements 26-31, wherein the cover member is a liquid impermeable drape.

33. The wound dressing of any one of arrangements 26-32, wherein the body portion comprises an elongate member, and further comprising a shaft positioned through an axial centerline of the body portion.

34. The wound dressing of any one of arrangements 26-33, comprising a conduit in communication with a space beneath the cover member, the conduit configured to provide a source of reduced pressure to said space.

35. The wound dressing of any one of arrangements 26-34, comprising one or more cross-supports coupled with two or more legs along one side of the support member.

36. The wound dressing of any one of arrangements 26-35, comprising one or more cross-supports coupled with two or more legs along each side of the support member.

37. The wound dressing of any one of arrangements 26-36, wherein the cover member is positioned mostly outside of the support member.

38. The wound dressing of any one of arrangements 26-37, wherein the cover member is positioned mostly between the support member and the wound.

39. A wound dressing for use in the application of negative pressure to a wound of a patient's body, comprising:
a support member having a first side support and a second side support coupled with a body portion; and
a cover member positionable over the support member;
wherein:
the first side support is rotatable about the body portion;
the second side support is rotatable about the body portion;
the first side support is rotatable relative to the second side support so that a rotational position of the first side support and the second side support can be adjusted and such that the width of the support member can be adjusted.

40. The wound dressing of arrangement 39, wherein at least one of the first side support and the second side support comprises two or more legs.

41. The wound dressing of any one of arrangements 39-40, wherein at least one of the first side support and the second side support comprises two or more legs and a cross-support.

42. The wound dressing of any one of arrangements 39-41, wherein at least one of the first side support and the second side support comprises a panel.

43. The wound dressing of any one of arrangements 39-42, wherein portions of the body portion can be rotated independently.

44. The wound dressing of arrangement 43, wherein each portion of the body portion supports at least one leg.

45. The wound dressing of any one of arrangements 39-44, further comprising foam or other wound packing positionable between the wound and the cover member.

46. The wound dressing of any one of arrangements 39-45, comprising one or more legs that has an adjustable length.

47. The wound dressing of any one of arrangements 39-46, comprising one or more legs that is extendible to adjust the length thereof.

48. The wound dressing of any one of arrangements 39-47, wherein the cover member is a liquid impermeable drape.

49. The wound dressing of any one of arrangements 39-48, wherein the body portion comprises an elongate member, and further comprising a shaft positioned through an axial centerline of the body portion.

50. The wound dressing of any one of arrangements 39-49, comprising a conduit in communication with a space beneath the wound cover, the conduit configured to provide a source of reduced pressure to said space.

51. The wound dressing of any one of arrangements 39-50, comprising one or more cross-supports coupled with two or more legs along one side of the support member.

52. The wound dressing of any one of arrangements 39-51, comprising one or more cross-supports coupled with two or more legs along each side of the support member.

53. The wound dressing of any one of arrangements 39-52, wherein the cover member is positioned mostly outside of the support member.

54. A wound dressing kit, comprising the wound dressing of any one of arrangements 39-53 and a vacuum pump.

55. The wound dressing kit of arrangement 54, further comprising a collection canister for collection of wound exudate.

56. A method of treating a wound, comprising:
positioning a support member having a first side support and a second side support both rotatably coupled to a body portion at a location adjacent the wound such that the first side support and the second side support are positioned adjacent the periphery of the wound;
positioning a wound cover over the wound;
sealing the wound cover to the skin surrounding the wound so that a substantially fluid-tight space is created over the wound; and
applying negative pressure to the space over the wound through a conduit in fluid communication with the space over the wound;
wherein the application of negative pressure causes the first side support and the second side support to rotate relative to an axis through the body portion to decrease a width of the support member and draw edges of the wound closer together.

57. The method of treating a wound of arrangement 56, comprising positioning the wound cover between the wound and the support member.

58. The method of treating a wound of any one of arrangements 56-57, comprising positioning the wound cover over an outside of the support member.

59. The method of treating a wound of any one of arrangements 56-58, wherein at least one of the first side support and the second side support comprises two or more legs.

60. The method of treating a wound of any one of arrangements 56-59, wherein at least one of the first side support and the second side support comprises two or more legs and a cross-support.

61. The method of treating a wound of any one of arrangements 56-60, wherein at least one of the first side support and the second side support comprises a panel.

62. The method of treating a wound of any one of arrangements 56-61, comprising rotating portions of the body portion independently.

63. The method of treating a wound of any one of arrangements 56-62, comprising positioning foam or other wound packing between the wound and the cover member.

64. The method of treating a wound of any one of arrangements 56-63, comprising first positioning foam adjacent the wound, and then positioning the first and second side supports adjacent edges of the foam.

65. The method of treating a wound of arrangement 64, wherein the first and second side supports are positioned into slits in the foam.

66. The method of treating a wound of any one of arrangements 56-65, comprising adjusting a length of at least one of the first side support and the second side support.

67. The method of treating a wound of any one of arrangements 56-66, wherein the cover member is a liquid impermeable drape.

68. The method of treating a wound of any one of arrangements 56-67, wherein the first and second side supports are rotatable about a shaft positioned through an axial centerline of the body portion.

69. The method of treating a wound of any one of arrangements 56-68, wherein the support member comprises one or more cross-supports coupled with two or more legs along one side of the support member.

70. The method of treating a wound of any one of arrangements 56-69, wherein the support member comprises one or more cross-supports coupled with two or more legs along each side of the support member.

71. The method of treating a wound of any one of arrangements 56-70, wherein the support member comprises one or more cross-supports coupled with two or more legs along each side of the support member.

72. The method of treating a wound of any one of arrangements 56-71, wherein the cover member is positioned mostly outside of the support member.

73. A support structure for placement in a wound, comprising:
an elongate body portion extending along a longitudinal axis; and
a plurality of side supports connected to the elongate body portion and rotatable about the longitudinal axis, wherein at least one of the side supports is configured to be positioned adjacent one side of a wound and at least another of the side supports is configured to be positioned adjacent another side of the wound.

74. A wound treatment apparatus, comprising:
an elongate member made of a biocompatible material having a first end and a second end; and
a plurality of legs made of a biocompatible material rotatably connected to the elongate member, each of the legs having a proximal end rotatably connected to the elongate member and a distal end configured to be positioned adjacent a wound, and wherein the legs are capable of rotation to provide at least one leg on a first side of the wound and at least one leg on a second side of the wound.

75. A support structure for placement in a wound, comprising:

an elongate body portion extending along a longitudinal axis; and a plurality of side supports connected to the elongate body portion and rotatable about the longitudinal axis, wherein at least one of the side supports is configured to be positioned adjacent one side of a wound and at least another of the side supports is configured to be positioned adjacent another side of the wound.

76. A wound treatment apparatus, comprising:

a wound filler configured to be positioned in or over a wound site;

a support structure configured to be positioned over the wound filler, the support structure comprising:

an elongate member having a first end and a second end; and a plurality of supports rotatably connected to the elongate member, each of the legs having a proximal end rotatably connected to the elongate member and a distal end configured to be positioned adjacent the wound site, wherein the distal end of at least a first support is configured to be positioned adjacent a first side of the wound site and the distal end of at least a second support is configured to be positioned adjacent an opposite second side of the wound site;

a wound cover configured to be positioned over the wound filler and support structure and configured to be sealed to skin surrounding the wound site; and a negative pressure source configured to provide negative pressure to an area under the wound cover.

77. A method of treating a wound, the method comprising:

placing a support structure adjacent to a wound filler in a wound cavity;

sealing the wound cavity sufficient to permit application of negative pressure to the wound; and providing negative pressure to the wound, wherein the support structure is configured to guide the wound filler such that the wound is permitted to close as the negative pressure is provided to the wound.

78. A method for promoting would healing, the method comprising:

placing a frame over the wound to contact opposite edges of a wound;

applying a material over the frame to define a space between the material and the wound; and applying vacuum force to the space to promote wound healing.

79. A method as in arrangement 78, further comprising, before placing the frame, placing a piece of foam in the wound.

80. A method, comprising:

placing a collapsible frame adjacent to the wound, the frame having a first expanded configuration having a first lateral dimension;

applying negative pressure to create a vacuum in a space defined between the lateral portions of the wound cavity;

wherein negative pressure reduces the first lateral dimension.

81. The method of arrangement 80, further comprising positioning a foam member within the wound.

82. The method of any one of arrangements 80-81, further comprising affixing a cover to the collapsible frame to enclose the space defined between the lateral portions.

83. A method of sealing a wound, comprising:

positioning a frame structure such that legs of the frame structure are proximate to edges of a foam member positioned within the wound; and applying a force that causes the legs of the frame structure to compress the foam and to bring opposite edges of the wound toward each other.

84. The method of arrangement 83, wherein applying a force comprises applying negative pressure.

85. The method of any one of arrangements 83-84, the compression is accomplished through rotation of the legs.

86. A method of treating a wound, comprising:

positioning a wound filler in or over a wound site;

positioning a wound cover over the wound filler and sealing the wound cover to skin surrounding the wound site; and applying negative pressure to an area under the wound cover and horizontally compressing the wound filler as negative pressure is applied.

87. A method of treating a wound, comprising:

positioning a wound filler in or over a wound site;

positioning a support structure over the wound filler, the support structure comprising:

an elongate member having a first end and a second end;

a plurality of supports rotatably connected to the elongate member, each of the legs having a proximal end rotatably connected to the elongate member and a distal end configured to be positioned adjacent the wound site;

wherein positioning the support structure comprises positioning the distal end of at least a first support adjacent a first side of the wound site and positioning the distal end of at least a second support adjacent an opposite second side of the wound site;

positioning a wound cover over the support structure and the wound filler and sealing the support structure to skin surrounding the wound site; and applying negative pressure to an area under the wound cover, wherein the application of negative pressure causes the wound cover to compress against the supports to move the distal ends of the first and second supports toward each other and compress the wound filler there between.

88. A method of treating a wound, comprising:

positioning a support member having a first side support and a second side support both rotatably coupled to a body portion at a location adjacent the wound such that the first side support and the second side support are positioned adjacent the periphery of the wound;

positioning a wound cover over the wound;

sealing the wound cover to the skin surrounding the wound so that a substantially fluid-tight space is created over the wound; and applying negative pressure to the space over the wound through a conduit in fluid communication with the space over the wound;

wherein the application of negative pressure causes the first side support and the second side support to rotate relative to an axis through the body portion to decrease a width of the support member and draw edges of the wound closer together.

BRIEF DESCRIPTION OF THE DRAWINGS

Embodiments of the present disclosure will now be described hereinafter, by way of example only, with reference to the accompanying drawings in which:

FIG. 4 is a side view of the embodiment of the dressing member illustrated in FIG. 1, after reduced pressure has been applied to the space between the wound cover and the wound, showing the improved contraction of the wound with the dressing member embodiment of FIG. 1.

FIGS. 5 and 6 are a side view and a front view of the embodiment of a top portion and an arm of the embodiment of the dressing member illustrated in FIG. 1.

FIG. 7 is a side view of the embodiment of the dressing member illustrated in FIG. 1.

FIGS. 9-1 and 9-2 are front views of an embodiment of a dressing having the support member illustrated in FIG. 8, showing the dressing applied to a wound model after a therapeutic level of reduced pressure has been applied to the wound.

FIG. 19 is a side view of another embodiment of a dressing.

FIGS. 20A-1 and 20A-2 (collectively FIG. 20A) are a photograph and drawing, respectively, of a wound on a tissue model with a conventional dressing thereon prior to the application of reduced pressure.

FIGS. 20B-1 and 20B-2 (collectively FIG. 20B) are a photograph and drawing, respectively, of a wound on a tissue model with a conventional dressing thereon after the application of reduced pressure.

FIGS. 21A-1 and 21A-2 (collectively FIG. 21A) are a photograph and drawing, respectively, of a wound on a tissue model with an improved dressing according to some embodiments of the present disclosure thereon prior to the application of reduced pressure.

FIGS. 21B-1 and 21B-2 (collectively FIG. 21B) are a photograph and drawing, respectively, of a wound on a tissue model with an improved dressing according to some embodiments of the present disclosure thereon after the application of reduced pressure.

FIGS. 23A-1 and 23A-2 (collectively FIG. 23A) are isometric illustrations of another embodiment of a wound dressing having a support member.

FIGS. 23B-1 and 23B-2 (collectively FIG. 23B) are isometric illustrations of the embodiment of the wound dressing having a support member shown in FIG. 23A, with a wound cover over the support member and after reduced pressure has been applied to a space between the wound cover and the wound.

FIGS. 24A-1 and 24A-2 (collectively FIG. 24A) are isometric illustrations of another embodiment of a wound dressing having a support member, showing the support member in a first state (also referred to herein as an expanded state).

FIGS. 24B-1 and 24B-2 (collectively FIG. 24B) are isometric illustrations of the embodiment of the wound dressing of FIG. 24A showing the support member in a second state (also referred to herein as a contracted state).

FIG. 28A is a top view of another embodiment of a support member of a wound dressing, showing the support member in a first state (also referred to herein as an expanded state).

FIG. 28B is a top view of the embodiment of the support member of FIG. 28A, showing the support member in a second state (also referred to herein as a contracted state).

FIGS. 29A-29B are top views of additional embodiments of wound dressings.

DETAILED DESCRIPTION OF THE PREFERRED EMBODIMENTS

Figure 1:
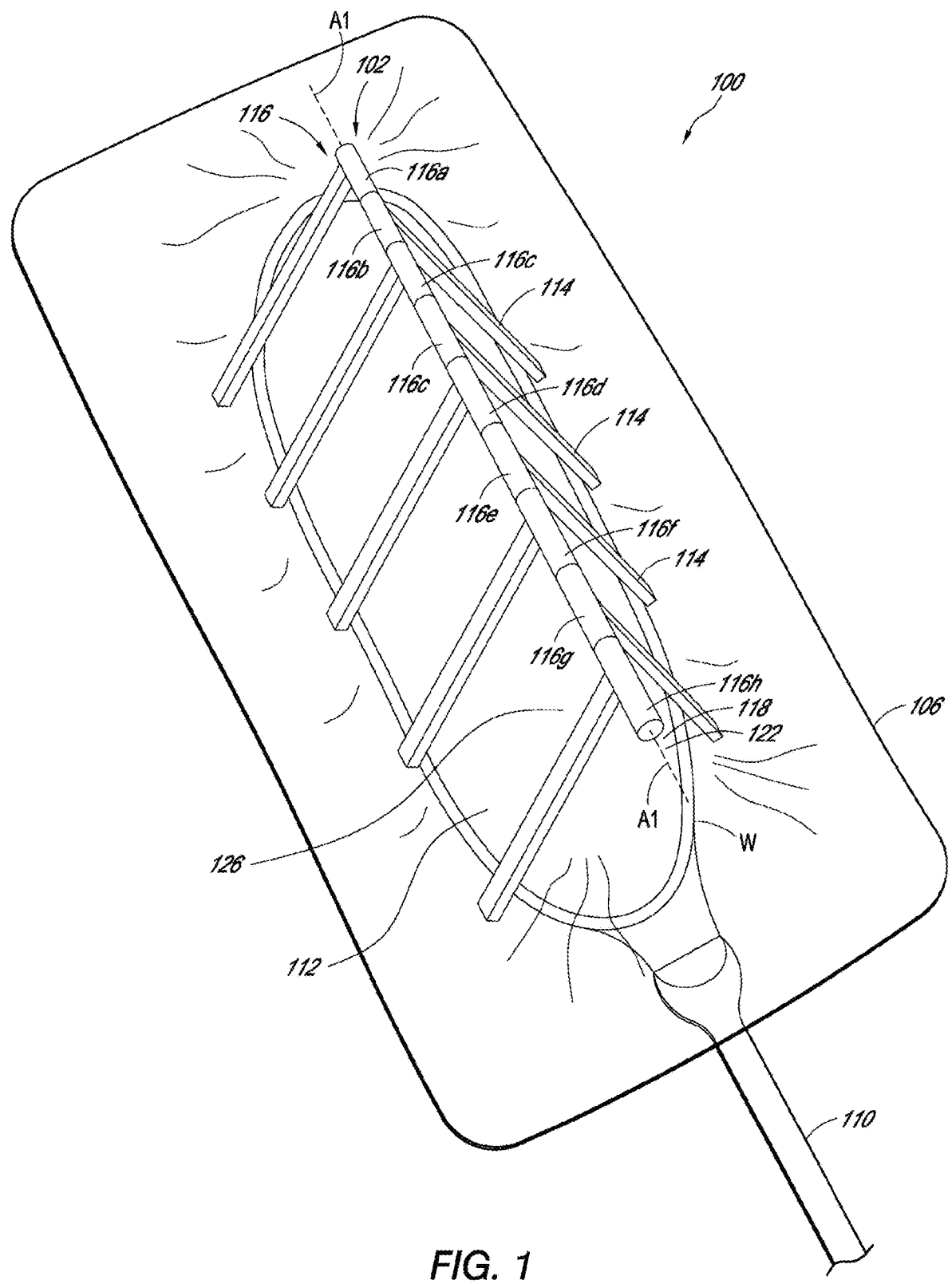
FIG. 1 is an isometric illustration of an embodiment of a wound dressing having a support member.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

As is used herein, reduced or negative pressure levels, such as −X mmHg, represent pressure levels that are below standard atmospheric pressure, which corresponds to 760 mmHg (or 1 atm, 29.93 in Hg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −20 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even 150 mmHg, can be supplied by the negative pressure apparatus.

The wound dressing embodiments disclosed herein are configured to aid with the closure of difficult to close wounds. Such embodiments provide support to the dressing or overlay to raise the overlay above the wound surface with a support system that is flexible and is easily contracted in the lateral direction, thereby reducing the lateral "stiffness" that is exerted on the wound by the overlay or dressing. In conventional dressings, the overlay itself, when drawn against the wound under negative pressure, can inhibit the inward movement of the sides of the wound, thereby inhibiting the closure of the wound.

Figure 2:
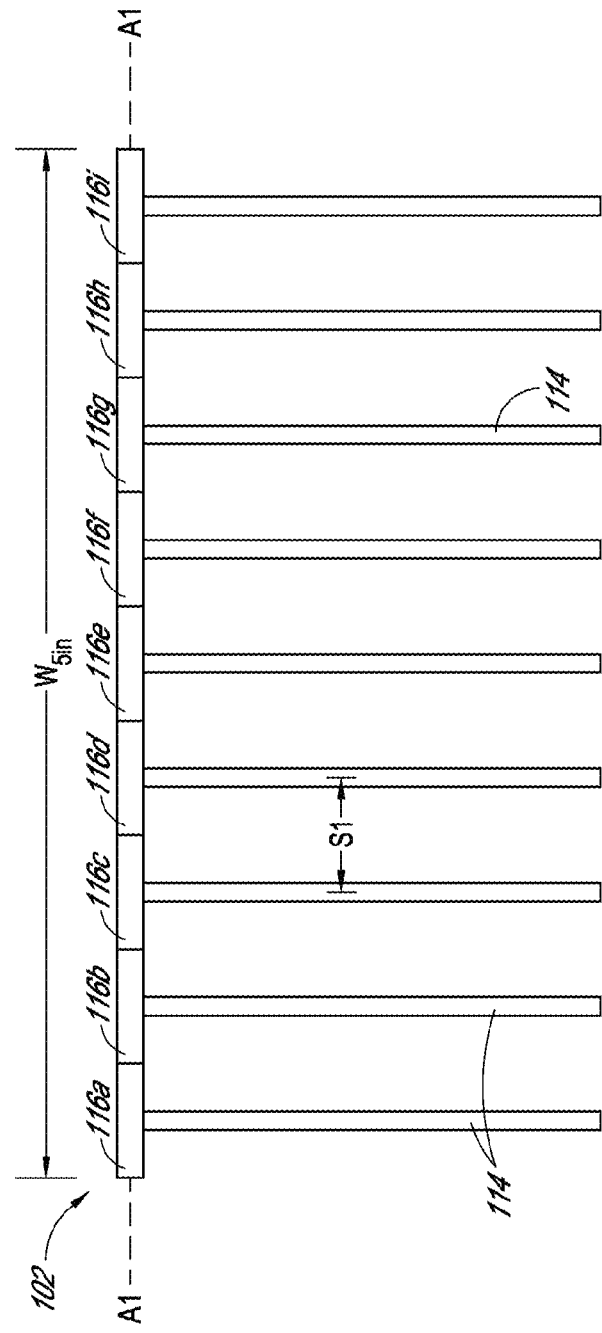
FIG. 2 is a front view of the embodiment of the support member of the dressing member embodiment illustrated in FIG. 1.
Figure 3:
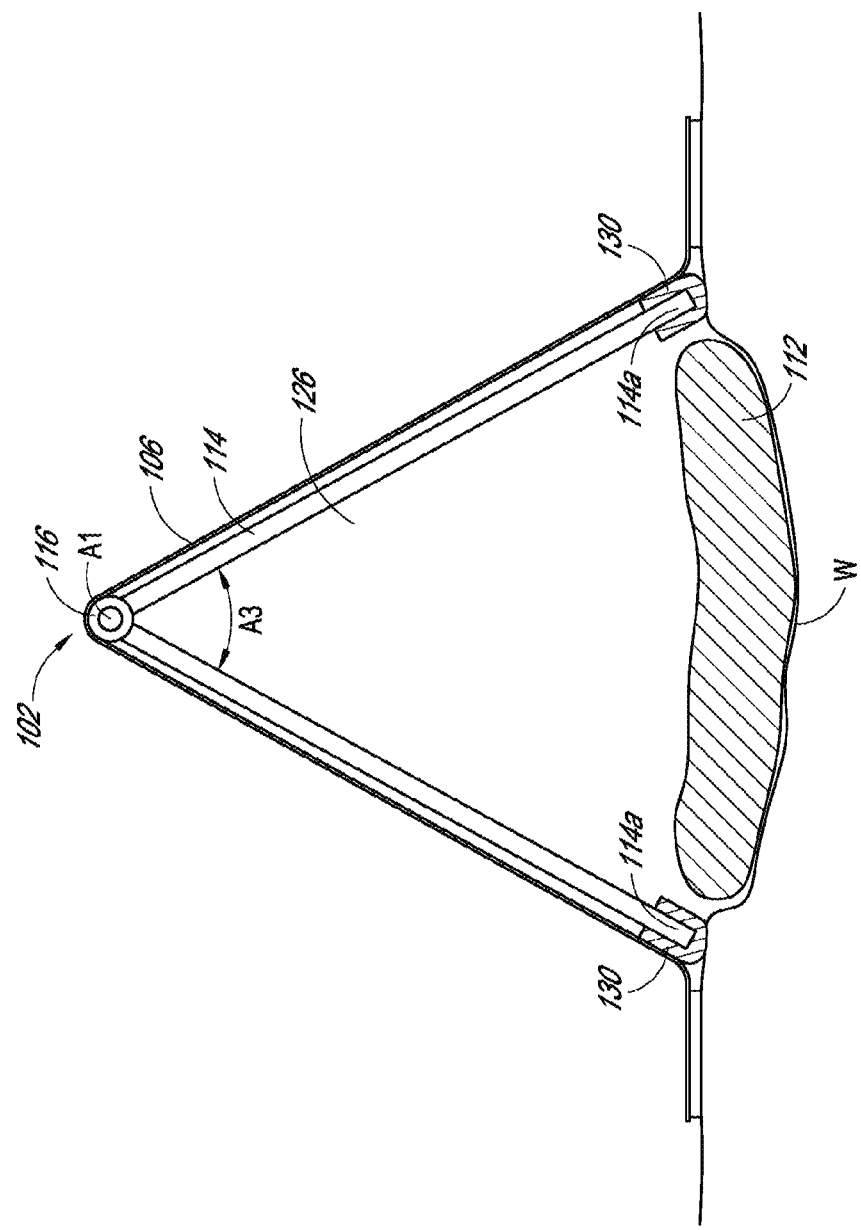
FIG. 3 is a side view of the embodiment of the dressing member illustrated in FIG. 1, before reduced pressure has been applied to the space between the wound cover and the wound.

The dressing embodiments disclosed herein can have a support member for positioning at least partially over a wound bed. FIG. 1 is an illustration of an embodiment of a wound dressing 100 having a support member 102 positioned over the wound W, a wound cover 106 (also referred to herein as a drape) sealingly positioned over the support member 102 into contact with skin surrounding the wound, and a conduit in communication with the substantially sealed space between the overlay 106 and the wound W. FIG. 2 is a front view of the embodiment of the support member of the dressing member embodiment 100 illustrated in FIG. 1. FIG. 3 is a side view of the embodiment of the dressing member 100, showing the support member 102 over a wound in a first state or at a first stage of healing. FIG. 4 is a side view of the embodiment of the dressing member 100 illustrated in FIG. 1, showing the support member 102 over a wound at a second state or in a second, more advanced stage of healing. In any embodiments or methods disclosed herein, the support member can be configured to be positioned within the wound bed so that the bottom portion of the support member (e.g., the bottom of the legs, in some embodiments) is positioned deep in the wound bed relative to the wound interface tissue. For example, in any embodiment herein, the bottom portion of the support member can be positioned so as to be at approximately the same level as or in contact with a deep fascia layer, and/or any other fascia or other tissue layer.

With reference to FIGS. 1-3, some embodiments of the support member 102 can have one or more legs (also referred to herein as a body portion) 114 attached to a top portion 116 (also referred to herein as a first portion) of the support member 102. In some embodiments, the top portion 116 of the support member 102 can be along an apex of the support member 102 and define a longitudinal axis A1 of the support structure. The legs 114 can be rotatably supported by the top portion 116 so that the legs 114 can rotate about axis A1 defined through the axial centerline of the top portion 116. As the wound closes as it heals, the legs 114 can rotate closer together (from the first state of FIG. 3 to the second state of FIG. 4) so that the closure of the wound W is not inhibited by the dressing 100. In some embodiments, the second state can merely result from the application of negative pressure on the dressing 100, wherein the rotatability of the legs 114 permits greater contraction of the wound under negative pressure as compared to a conventional dressing. In any embodiments disclosed herein, the support member can be configured such that the legs, panels, or other support portions configured to rotate or flex can rotate or flex about a plurality of axes, not just about one single axis. That also goes to say that any of the embodiments disclosed herein can be configured such that the primary mechanism for lateral contraction is through flexure, or bending of a hinge (such as a living hinge) positioned or adjacent to an apex of the support member. Therefore, in any embodiments disclosed herein, the support member can be configured to have a hinge (such as a living hinge) in place of any of the rotational components disclosed.

In some embodiments, the top portion 116 is an elongate member such as, but not limited to, a hollow rod or a hollow shaft. The top portion 116 of the support member 102 can have a plurality of longitudinal members, such as top portions 116a-116h illustrated in FIG. 1. Each of the top portions 116a-116h can be independently rotatable and can independently support one or more legs 114. The legs 114 can be supported in a cantilevered disposition by the top portions 116a-116h. The top portions 116a-116h can define an opening 118 axially therethrough, configured to receive a shaft or pin 122 configured to radially support the top portions 116a-116h. The top portions 116a-116h can be configured to rotate uninhibited about the shaft 122, thereby permitting the legs 114 to rotate about the shaft 122 and axis A1. The shaft 122 and the top portion (s) 116 can be formed from any suitable material, including stainless steel, titanium, a composite material, polymeric material (e.g. polyvinyl chloride, polystyrene, polypropylene), or other materials in some embodiments. The shaft in any embodiment herein can be rigid or can be flexible enough to permit the support member to flex or bend along a length thereof as a patient moves, or can be articulable or moldable to curve as needed to fit a patient's wound or patient movement. The legs 114 can be formed from any suitable material, including stainless steel, titanium, a composite material, polymeric material (e.g. polyvinyl chloride, polystyrene, polypropylene) or other materials in some embodiments. The legs 114 should be constructed to have sufficient strength to withstand the forces applied to them.

In some embodiments, the support member 102 can have any number of legs 114 appropriate for the size and type of wound to be treated. In the embodiment illustrated in FIG. 1, the support member 102 can have nine legs 114, with five legs on one side of the wound and four legs on the other side. In any of the embodiments disclosed herein, the support member 102 can have as few as three legs, from four to twenty or more legs 114, or from six to twelve legs. In any embodiment disclosed herein, the support member can be configured such that one or more of the legs, or in some embodiments approximately half of the legs, can be positioned to be on one side of a wound while one or more legs, or in some embodiments approximately half of the legs, can be positioned to be on the other side of the wound. Therefore, in some embodiments, a first set of legs can be positioned on one side of a wound while a second set of legs can be positioned on the other side of the wound.

The legs of the first set of legs can be positioned so as to define a first plane defined by the position of the legs of the first set of legs. The legs of the second set of legs can be positioned so as to define a second plane defined by the position of the legs of the second set of legs. The first and second plane can generally define an A-shape or A-frame, or an upside down V-shaped structure. In some embodiments, though not required to have independent movement, the legs of each group can move in and out of the respective plane due to the independent movement of each leg. Such independent angular adjustability, along with independent lengthwise adjustability in some embodiments as described below, can permit any of the support members herein to accommodate a wide ranging size of wounds and a wide ranging shape of wounds.

In any embodiments disclosed herein, the dressing 100 can be configured such that the first set of legs and the second set of legs of the support member 102 can define an angle therebetween, for example an acute angle, represented by A3 in FIG. 3. For example, the angle A3 may be approximately 56 degrees, or from 50 degrees or less to 70 degrees or more, or 90 degrees or more, or, in some embodiments and methods, to 120 degrees or more (or approximately 50 degrees or less to approximately 70 degrees or more, or approximately 90 degrees or more, or approximately 120 degrees or more), when positioned over a wound. Additionally, with reference to FIG. 4, in some embodiments, the dressing 100 can be configured such that the first and second sets of legs of the support member 102 can define an angle therebetween, represented by A4 in FIG. 4, of approximately 35 degrees, or from 0 degrees to 40 degrees or more, or from 20 degrees or less to 40 degrees or more (or approximately 0 degrees to approximately 40 degrees, or approximately 20 degrees or less to approximately 50 degrees or more), after negative pressure has been applied to the wound or after the wound has progressed to a more advanced stage of healing. In practice this angle can reduce to zero degrees where the legs (or panels as described below) touch or sit between each other. This may be particularly true where there is flexing of the legs under the forces exerted by the atmosphere on the structure.

In some embodiments, the dressing 100 or any other dressing disclosed herein can be configured such that an angle between the sets of legs 114 of the support member 102 can decrease by 20 degrees (or approximately 20 degrees) or more, or from 15 degrees or less to 50 degrees or more (or approximately 15 degrees or less to approximately 50 degrees or more), or can decrease by up to approximately 120 degrees or more, from a first ambient pressure state (represented by angle A3 in FIG. 3) to a second state (represented by angle A4 in FIG. 4) wherein negative pressure has been supplied to the dressing 100.

As shown in FIGS. 3 and 4, in some embodiments, one or more of the legs 114 can have pads 130 (which can be made from foam) positioned at an end 114a thereof or over an end thereof to provide a soft interface between the ends 114a of the legs 114 and the body of the patient. The pads 130 or any other similar or suitable cushions or members (such as foam caps or other end members) can be positioned over the contact edge or edges of any of the legs or edges of any of the frame embodiments disclosed herein. However, such pads 130 or other similar members are not required to be used with the embodiment illustrated in FIG. 3-4 or any other embodiments disclosed herein. Additionally, in any of the embodiments disclosed herein, the edges, legs, or other portions of the frame adjacent to the wound bed can be positioned on top of the foam member, or positioned over a flanged edge or within a channel formed in the foam member.

In some embodiments, the drape 106 or any other drape or wound cover disclosed herein can be a flat film type drape. The film in some embodiments can be folded in half and bonded or sealed along the sides thereof to form a triangular tent shape. In some embodiments, the drape can be custom molded into the desired shape, which can be a triangular tent shape. In some embodiments the tent-drape may be fabricated from plastic film panels and heat welded together. Suitable materials include films made from polyurethane, Opsite film, polyester, polyethylene etc. Some drapes may be translucent in nature to allow visibility of the interior of the dressing. In some embodiments, the tent-drape will have no adhesive. Alternatively the tent may have an adhesive strip covered with a removable protector for adhering it to the wound periphery. Alternatively the tent is sealed to the patient using adhesive drapes or tape, e.g. Opsite or a RENASYS transparent film dressing.

As shown in FIG. 4, in some embodiments, adhesive 134 can be positioned over all or a portion of the wound facing side of the drape 106. The adhesive 134 can be an annular ring of adhesive forming a ring around the wound, or can be coated over the entire wound facing surface of the drape 106. Not having adhesive on an inside portion of the drape 106 can prevent the drape 106 from sticking together when the sides of the drape 106 comes into contact with one another.

In some embodiments, a foam member 112 or other wound packing member can be positioned in the wound bed. The support member 102 can collapse or close laterally around the wound packing material or foam (i.e., the sides of the support member 102, which can comprise in some embodiments legs 114, can be drawn together), thereby causing the packing material or foam to be pushed up into the space 126 inside the support member 102, as is illustrated in FIG. 4.

In any of the embodiments disclosed herein, the wound packing member can be an inflatable member. Some embodiments of the dressing may have a fluid (for example, without limitation, air) inflatable bladder in addition to any other components of the dressing, including foam, gauze, silicone, and any combination of the foregoing including a matrix formed from silicon and/or foam. One embodiment of an inflatable member may be pumped up before the vacuum is applied. The air or fluid in the inflatable member can then be controllably removed with a pump and/or valve to control the amount of contraction on the wound. This is advantageous for compartment syndrome cases, especially abdominal compartment cases, to relieve pressure on the organs, as too much closure at initial application could recreate this internal pressure on the organs.

Compartment syndrome can occur when excessive pressure builds up inside an enclosed space in the body. Excessive pressures in the abdominal compartment, for example, can impede the flow of blood to and from the affected tissues, bodily organs, or even the lower extremities if excessive pressure is exerted on the abdominal aorta. The pressure buildup within the abdominal compartment can be the result of excessive fluid buildup in the abdominal compartment, in addition to or alternatively as a result of the forces exerted on the abdominal region from the application of negative pressure wound therapy to the abdominal compartment.

Such excessive pressure can cause permanent injury or damage to the tissues, organs (such as the liver, bowels, kidneys, and other organs), and other body parts affected by the reduction of blood flow. Therefore, preventing the buildup of excessive pressures in the abdominal compartment is beneficial for the treatment of abdominal injuries.

Internal pressure may also be measured and/or monitored via the gastrointestinal system (including colonically), or via the uterus. In some arrangements, for example, the internal pressure may be measured by inserting a catheter into the patient's bladder. Aortic blood pressure can also be monitored using techniques known in the field. For limb-based compartment syndrome, the internal pressure can be measured by a needle inserted into the affected limb, and preferably, the pressure measured there should be within 20-30 mmHg of the patient's diastolic blood pressure. The clinician may also monitor for a pulse distal of the affected extremity.

In addition to any of the foregoing methods or devices for measuring internal pressure, or any combination of such, in some embodiments, any of the negative pressure wound therapy dressing components disclosed herein can be configured to support or contain one or more pressure sensors configured to permit a clinician to monitor the internal pressure within the compartment, wound cavity, or abdominal cavity. For example, one or more pressure sensors can be added to the dressing components, including without limitation positioning one or more pressure sensors on the surface of and/or inside any inflatable bladder embodiment disclosed herein that can be positioned in the abdominal cavity. The pressure sensors can be supported on, embedded within, or be integral with an outer and/or inner surface of any inflatable bladder embodiments disclosed herein, and can be used to monitor the pressure exerted on the inflatable bladder from the adjacent tissues and organs within the abdominal cavity to alert the patient or caregiver when a threshold or potentially harmful pressure is present within the abdominal cavity.

Additionally or alternatively, one or more pressure sensors can be positioned on or supported by a portion of any wound packing or silicone matrix components positioned within or adjacent to the wound cavity, or embedded within a portion of the matrix and/or the dressing overlay or cover, including being supported by the overlay itself, and/or any conduit components of the dressing. The pressure sensors can therefore be positioned on, supported by, or embedded within any combination of the dressing components disclosed herein.

Furthermore, in addition or alternatively to any of the sensor positions located herein, one or more pressure sensors can also be positioned adjacent to one or more of the organs in the cavity being treated, for example the bladder, one or more kidneys, and/or any other organs or proximally located tissue surfaces. Some embodiments can have one or more pressure sensors supported by or on or embedded within the wound packing layer or matrix, one or more pressure sensors supported by or on or embedded within one or more of the organs or tissue layers in the cavity, and one or more pressure sensors supported by or on or embedded within one or more inflatable bladders positioned within the wound cavity.

Monitoring the pressure in each of these three locations can permit the caregiver to optimize or control the level of negative pressure applied to the wound cavity, optimize or control a level of inflation or pressure of the inflatable bladder, and/or monitor a level of pressure exerted on one or more organs, tissue layers, blood vessels, or other body parts affected by the closure pressures. A caregiver can then adjust a level of pressure in the inflatable bladder by either adding fluid to the bladder or releasing fluid from within the bladder to a receptacle or container positioned outside the body, adjust a level of negative pressure exerted on the wound cavity, and/or adjust any other closure forces applied to the wound to either increase or decrease the closure forces.

A clinician may monitor the internal pressure as vacuum is slowly increased to the wound dressing, or as air is slowly released from the inflatable member. In one embodiment, bladder pressure is controlled below 40 mm Hg. In some embodiments, the measurement of internal pressure and control of the vacuum and air release can be controlled automatically. This way as the oedema decreases the wound can be slowly closed further over, for example, a period of hours to days (e.g., closure by seven days). It will be appreciated that systems can be employed where the vacuum can be slowly applied with pressure feedback being provided based on vital signs of the patient.

Figure 22A:
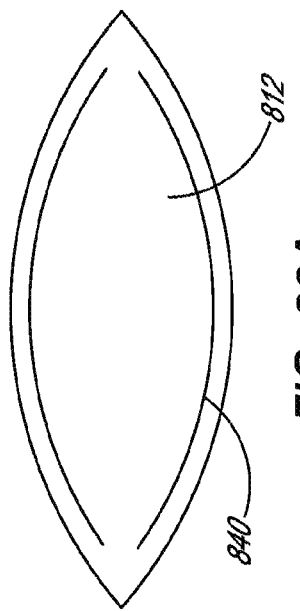
FIG. 22A is a top view of foam that can be used in some embodiments of the present disclosure.
Figure 22B:
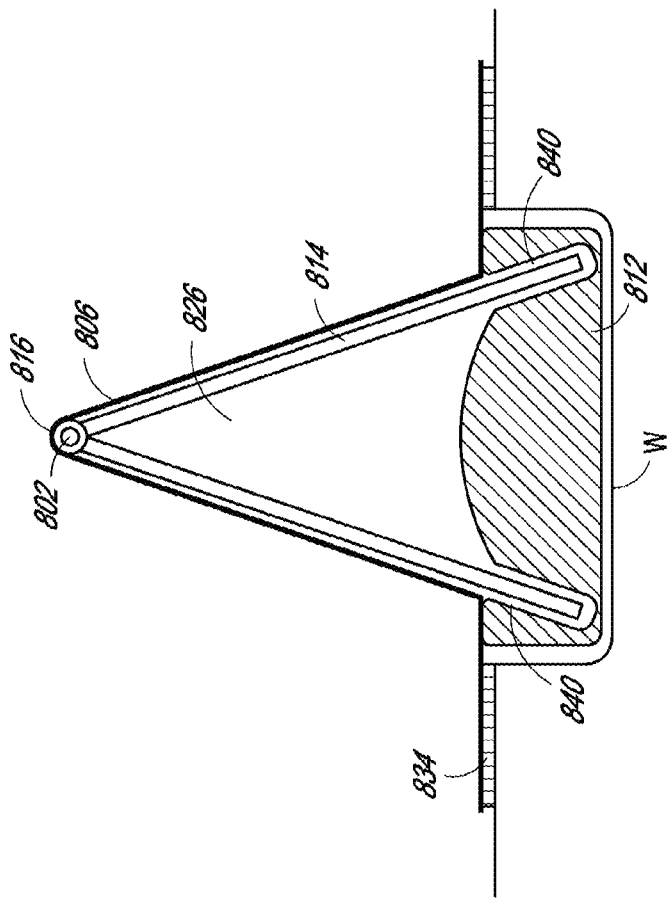
FIG. 22B is a side view of the embodiment of the dressing member illustrated in FIG. 22A, showing the support member placed into slots of the foam of FIG. 22A.
Figure 22C:
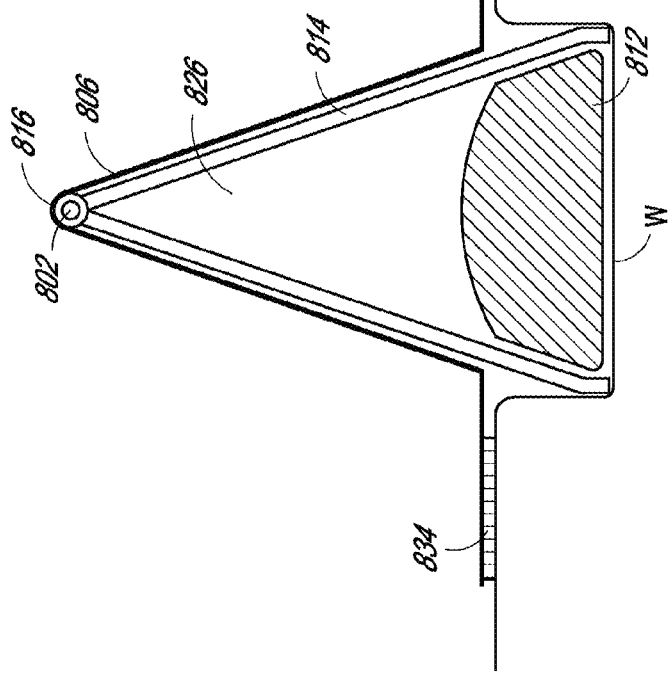
FIG. 22C is a side view of another embodiment of a dressing member.

In some embodiments the legs 814 are positioned inside the wound edges so that the legs penetrate to almost the bottom of the wound. Some embodiments and methods can have the legs 814 completely to the bottom of the wound so as to be adjacent to or in contact with all of the tissue layers in the wound interface. This may be accomplished in one embodiment by providing slits in the foam. FIG. 22A illustrates one embodiment of foam 812 having a generally elongated or oval shape (some embodiments can be cut to this shape) to approximate the wound to be treated. Though not used in all embodiments, one or more slits 840 may be provided along lateral edges of the foam (e.g., approximately ¼ inch from the wound edge). As shown in FIG. 22B, these slits 840 may receive the legs or panels 814 of the support member 802. The slits advantageously help to hold the legs in place while the tent and/or sealing drapes are applied. Similar to the embodiment of FIG. 4, the support member 802 also includes a top portion 816, and may be covered with a drape 806 having adhesive 834 for sealing the drape to skin surrounding the wound. When negative pressure is applied, the legs 814 (or panels as described below) close the space 826, though this closure may be partially restricted by the positioning of the legs in the slits 840. In some embodiments, the legs 814 of the support member can be positioned directly against all of the tissue layers of the wound interface, as illustrated in FIG. 22C.

The size of each component or feature of each support member can be adjusted based on the size of the wound being treated and other details of the application. With reference to FIGS. 5-6, which are a side view and a front view of a top portion 116 and an arm 114, in some embodiments, the length L1 of the arms can be 3 inches or approximately 3 inches, or from 1 inch to 5 inches (or approximately 1 inch or less to approximately 5 inches) or more in length, or from 2 inches to 4 inches (or approximately 2 inches to approximately 4 inches) in length. The legs 114 of the support member 102 can vary across the length of the support member. The thickness T1 of the arms can be 0.1 inch or approximately 0.1 inch, or from 0.05 inch (or approximately 0.05 inch) or less to 0.2 (or approximately 0.2 inch) or more. The width W1 of the arms can be 0.13 inch (or approximately 0.13 inch), or from 0.05 inch (or approximately 0.05 inch) or less to 0.2 inch (or approximately 0.2 inch) or more. The width W2 of some embodiments of the top portion 116 can be 0.8 inch (or approximately 0.8 inch), or from 0.25 inch (or approximately 0.25 inch) or less to 1.5 inch (or approximately 1.5 inch) or more. The height H1 of the top portion 116 can be 0.19 inch (or approximately 0.19 inch), or from 0.1 inch (or approximately 0.1 inch) or less to 0.3 inch (or approximately 0.3 inch) or more.

In some embodiments, the legs 114 can have a circular cross-section such that the width W1 and the thickness T1 will be diameters and will be approximately the same. However, the legs 114 or any other legs disclosed herein can have any suitable cross-sectional shape, including round, square, triangular, rectangular, hexagonal, hollow, solid, or otherwise. In some embodiments, where the top portion 116 can have a circular cross-section, the height H1 will be a diameter. However, the top portion 116 or any other top portion disclosed herein can have any suitable cross-sectional shape, including round, square, triangular, rectangular, hexagonal, or otherwise. The lateral width Wsm of the support member 102 can be approximately 7 inches, or from approximately 3 inches or less to approximately 12 inches or more. The thickness or width W4 of the top portion 116 can be approximately 0.19 inch, or from approximately 0.1 inch or less to approximately 0.3 inch or more. Where the top portion 116 or any other top portion disclosed herein has a round cross-sectional shape, as in the embodiment illustrated in FIG. 1 such that width W4 is a diameter, the width W4 will be approximately the same as the height H1.

Additionally, the arms 114 can be spaced apart from one another at any desired length or interval. For example, without limitation, the spacing S1 (illustrated in FIG. 2) between the arms 114 of the support member 102 can be approximately 0.8 inch (center of arm 114 to center of arm 114), or from approximately 0.5 inch or less to approximately 1.5 inches or more (center to center). Any of the embodiments of the support members disclosed herein can have any of the foregoing dimensions, though not required.

Additionally, with reference to FIG. 7, while the support member 102 can be configured such that the arms 114 can rotate 360 degrees around the axis A, in some arrangements, the support member 102 can be positioned over a wound in a position such that the arms 114 form an angle A1 relative the body surface that is approximately 62 degrees, or from 50 degrees or less to 80 degrees or more, or from 50 degrees or less to 120 degrees or more (or approximately 50 degrees or less to approximately 80 degrees or more, or approximately 50 degrees or less to approximately 120 degrees or more). As used in this disclosure, unless otherwise specified, the term approximately, as applied to measures of length, weight, time, efficiency rates, percentages, and other similar measures, is meant to refer to a range of plus or minus 15% of the stated value.

Figure 8A:
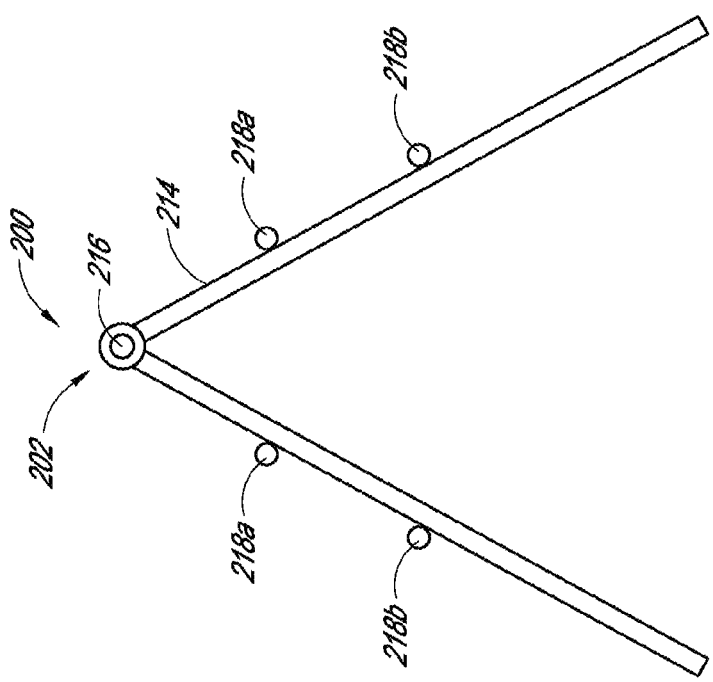
FIG. 8A is a side view of another embodiment of a support member.
Figure 8B:
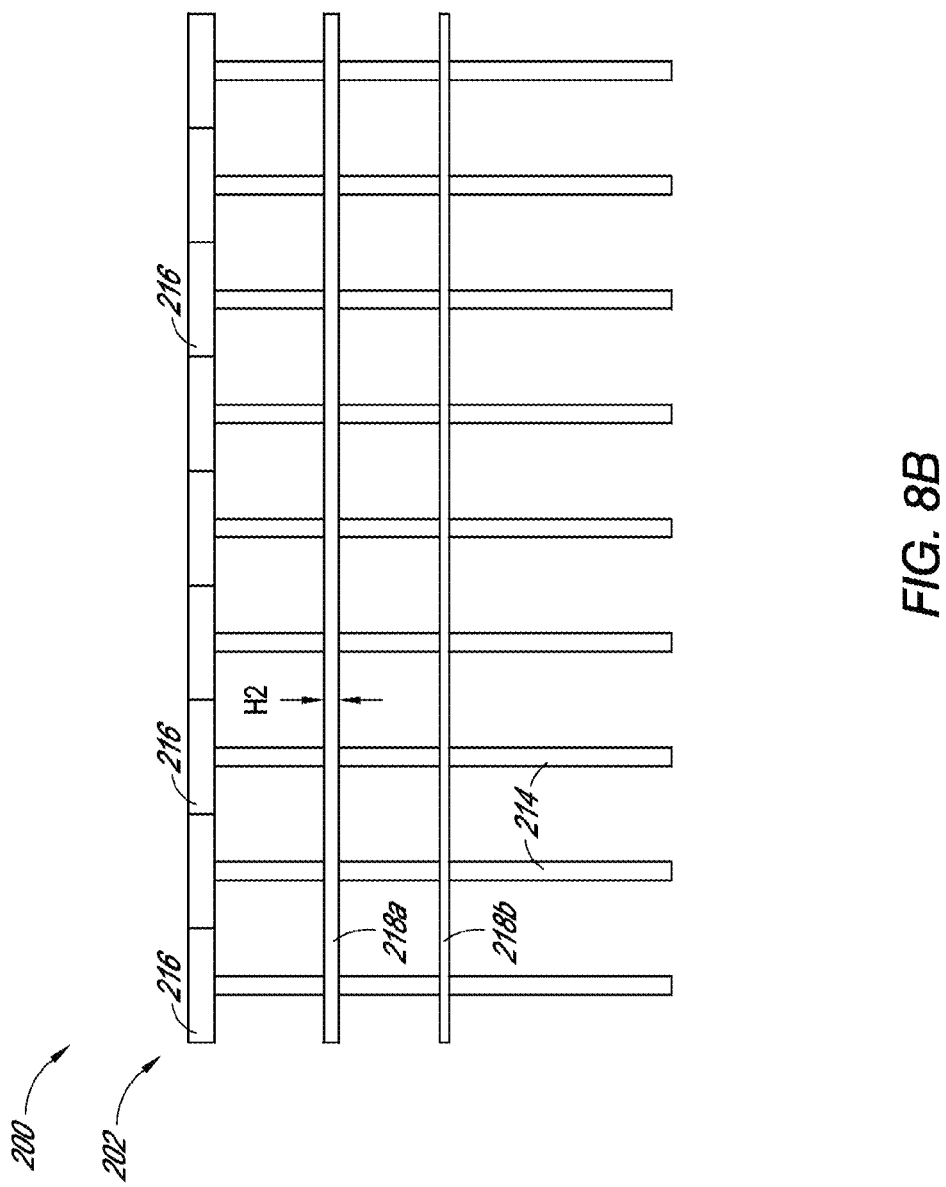
FIG. 8B is a front view of the embodiment of the support member illustrated in FIG. 8A.

FIGS. 8A and 8B are a side view and a front view, respectively, of another embodiment of a dressing 200 having a support member 202. Any embodiments of the dressing 200 and the support member 202 can have any of the features, materials, sizes, shapes, components, or other details of any of the other embodiments disclosed herein, such as without limitation the dressing 100 and support member 102. Additionally, in some embodiments, the support member 202 can have one or more cross supports (also referred to herein as connectors) 218 coupled with one or more of the arms 214. The cross supports can aid with closure of the wound by stopping or inhibiting the drape on each side of the frame from meeting or touching in the middle of the support member as quickly. For example, without limitation, some embodiments of the support member 202 can have a first cross support 218a and a second cross support 218b on each side of the support member 202. Some embodiments have only one cross support 218 on each side of the support member 202. In some embodiments, one or more of the cross supports 218 can have a height H2 (or diameter, if the cross-sectional shape is round) of approximately 0.13 inch, or from approximately 0.05 inch or less to approximately 0.2 inch or more.

Figures 1, 9:
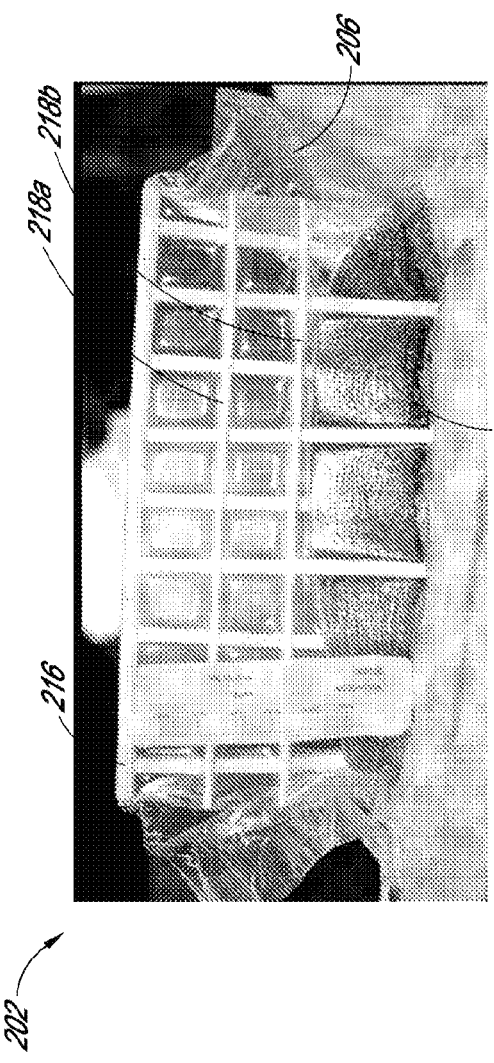
Figures 2, 9:
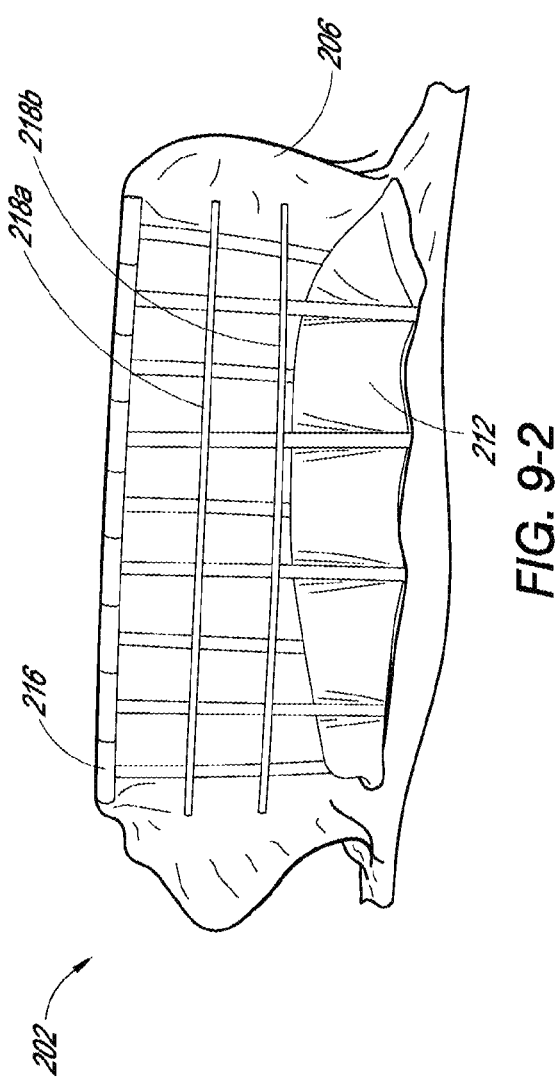

FIG. 9 is a front view of an embodiment of a dressing 200 having the support member 202 illustrated in FIG. 8, showing the dressing applied to a wound model after a therapeutic level of reduced pressure has been applied to the wound. Additionally, as illustrated, the dressing can have a drape or cover member 206 configured to cover the wound, and a wound filler 212 positionable beneath the cover member 206 between the opposing arms 214 of the support member 202. In any embodiments disclosed herein, including without limitation the embodiment illustrated in FIG. 9, the wound filler can comprise at least one of foam, gauze, a deflatable hollow member, a sealed enclosure, a sealed enclosure having a collapsible structure therein, and any combination of the foregoing. Additionally, in any embodiments disclosed herein, including the dressing 200, the filler can be a collapsible wound filler configured to be more flexible and, hence, more collapsible, in a lateral direction than in a vertical direction.

Figure 10:
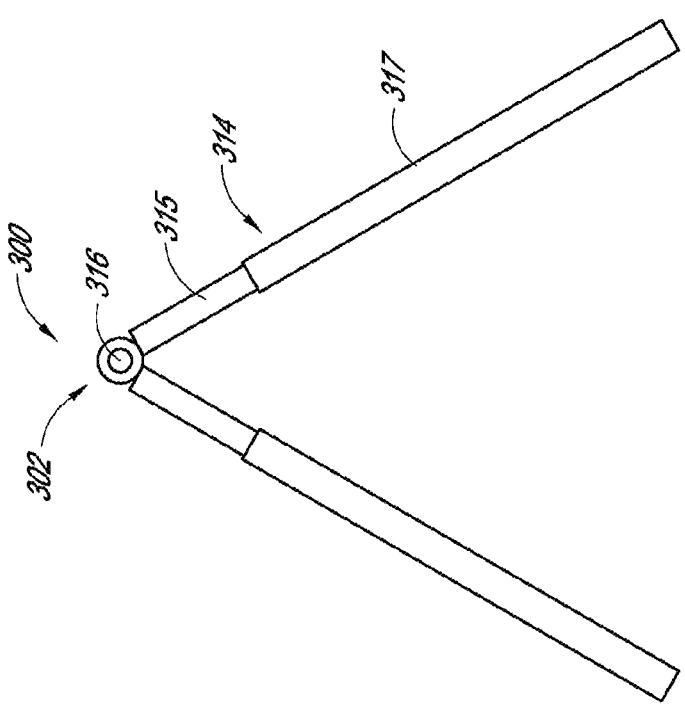
FIGS. 10 and 11 are a side view and a front view, respectively, of another embodiment of a dressing having a support member.
Figure 11:
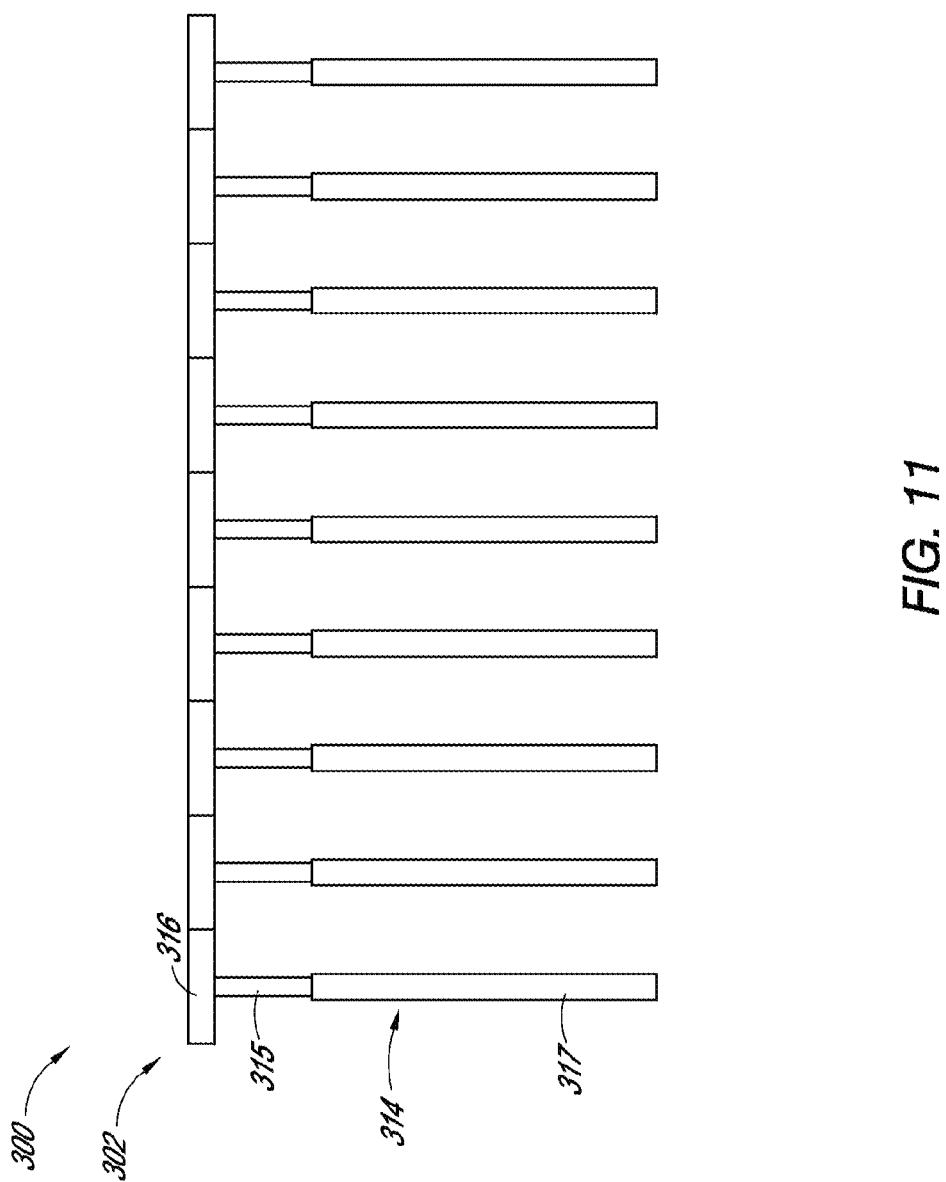

FIGS. 10 and 11 are a side view and a front view, respectively, of another embodiment of a dressing 300 having a support member 302. Any embodiments of the dressing 300 and the support member 302 can have any of the features, materials, sizes, shapes, components, or other details of any of the other embodiments disclosed herein, such as without limitation the dressings 100, 200 and support members 102, 202. Additionally, in some embodiments, the support member 302 can have one or more or two or more adjustable length arms 314. The adjustable length arms 314 can have a first or inner arm portion 315 coupled with the top portion 316 and a second or outer arm portion 317 that is adjustable relative to the first arm portion 315. In some embodiments, the second arm portion 317 can be independently slideable relative to the first arm portion 315 so that the length of the arm 314 can be adjusted to accommodate a wide ranging variety and size of wounds. The support member 302 can also have one or more cross supports thereon, such as the cross supports 218 illustrated in FIGS. 8, 9A, and 9B.

Figure 12:
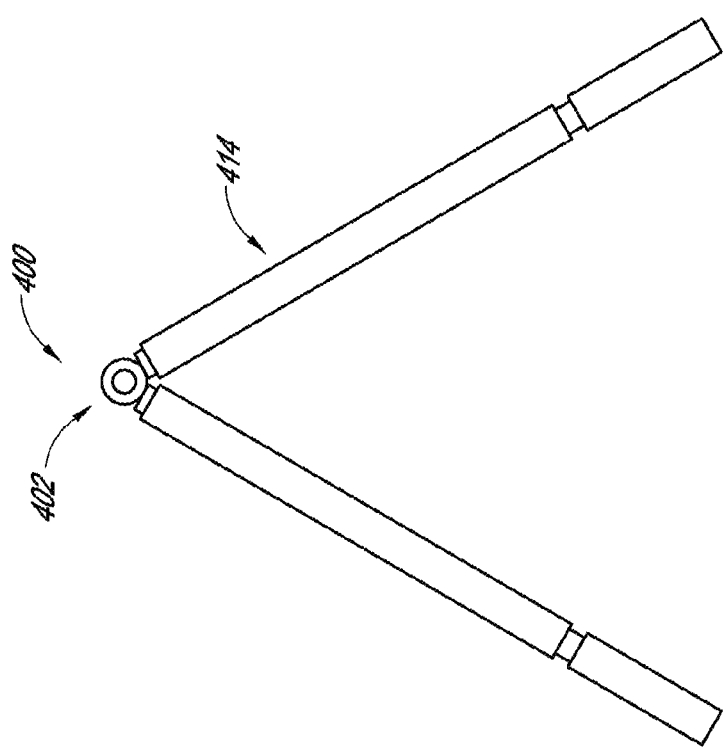
FIGS. 12 and 13 are a side view and a front view, respectively, of another embodiment of a dressing having a support member.
Figure 13:
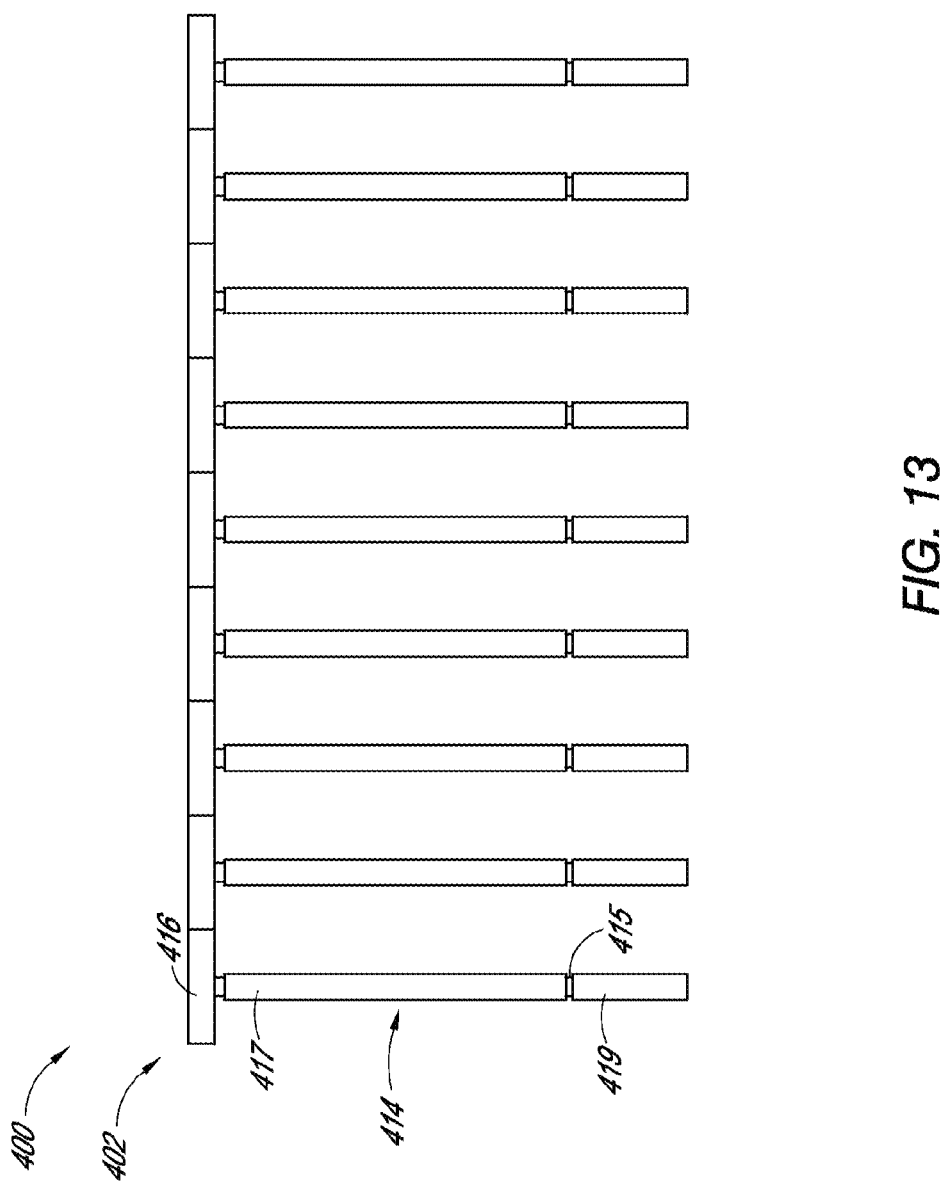

FIGS. 12 and 13 are a side view and a front view, respectively, of another embodiment of a dressing 400 having a support member 402. Any embodiments of the dressing 400 and the support member 402 can have any of the features, materials, sizes, shapes, components, or other details of any of the other embodiments disclosed herein, such as without limitation the dressings 100, 200, 300 and support members 102, 202, 302. Additionally, in some embodiments, the support member 402 can have one or more or two or more adjustable length arms 414. The adjustable length arms 414 can have a first or inner arm portion 415 coupled with the top portion 416, a second or long outer arm portion 417, and a third or short outer arm portion 419. The second and/or third arm portions 417, 419 can be adjustable relative to the first arm portion 415. In some embodiments, the second arm portion 417 can be independently slideable relative to the first arm portion 415 so that the length of the arm 414 can be adjusted to accommodate a wide ranging variety and size of wounds. The support member 402 can also have one or more cross supports thereon, such as the cross supports 218 illustrated in FIGS. 8 and 9.

It is also envisaged, for example in embodiments such as those illustrated in FIGS. 10-11 and 12-13, that once the wound has contracted fully and is stable (e.g., oedema has diminished), the amount of negative pressure acting at the apex of the support member 402 may be minimal. This may thus permit a portion of the leg and/or top portions from either embodiment to be removed from a part of the leg that remains adjacent the wound, such that the structure can be folded flat and parallel to the wound plane on the patient whilst still maintaining vacuum. This may allow greater patient comfort whilst not requiring a visit to the operating room. For example, in FIG. 10, the outer arm portion 317 may remain in the wound while the inner arm portion 315 and top portion 316 are removed from the outer arm portion 317 and folded flat Likewise, with reference to FIG. 12, the short outer arm portion 419 and/or inner arm portion 415 may remain in the wound while the long outer arm portion 417 (and/or the inner arm portion 415) and top portion 416 are removed therefrom and folded flat.

Figure 14:
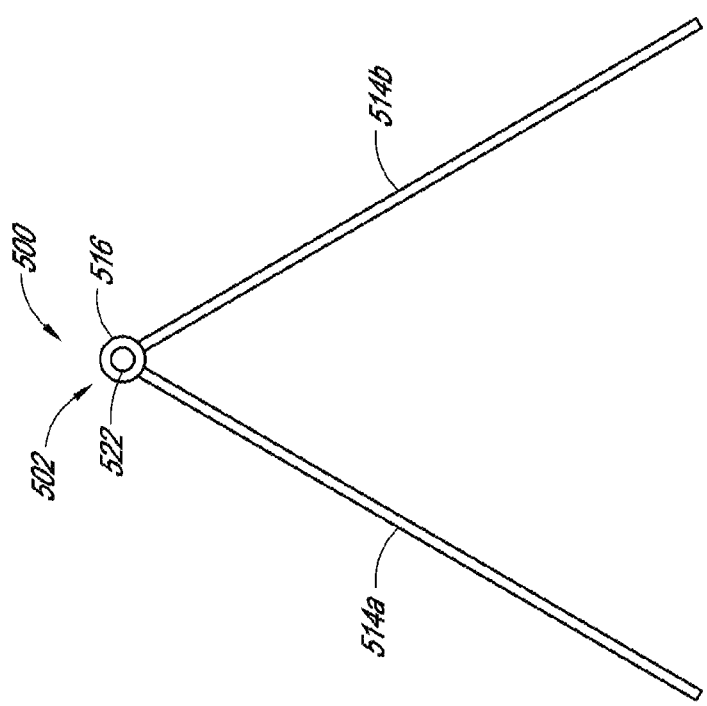
FIGS. 14 and 15 are a side view and a front view, respectively, of another embodiment of a dressing having a support member.
Figure 15:
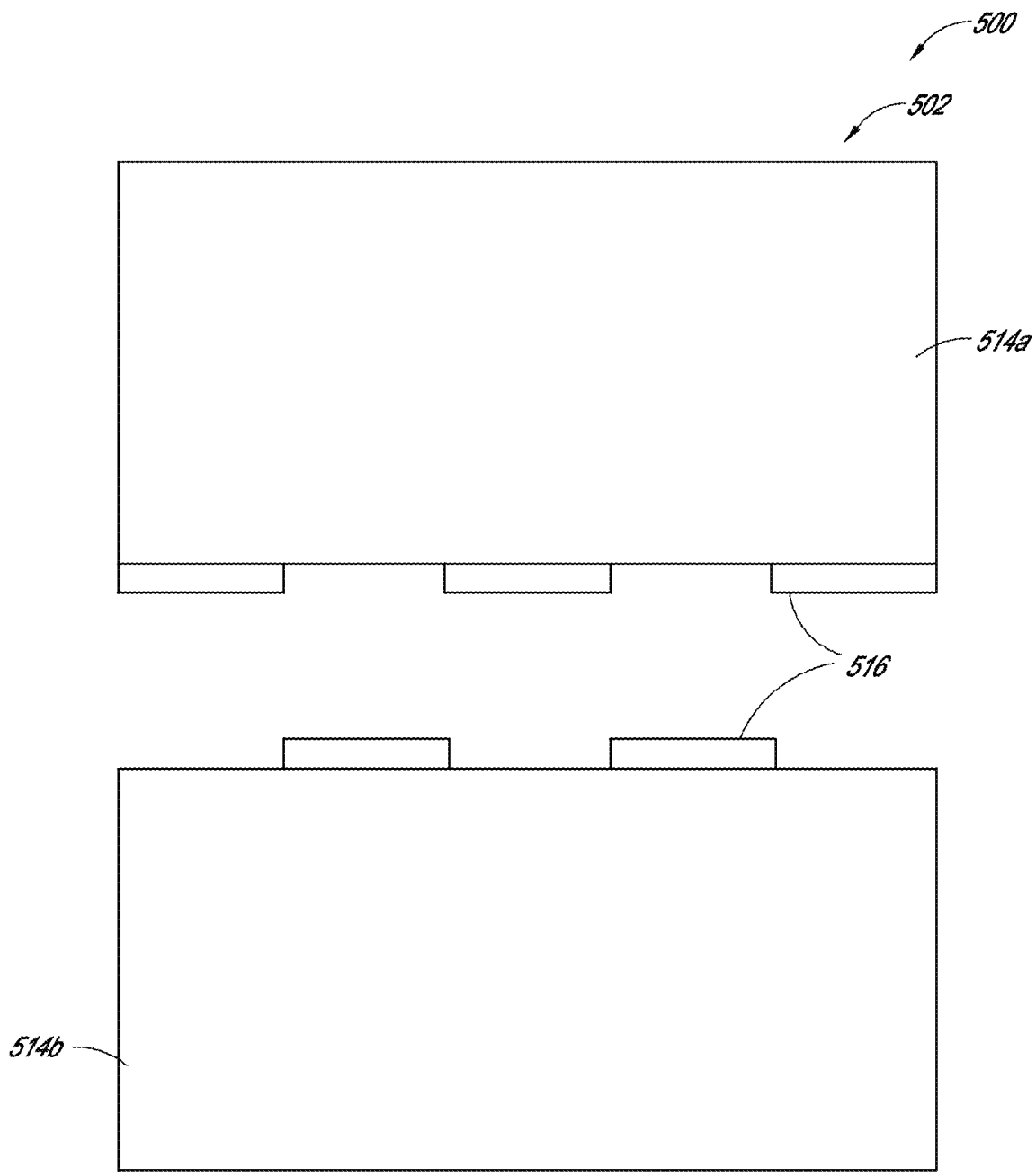

FIGS. 14 and 15 are a side view and a front view, respectively, of another embodiment of a dressing 500 having a support member 502. Any embodiments of the dressing 500 and the support member 502 can have any of the features, materials, sizes, shapes, components, or other details of any of the other embodiments disclosed herein, such as without limitation the dressings 100, 200, 300, 400 and support members 102, 202, 302, 402. In some embodiments, the support member 502 can have one or more or two or more boards or panels 514 in place of the arms of other embodiments. For example, without limitation, the support member 502 can have a first panel 514*a* have a top portion 516 and second panel 514*b* having a top portion 516. The top portion of the first panel 514*a* can be connected to the top portion of the second panel 514*b* using a shaft 522 advanced through the opening 518 formed in each top portion. As used in this disclosure, the boards, panels, legs or arms described above can collectively be referred to as different embodiments of side supports, and would include other configurations as well.

The panels 514 can be approximately 6 inches wide, or can be from 1 inch to 5 inches wide, or from 5 to 10 inches wide (or from approximately 1 inch wide to approximately 4 inches wide, or from approximately 4 inches wide or less to approximately 10 inches wide) or more. The top portions 516 can be approximately 1.2 inches wide, or from 0.5 inch wide to 2 inches wide (or approximately 0.5 inch wide or less to approximately 2 inches wide) or more. Narrower panels or narrow top portions can permit greater articulation or flexibility in the support member.

Figure 16:
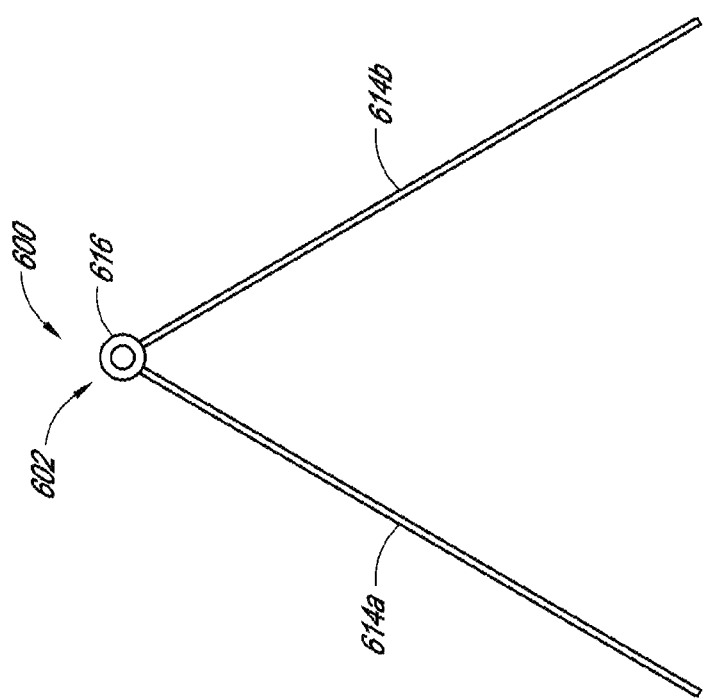
FIGS. 16, 17, and 18 are a side view, top view, and an assembled top view, respectively, of another embodiment of a dressing having a support member.
Figure 17:
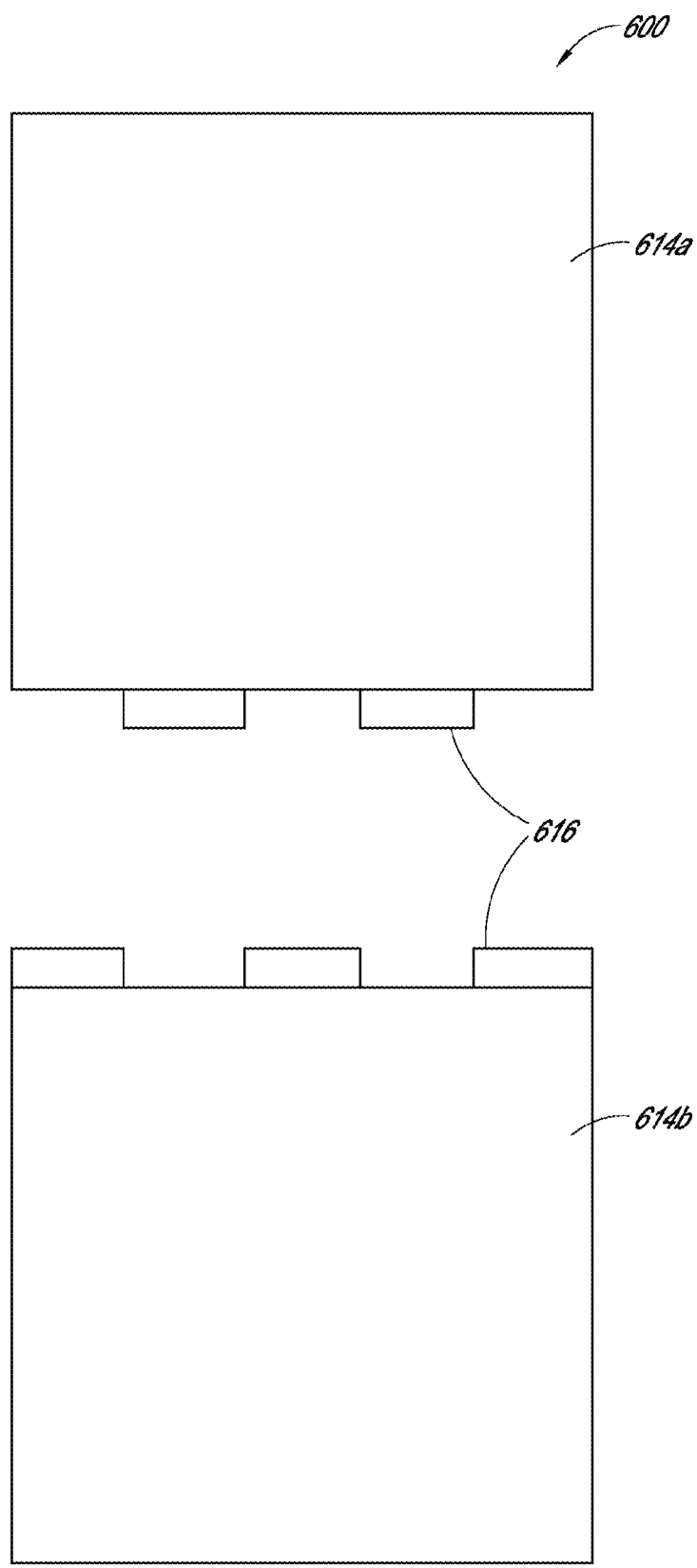
Figure 18:
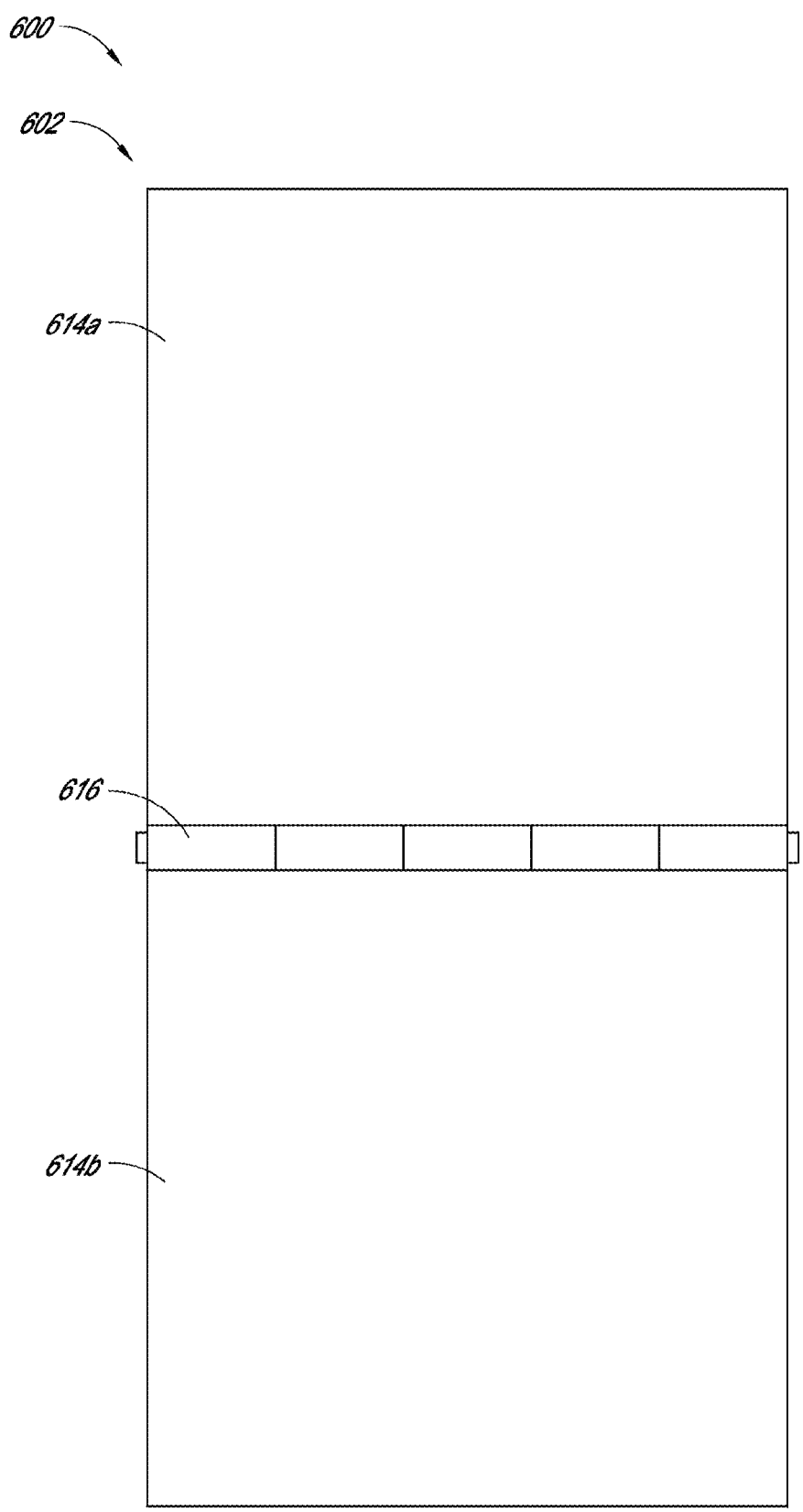

FIGS. 16 and 17 are a side view and a top view, respectively, of another embodiment of a dressing 600 having a support member 602. FIG. 18 is a top view of dressing 600 in an assembled condition. Any embodiments of the dressing 600 and the support member 602 can have any of the features, materials, sizes, shapes, components, or other details of any of the other embodiments disclosed herein, such as without limitation the dressings 100, 200, 300, 400, 500 and support members 102, 202, 302, 402, 502. With reference to FIGS. 16 and 17, in some embodiments, the panels 614 of the dressing 600 can be approximately 3 inches wide, or can be from approximately 2 inches wide or less to approximately 5 inches wide or more. The top portions 616 can be approximately 0.5 inch wide, or from approximately 0.25 inch wide or less to approximately 1 inch wide or more.

In any of the embodiments disclosed herein, the drape or wound cover can be positioned on the outside of the support member, as illustrated in FIGS. 1 and 3. Alternatively, in any of the embodiments disclosed herein, the drape or wound cover can be positioned on the inside of the support member, as is illustrated in FIG. 19, which is a side view of another embodiment of a dressing 700. In some embodiments, one or more connectors 707 can be coupled with the drape 706, the connectors 707 being configured to couple the drape 706 with the arms 714 (or boards of dressing 500 or 600). For example and without limitation, the connectors 707 can be loops configured to pass around an outside surface of the arms 714 so that the drape 706 is positioned on the inside of the arms 714.

Figures 1, 20B:
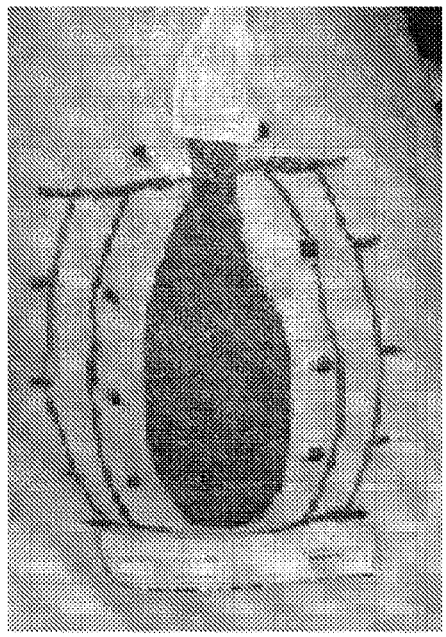
Figures 2, 20B:
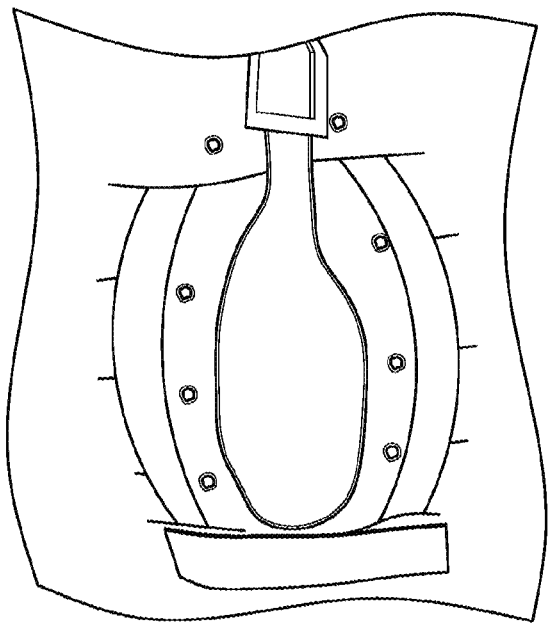
Figures 1, 20A:
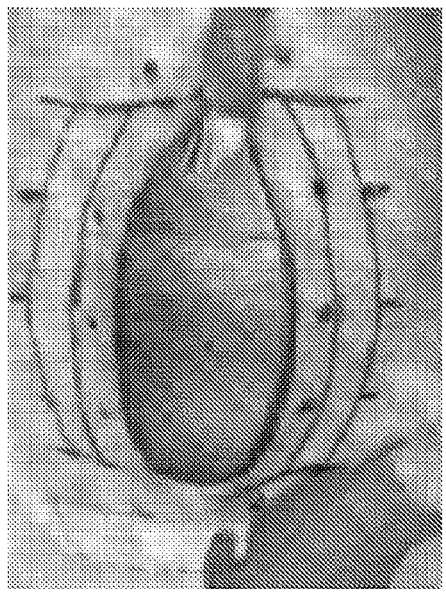
Figures 2, 20A:
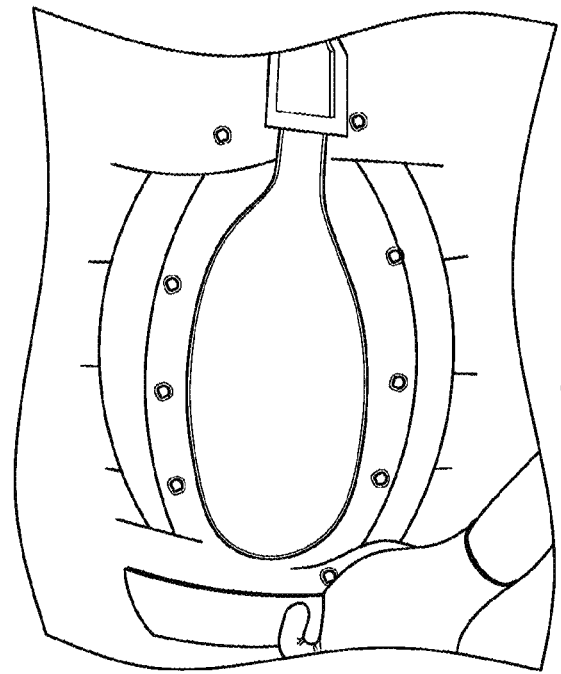
Figures 1, 21B:
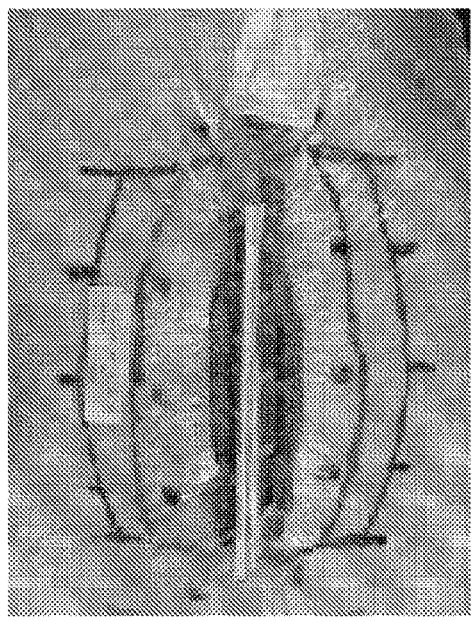
Figures 2, 21B:
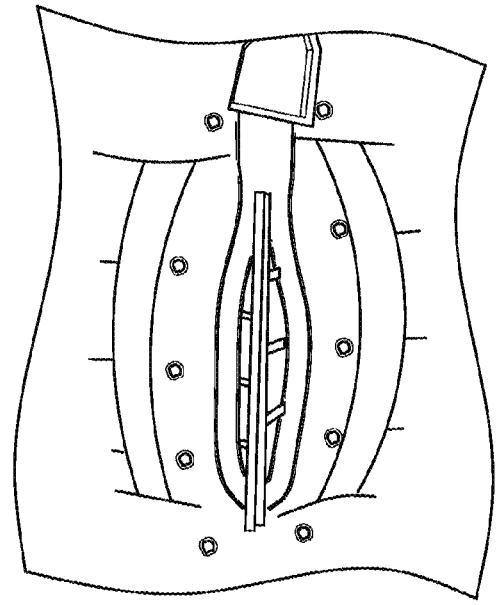
Figures 1, 21A:
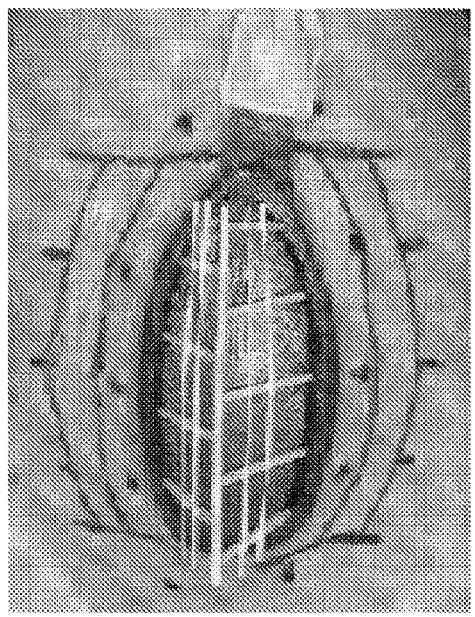
Figures 2, 21A:
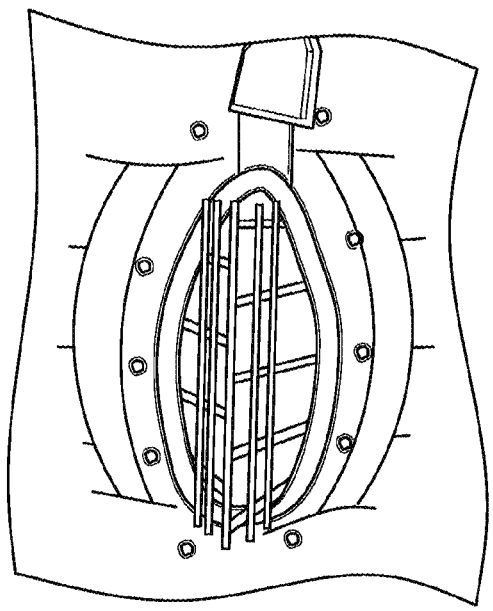

FIG. 20A is a photograph of a wound with foam inserted into the wound, and a drape applied over the foam and wound. A foam bridge is used to attach the drape to a vacuum source (e.g., a RENASYS EZ pump). FIG. 20B is a photograph of a wound with a conventional dressing thereon after the application of reduced pressure. FIG. 21A is a photograph of a wound with an A-frame dressing (such as, without limitation, dressing 100 or dressing 200) thereon prior to the application of reduced pressure. FIG. 21B is a photograph of a wound with an A-frame dressing (such as, without limitation, dressing 100 or dressing 200) thereon after the application of reduced pressure. In FIGS. 21A and 21B, the foam may have slits as described with respect to FIGS. 22A and 22B.

The minimal closure observed with negative wound pressure applied using the standard abdominal kit can be seen in FIG. 20, with FIG. 20A showing the wound on a tissue model prior to the vacuum being applied and FIG. 20B showing the wound on a tissue model after the vacuum has been applied. From Table 1 it can be seen that the application of the vacuum using the conventional dressing decreased the area of the wound by 25%.

In FIG. 21, the same wound can be seen with an embodiment of the dressing 200 having cross bars on the support member being used to increase the closure of the wound. FIG. 21A shows the wound with an embodiment of the dressing 200 having cross bars on the support member before the vacuum was applied. FIG. 21B shows the wound with an embodiment of the dressing 200 having cross bars on the support member after the vacuum has been applied. It can be seen from the photographs that the wound has closed quite significantly with the use of the embodiment of the dressing 200 illustrated in FIG. 21. As stated in Table 1, the closure of the wound using the embodiment of the dressing 200 illustrated in FIG. 21 is approximately 56%.

TABLE 1

Calculations from Testing Carried Out in a Tissue Model

| Tested Device | Vacuum Status | Area (mm²) | Percentage Difference |
|---|---|---|---|
| Black Foam | Off | 167 | 25 |
|  | On | 126 |  |
| Improved dressing according to some embodiments of the present disclosure having cross bars | Off | 190 | 56 |
|  | On | 84 |  |

Figures 1, 23A:
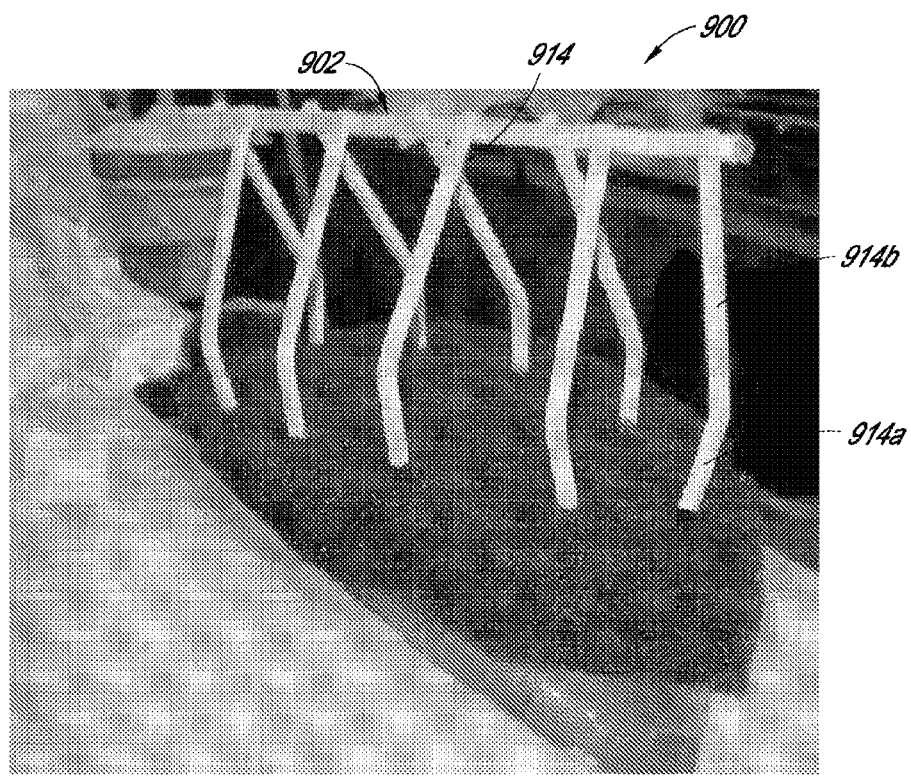
Figures 2, 23A:
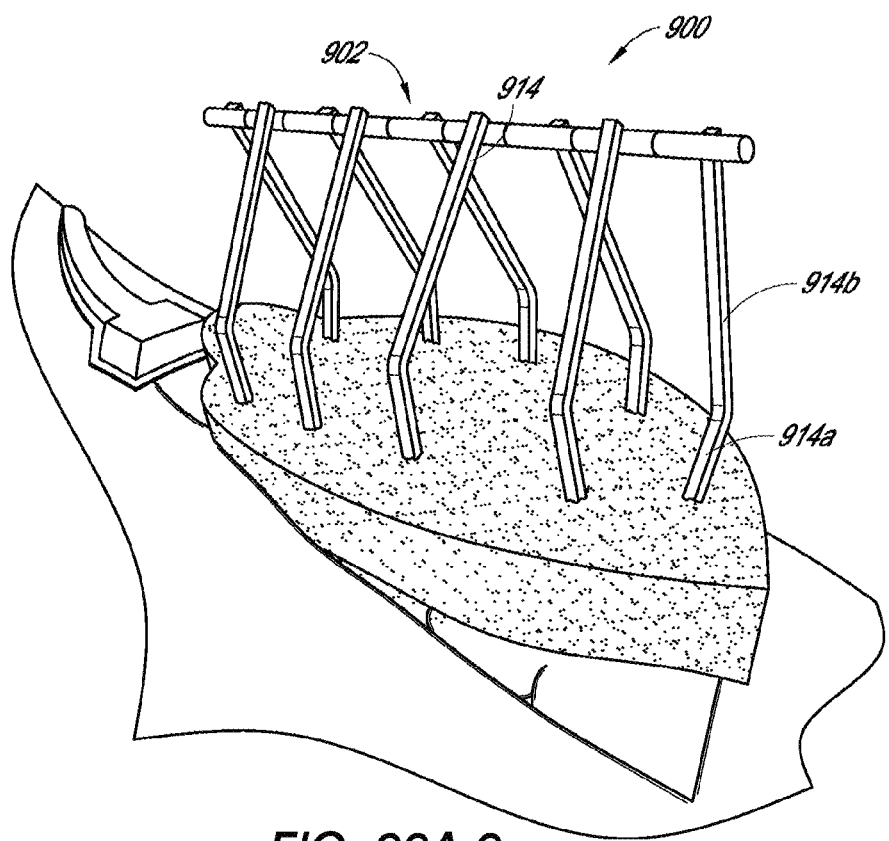
Figures 1, 23B:
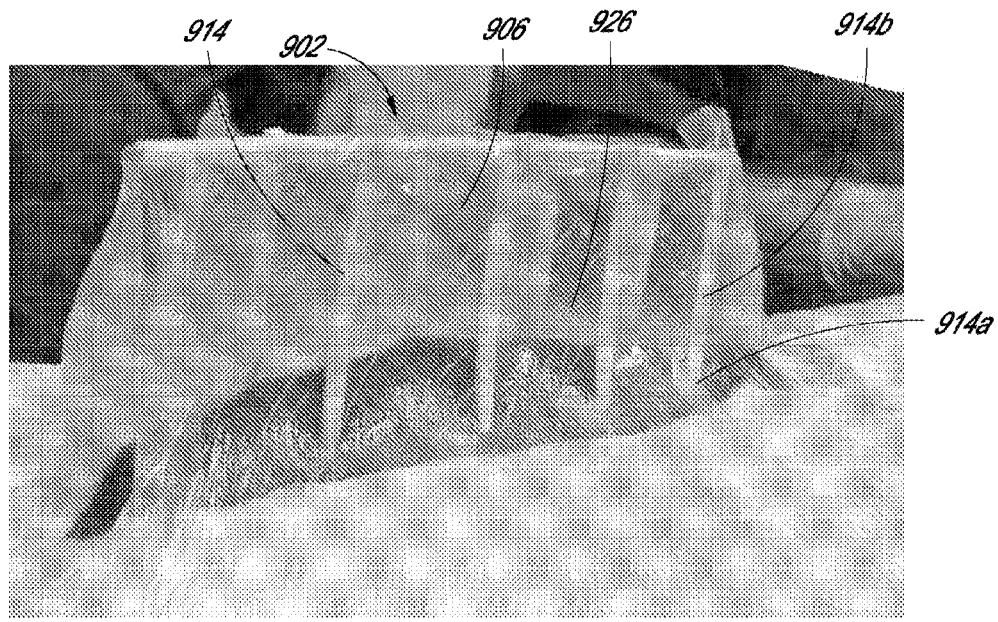
Figures 2, 23B:
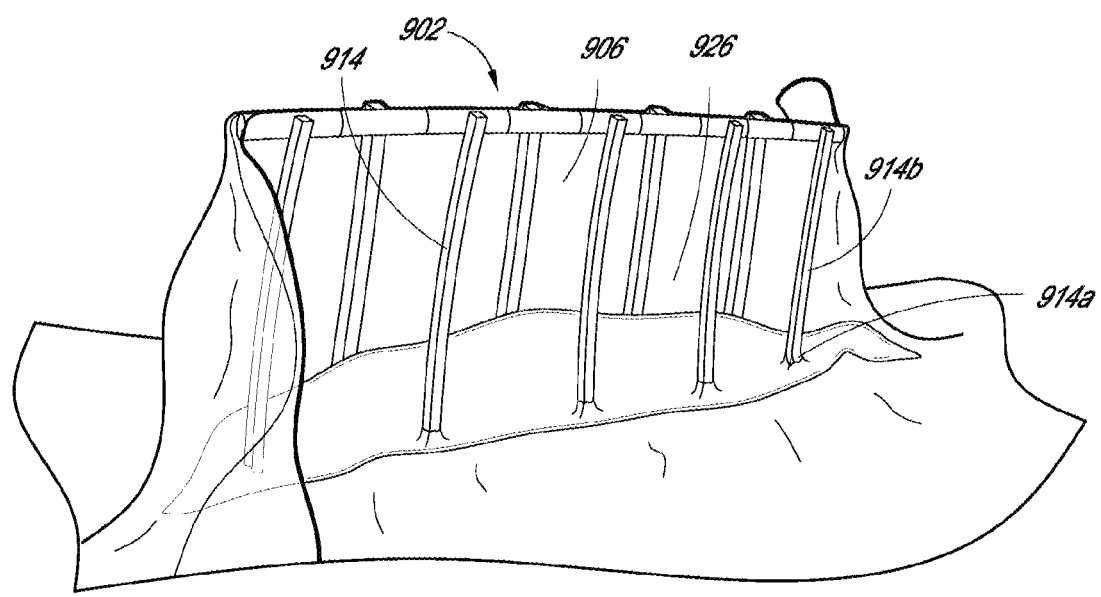

FIG. 23A is an isometric illustration of another embodiment of a wound dressing 900 having a support member. FIG. 23B is an isometric illustration of the embodiment of the wound dressing 900 with a drape or wound cover 906 over the support member and after reduced pressure has been applied to a space 926 between the drape 906 and the wound.

Any embodiments of the dressing 900 and the support member 902 can have any of the features, materials, sizes, shapes, components, or other details of any of the other embodiments disclosed herein, such as without limitation the dressing 100 and support member 102. Additionally, the dressing 900 can have one or more differences as compared to the other dressings disclosed herein. For example, one or more of the arms 914 can have lower section 914a that is formed at a different angle than an upper section 914b of the arms. In some embodiments, the lower portion 914a of each arm can be angled inwardly. Though not required, the lower portion 914a of each arm can be angled such that, when the arms 914 are rotated away from one another, the lower portion 914a of each arm 914 will be approximately perpendicular to the skin or wound surface beneath the lower portion 914a of the arm 914. Additionally, the arms 914 can be staggered from one another along the length of the support member 902 so as to be interdigitated or positioned between the arms 914 positioned on an opposite side of the support member 902. In this arrangement, the arms 914 positioned on one side of the support member 902 will not interfere with the arms 914 positioned on an opposite side of the support member 902 when the sides of the support member 902 are drawn together.

As illustrated, any embodiments of the dressing 900 can have a wound filler 912 positionable beneath a cover member in the wound. In any embodiments disclosed herein, including without limitation the embodiment illustrated in FIGS. 23A and 23B, the wound filler can comprise at least one of foam, gauze, a deflatable hollow member, a sealed enclosure, a sealed enclosure having a collapsible structure therein, and any combination of the foregoing. Additionally, in any embodiments disclosed herein, including the dressing 900, the filler can be a collapsible wound filler configured to be more flexible and, hence, more collapsible, in a lateral direction than in a vertical direction. The support member can be positioned so that the lower portion 914a of each of the arms 914 can be supported by or on the wound filler 912, or can be positioned laterally to the side of the wound filler 912.

Figures 1, 24A:
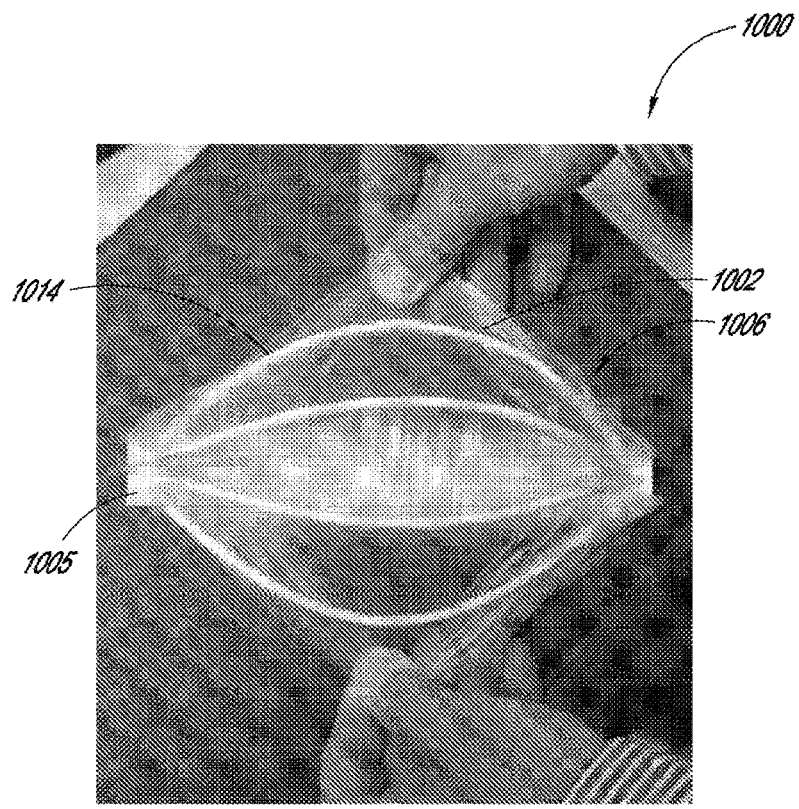
Figures 2, 24A:
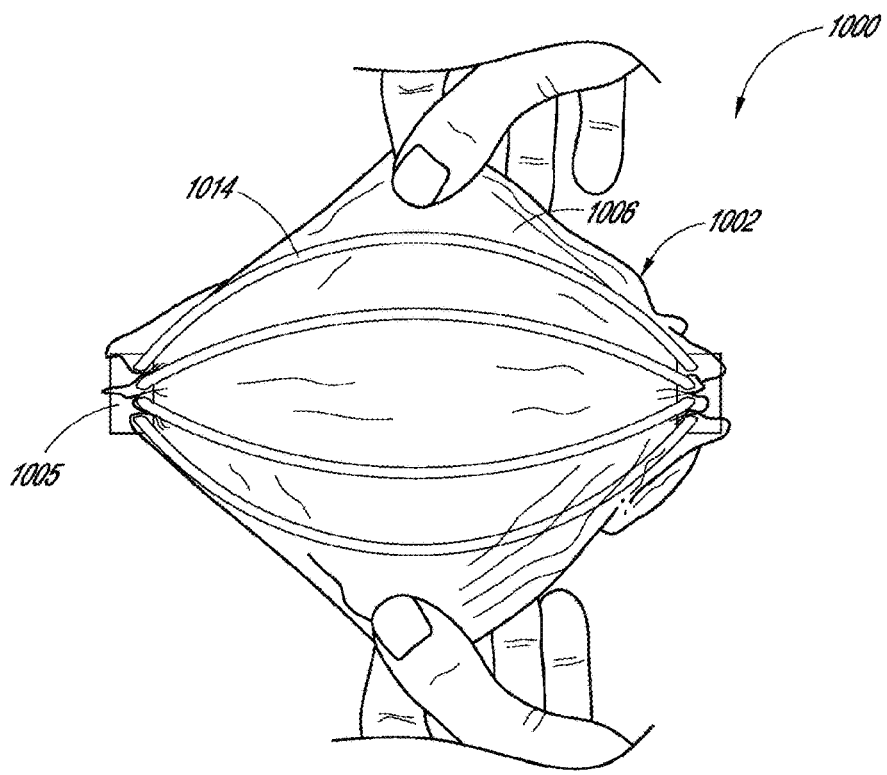
Figures 1, 24B:
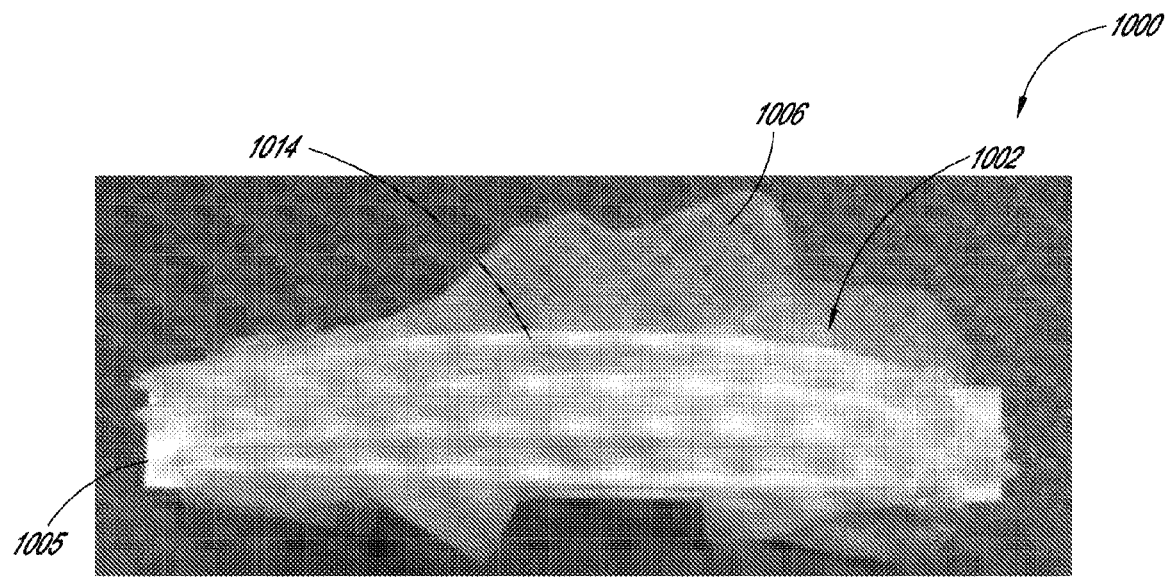
Figures 2, 24B:
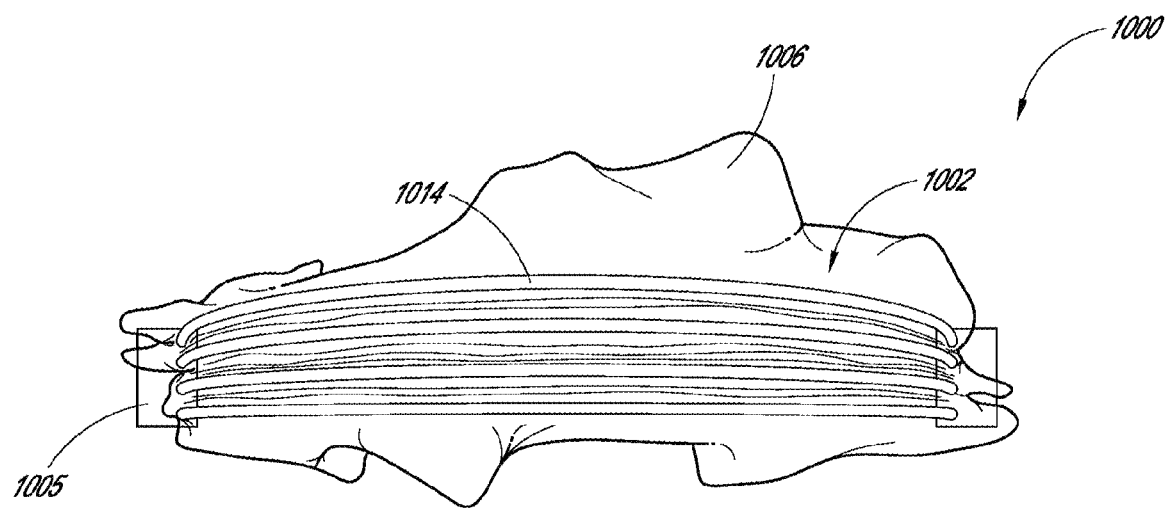

FIG. 24A is an isometric illustration of another embodiment of a wound dressing 1000 having a support member 1002, showing the support member 1002 in a first state (also referred to herein as an expanded state). FIG. 24B is an isometric illustration of the embodiment of the wound dressing 1000 showing the support member 1002 in a second state (also referred to herein as a contracted state). Any embodiments of the dressing 1000 and the support member 1002 can have any of the features, materials, sizes, shapes, components, or other details of any of the other embodiments disclosed herein, such as without limitation the dressing 100 and support member 102.

As with any of the wound embodiments disclosed herein, the arms 1014 of the support member 1002 can support the cover member or dressing 1006 above the wound bed, and can span from one end of the wound to another opposite end of the wound, or can bridge the wound entirely. In some embodiments, the arms 1014 can be arc shaped, triangular shaped, or otherwise. A flat bottom portion 1005 of the support member 1002 can be positioned along the length of the wound and the sides of the drape 1006 can be pulled apart and down against the surface of the skin adjacent to the wound on opposite sides of the wound, thereby expanding the arms 1014 of the support member 1002 apart (opening the arms 1014 in a fan type effect or manner), as shown in FIG. 24A. In some embodiments, the support member 1002 can be configured such that the arms 1014 are biased toward the collapsed position (i.e., as shown in FIG. 24B) wherein the spacing between the arms 1014 is decreased. In this arrangement, when the sides of the drape are pulled apart and taped down to the sides of the wound, as described above, the application of reduced pressure to the space between the drape 1006 and the wound will cause the arms 1014 of the support member 1002 to contract or draw together, thereby exerting a closing force on the sides of the wound that will cause the wound side walls to be drawn together. The support member 1002 can have any number of desired arms, including four arms 1014, from two to four arms 1014, from four to six arms 1014, or more.

Any embodiments of the dressing 1000 can have a wound filler positionable beneath a cover member in the wound. In any embodiments disclosed herein, including without limitation the embodiment illustrated in FIGS. 24A and 24B, the wound filler can comprise at least one of foam, gauze, a deflatable hollow member, a sealed enclosure, a sealed enclosure having a collapsible structure therein, and any combination of the foregoing. Additionally, in any embodiments disclosed herein, including the dressing 1000, the filler can be a collapsible wound filler configured to be more flexible and, hence, more collapsible, in a lateral direction than in a vertical direction.

Figure 25A:
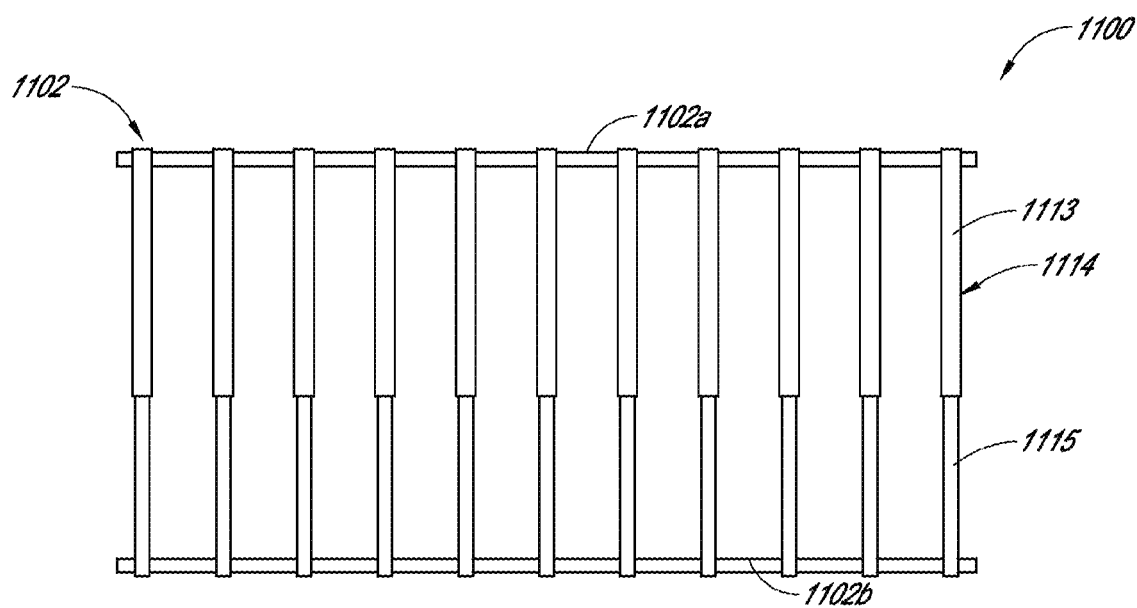
FIG. 25A is a top view of another embodiment of a support member of a wound dressing, showing the support member in a first state (also referred to herein as an expanded state).
Figure 25B:
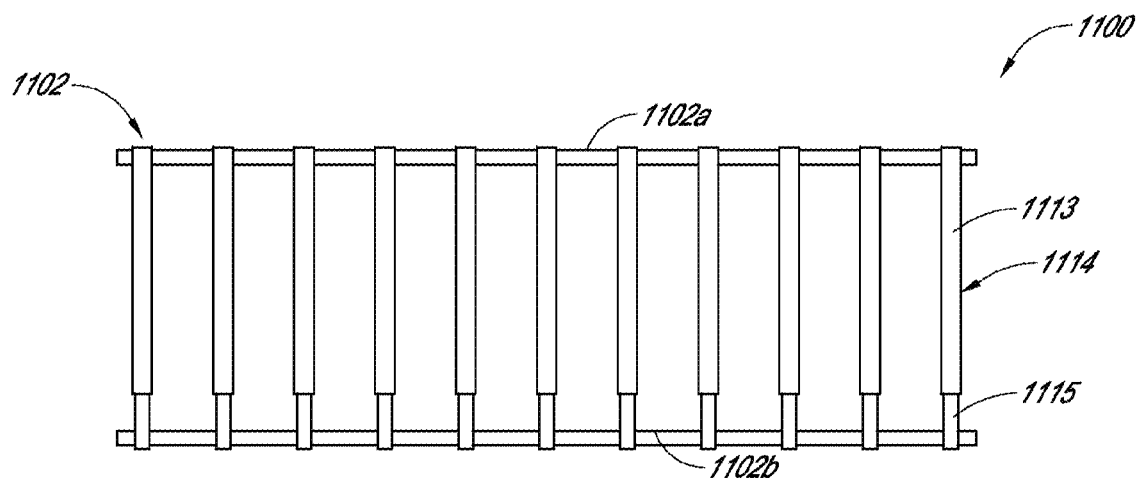
FIG. 25B is a top view of the embodiment of the support member of FIG. 25A, showing the support member in a second state (also referred to herein as a contracted state).

FIG. 25A is an isometric illustration of another embodiment of a wound dressing 1100 having a support member 1102, showing the support member 1102 in a first state (also referred to herein as an expanded state). FIG. 25B is an isometric illustration of the embodiment of the wound dressing 1100 showing the support member 1102 in a second state (also referred to herein as a contracted state). Any embodiments of the dressing 1100 and the support member 1102 can have any of the features, materials, sizes, shapes, components, or other details of any of the other embodiments disclosed herein, such as without limitation the dressing 100 and support member 102 and/or dressing 1000 and support member 1002.

The arms 1114 of the support member 1102 can support a cover member or dressing 1106 (not illustrated) above the wound bed, and can span from one end of the wound to another opposite end of the wound. Some embodiments of the cover can have adhesive along all or a portion of the skin facing surface thereof. Some embodiments of the cover can have adhesive around the perimeter of the cover member, and be adhesive-free in a middle portion of the cover member so that the adhesive does not stick to the support member 1102, which could inhibit the telescoping motion of the support member.

In some embodiments, the arms 1114 can be extendable and contractible, such as in a telescoping fashion. For example, without limitation, the arms 1114 can each have a first or outer arm portion 1113 coupled with or supported by a first side 1102*a* of the support member 1102, and a second or inner arm portion 1115 coupled with or supported by a second side 1102*b* of the support member 1102. In some embodiments, the support member 1102 can be configured such that each arm 1114 of the support member 1102 is independently extendable and contractible relative to adjacent arms 1114 or otherwise. In some embodiments, the support member 1102 can be configured such that the arms 1114 of the support member 1102 are not independently extendable and contractible relative to adjacent arms 1114 or otherwise. The arms 1114 can be made from a lubricious material and/or have a lubricant added thereto to enhance the movement of the telescoping sides of the arms 1114 relative to one another.

The support member 1102 can be expanded (as shown in FIG. 25A) and laid flat over a wound so that a first side 1102*a* of the support member 1102 is positioned on a first side of the wound and a second side 1102*b* is positioned on a second side of the wound, thereby spanning the wound. If desired, though not required, the sides 1102*a*, 1102*b* of the support member 1102 can be affixed or adhered to the healthy skin surrounding the wound using tape, such as OPSITE FLEXIFIX™ or with an adhesive backed cover layer.

In some embodiments, though not required, the support member 1102 can be configured such that the arms 1114 are biased toward the collapsed position (i.e., as shown in FIG. 25B) wherein the spacing between the sides 1102*a*, 1102*b* of the support member 1102 is decreased. In this arrangement, when the sides of the drape are pulled apart and taped down to the sides of the wound, as described above, the application of reduced pressure to the space between the drape 1106 covering the support member 1102 and the wound will cause the sides 1102*a*, 1102*b* of the support member 1102 to collapse or draw together, thereby exerting a closing force on the sides of the wound that will cause the wound side walls to be drawn together. The support member 1102 can have any number of desired arms, including four arms 1114, from two to four arms 1114, from four to six arms 1114, from six to ten arms 1114, or more.

Further, though not illustrated, in some embodiments, the arms 1114 of the support member 1102 can be arc shaped to provide buttressing support to the arms and to prevent the arms 1114 from collapsing into the wound bed. The arms can be telescoping in this arc shaped configuration also, or otherwise be configured to be collapsible and extensible in a lateral direction to permit the support member to contract laterally as the reduced pressure applied to the space between the cover member and the wound cavity causes the sides of the wound to contract laterally.

As in any of the embodiments disclosed herein, the dressing can have a drape or cover member configured to cover the wound positioned above or below the support member (including, without limitation, support member 1102). Additionally, in any of the embodiments disclosed herein, the support member 1102 can be embedded or integrated within the cover member. If the cover member is positioned below the support member, the dressing can be configured such that the support member supports the cover member out of contact with the wound surface or filler member, or at least so as to minimize the contact with the wound surface or filler member. Loops, slots (such as the slots in a tent structure), pockets, cords, threads, or other suitable features can be integrated into or added to any of the cover member embodiments disclosed herein to permit the cover member to be supported by the support member and/or to permit the support member to be integrated into the cover member.

Additionally, in any of the dressing embodiments disclosed herein, including without limitation the dressing embodiment 1100 shown in FIG. 25A, a wound filler 212 is positionable beneath the cover member and/or the support member. In any embodiments disclosed herein, including without limitation the embodiment illustrated in FIG. 25A, the wound filler can comprise at least one of foam, gauze, a deflatable hollow member, a sealed enclosure, a sealed enclosure having a collapsible structure therein, and any combination of the foregoing. Additionally, in any embodiments disclosed herein, including without limitation the dressing 1100, the filler can be a collapsible wound filler configured to be more flexible and, hence, more collapsible, in a lateral direction than in a vertical direction. Additionally, in any of the dressing embodiments disclosed herein, including without limitation the dressing embodiment 1100 shown in FIG. 25A, all or a portion of the support member can be embedded within or integrated with the wound filler and/or the cover member. For example and without limitation, all or any portion of any of the support member embodiments disclosed herein can be attached to, integrated with, or embedded within a foam wound filler. The resulting wound filler can be configured such that the wound filler is more flexible in a lateral direction than in a vertical direction. In this arrangement, application of negative or reduced pressure can cause the filler to collapse in a lateral direction, causing the sides of the wound to collapse or move toward one another. However, the support member can be configured to reduce vertical movement or collapse of the filler. As the wound margins contract or collapse, the telescopic tubes of the support member 1102 can contract along their length, thus permitting the wound walls to contract or move toward one another.

Figure 26A:
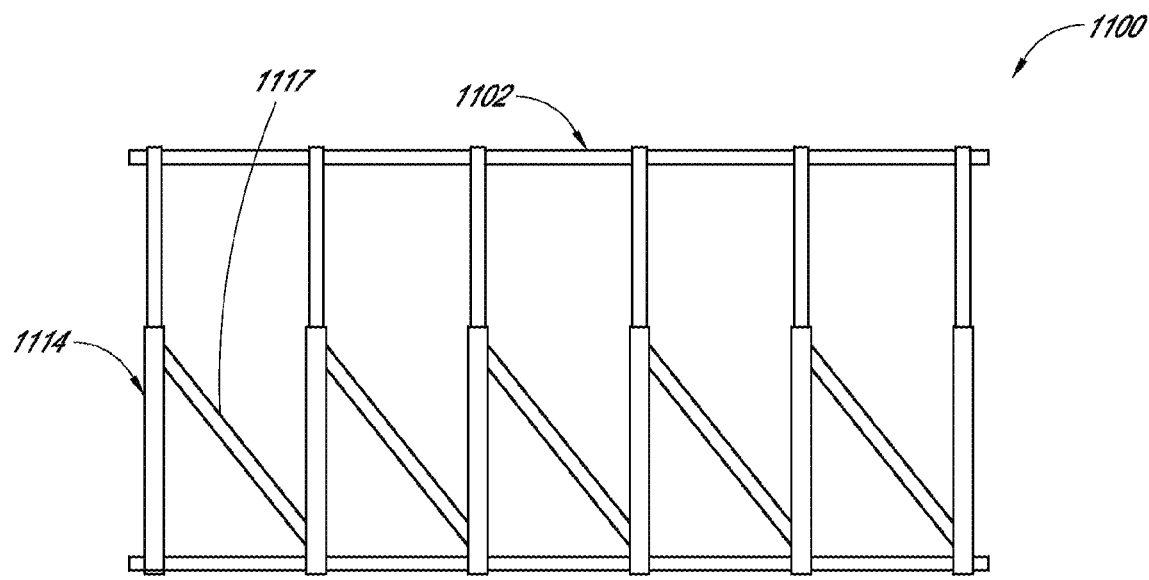
FIG. 26A is a top view of another embodiment of a support member of a wound dressing, showing the support member in a first state (also referred to herein as an expanded state).
Figure 26B:
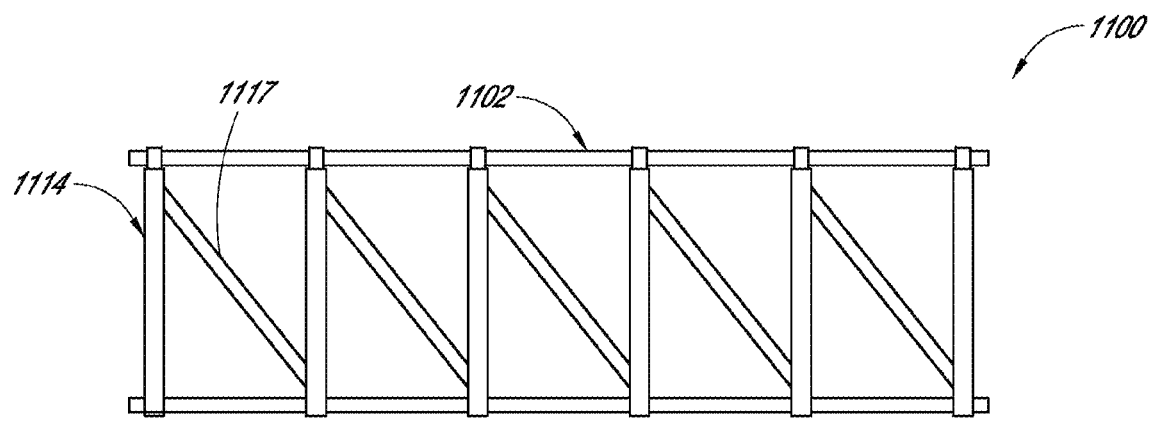
FIG. 26B is a top view of the embodiment of the support member of FIG. 26A, showing the support member in a second state (also referred to herein as a contracted state).

Additionally, in some embodiments, with reference to FIGS. 26A and 26B, the arms 1114 of the support member 1102 can be strengthened or supported along the length thereof. In some embodiments, the support member 1102 can have one or more struts or strengthening members 1117 attached along the length thereof to provide additional strength or stiffness to the arms 1114. The struts or strengthening members 1117 can be diagonally oriented. Any embodiments of the dressing 1100 and the support member 1102 shown in FIGS. 26A and 26B can have any of the features, materials, sizes, shapes, components, or other details of any of the other embodiments disclosed herein, such as without limitation the dressing 100 and support member 102 and/or dressing 1100 and support member 1102 shown in FIGS. 26A and 26B.

Figure 27A:
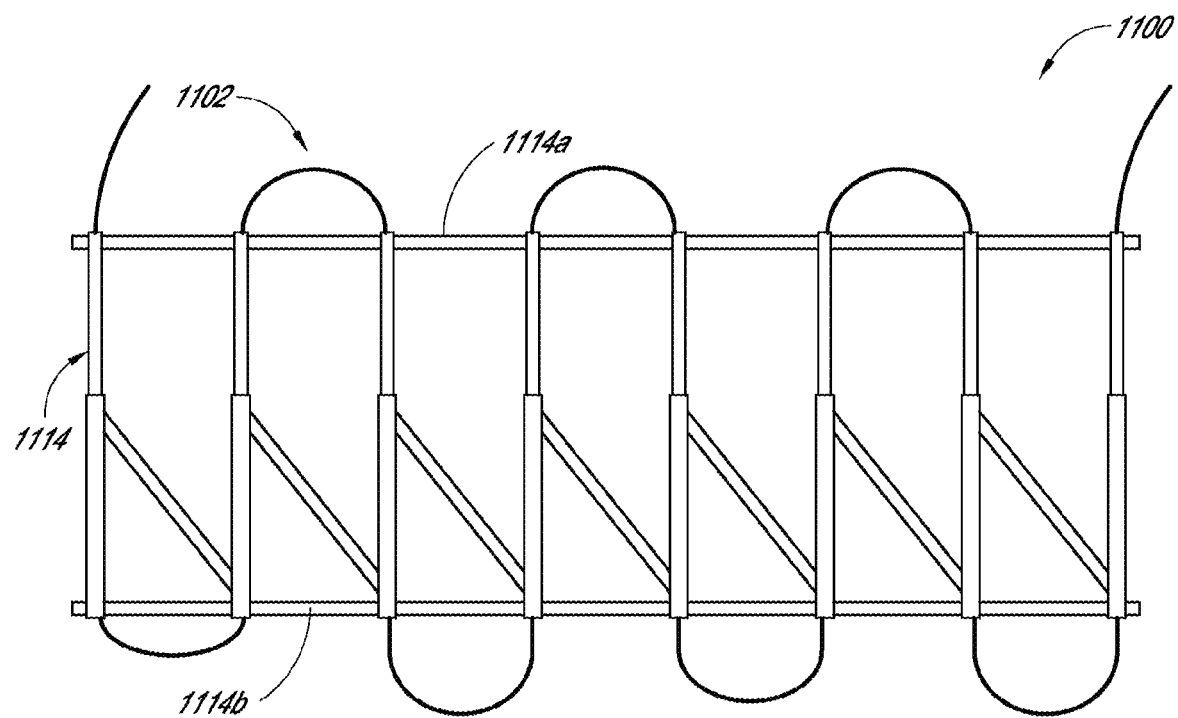
FIG. 27A is a top view of another embodiment of a support member of a wound dressing, showing the support member in a first state (also referred to herein as an expanded state).
Figure 27B:
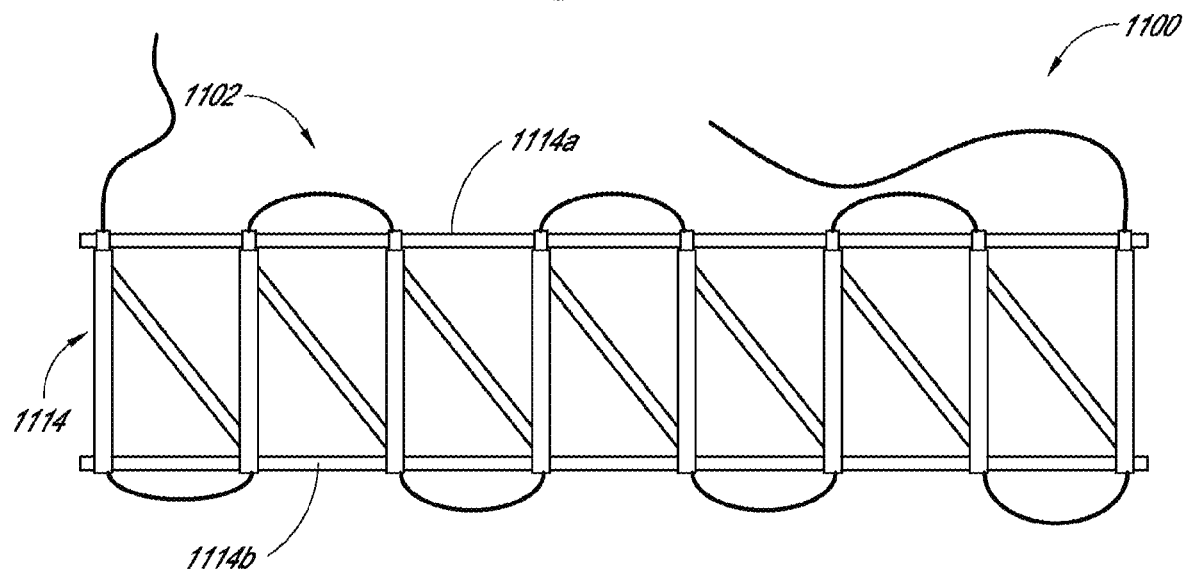
FIG. 27B is a top view of the embodiment of the support member of FIG. 27A, showing the support member in a second state (also referred to herein as a contracted state).

In some embodiments, with reference to FIGS. 27A and 27B, the support member 1102 can be configured to have a tightening mechanism to help draw or pull the sides 1102*a*, 1102*b* of the support member 1102 together. In some embodiments, the support member 1102 can have a drawstring or suture advanced through the arms 1114 of the support member 1102 to help draw or pull the sides 1102*a*, 1102*b* of the support member 1102 together during treatment. For example, the support member 1102 can be configured such that retracting or withdrawing the drawstring from both sides of the support member 1102 can cause the sides of the support member to be drawn together. The drawstring or suture can be advanced through each of the arms 1114 of the support member 1102, through alternating arms 1114 of the support member 1102, or otherwise. The drawstring or suture can be passed through or under the drape (after the drape has been applied over the support member 1102) so as to be accessible to a surgeon, patient, or otherwise during the course of the negative pressure wound treatment so that the sides of the support member 1102 can continue to be drawn together. Additionally, as illustrated, some embodiments of the support member 1102 can have one or more struts or strengthening members 1117 attached along the length thereof to provide additional strength or stiffness to the arms 1114. The struts or strengthening members 1117 can be diagonally oriented. Any embodiments of the dressing 1100 and the support member 1102 shown in FIGS. 26A and 26B can have any of the features, materials, sizes, shapes, components, or other details of any of the other embodiments disclosed herein, such as without limitation the dressing 100 and support member 102 and/or dressing 1100 and support member 1102 shown in FIGS. 26A and 26B.

FIG. 28A is a top view of another embodiment of a support member 1402 of a wound dressing 1400, showing the support member 1402 in a first state (also referred to herein as an expanded state). FIG. 28B is a top view of the embodiment of the support member 1402 of FIG. 28A, showing the support member 1402 in a second state (also referred to herein as a contracted state). Any embodiments of the dressing 1400 and the support member 1402 can have any of the features, materials, sizes, shapes, components, or other details of any of the other embodiments disclosed herein, such as without limitation the dressing 100 and support member 102.

Additionally, the dressing 1400 can have one or more different features, materials, sizes, shapes, components, or other details as compared to the other dressings disclosed herein. For example, one or more of the arms 1414 can have a first arm portion 1415 hingably attached to a second arm portion 1417. In some embodiments, the hinge 1416 can be positioned at approximately the midspan of the arms 1414 and can permit the first and second arm portions 1415, 1417 to rotate relative to one another. Additionally, the first arm portion 1415 can be hingably attached to a first side 1402*a* of the support member 1402 with a second hinge member 1419 and the second arm portion 1417 can be hingably attached to a second side 1402*b* of the support member 1402 with a second hinge member 1421.

The arms 1414 of the support member 1402 can support a cover member or dressing 1406 (not illustrated) above the wound bed, and can span from one end of the wound to another opposite end of the wound. In some embodiments, as mentioned, the arms 1414 can have one or more hinges to allow the arms 1114 to collapse, thereby permitting the sides 1402*a*, 1402*b* of the support member 1402 (and the sides of the wound) to be drawn together, when the support member 1402 is positioned over a wound and the space between the drape (positioned over or under the support member 1402) is subjected to negative pressure.

The support member 1402 can be expanded (as shown in FIG. 28A) and laid flat over a wound so that a first side 1402*a* of the support member 1402 is positioned on a first side of the wound and a second side 1402*b* is positioned on a second side of the wound, thereby spanning the wound. If desired, though not required, the sides 1402*a*, 1402*b* of the support member 1402 can be affixed or adhered to the healthy skin surrounding the wound using tape, such as OPSITE FLEXIFIX™ or with an adhesive backed cover layer.

In some embodiments, though not required, the support member 1402 can be configured such that the arms 1414 are biased toward the collapsed position (i.e., as shown in FIG. 28B) using springs or otherwise. In this arrangement, when the sides of the drape are pulled apart and taped down to the sides of the wound, as described above, the application of reduced pressure to the space between the drape 1406 covering the support member 1402 and the wound will cause the sides 1402*a*, 1402*b* of the support member 1402 to collapse or draw together, thereby exerting a closing force on the sides of the wound that will cause the wound side walls to be drawn together. The support member 1402 can have any number of desired arms, including four arms 1414, from two to four arms 1414, from four to six arms 1414, from six to ten arms 1414, or more.

FIGS. 29A-29B are top views of additional embodiments of wound dressings 1500 having a wound filler member 1512 that can have any of the materials, features, or details of any of the other wound filler embodiments disclosed herein. Further, any embodiments of the dressing 1500 and the support member(s) 1502 can have any of the features, materials, sizes, shapes, components, or other details of any of the other embodiments disclosed herein, such as without limitation the dressing 100 and support member 102 and/or dressing 1000 and support member 1002.

The support members 1514 can provide vertical support or stiffness to the wound filler member 1512 to prevent or inhibit the collapse of the filler member in the vertical direction under the application of reduced pressure, while only minimally inhibiting the lateral contraction of the sides of the wound toward one another (if at all). In other words, the support members 1514 can provide stiffness to the dressing 1500 in a vertical direction (generally perpendicular to the skin surface surrounding the wound) while permitting the wound filler member to be flexible in the lateral direction so that the sides of the wound can contract toward one another (in the direction represented by arrow A1 in FIG. 29A).

The support members 1514 can therefore provide additional support to prevent the cover member or drape 1506 from collapsing vertically into the wound under the application of reduced pressure. The support members 1514 can extend completely across the filler member 1512 (as illustrated in FIG. 29B) or partially across the filler member 1512 (as illustrated in FIG. 29A). Additionally, the support members 1514 can be attached to the filler member 1512 or can be separate from the filler member 1512 and positionable over the filler member 1512 after the filler member has been positioned in a wound. The support members can, in some embodiments, extend beyond the full length of the wound such that the support members rest on a periphery of the wound. Additionally, in some embodiments, the support members 1514 can be integrated or embedded into, or otherwise attached to, the filler member 1512 prior to placement of the filler member 1512 in the wound. In any embodiments disclosed herein, including without limitation the embodiment illustrated in FIG. 29A, the wound filler can comprise at least one of foam, gauze, a deflatable hollow member, a sealed enclosure, a sealed enclosure having a collapsible structure therein, and any combination of the foregoing.

Additionally, in some embodiments, the dressing can have one or more rails generally perpendicularly arranged relative to the support members 1514. The one or more rails can provide a slide surface over which the rails can slide in the direction represented by arrows A1 in FIG. 29. The rails can also be configured to raise the support members 1514 away from the skin surface to minimize or prevent the support members 1514 from irritating or pinching the skin surface.

Further, though not illustrated, in some embodiments, the support members 1514 can be arc shaped or otherwise shaped to have greater resistance to bending along a length of the support members 1514, to inhibit the support members 1514 from flexing or bending into the wound filler 1512. Additionally or alternatively, the support members 1514 can have a changing profile along a length thereof, wherein the support members have the largest area moment of inertia (such as by increasing the vertical height or profile of the support member or members) in a middle portion of the support members so as to provide the greatest amount of bending resistance in a middle portion of the dressing. Thus, in some embodiments, the support members 1514 can have an arc shaped or curved shape in addition to having an increased area moment of inertia in a middle portion of the support members.

Figure 30A:
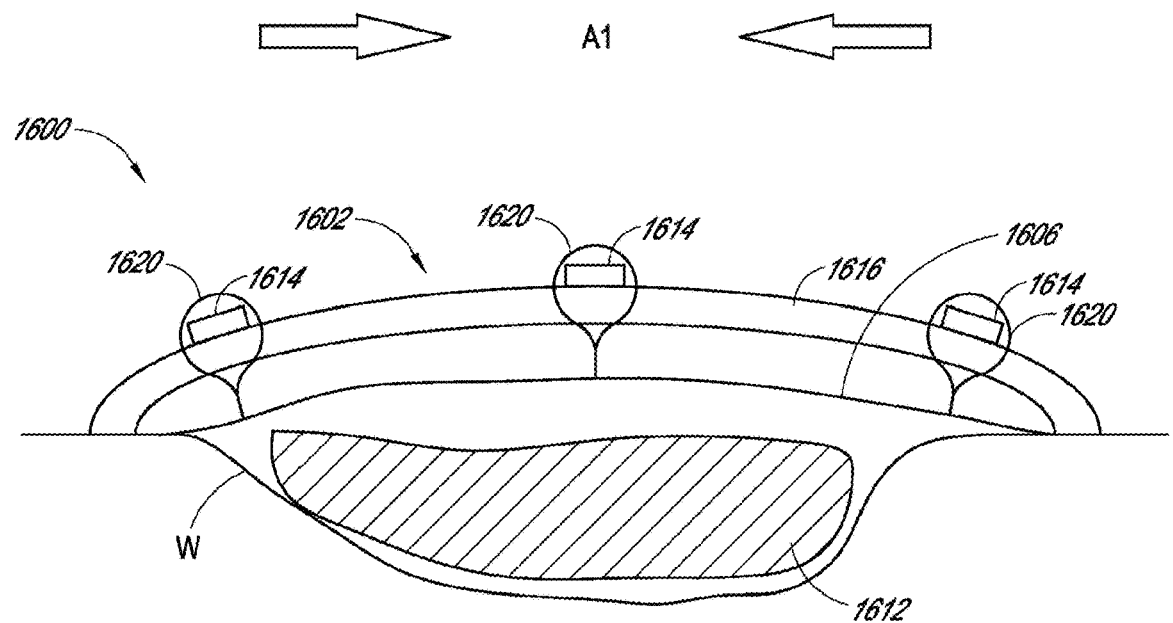
FIG. 30A is a side view of another embodiment of a support member of a wound dressing.
Figure 30B:
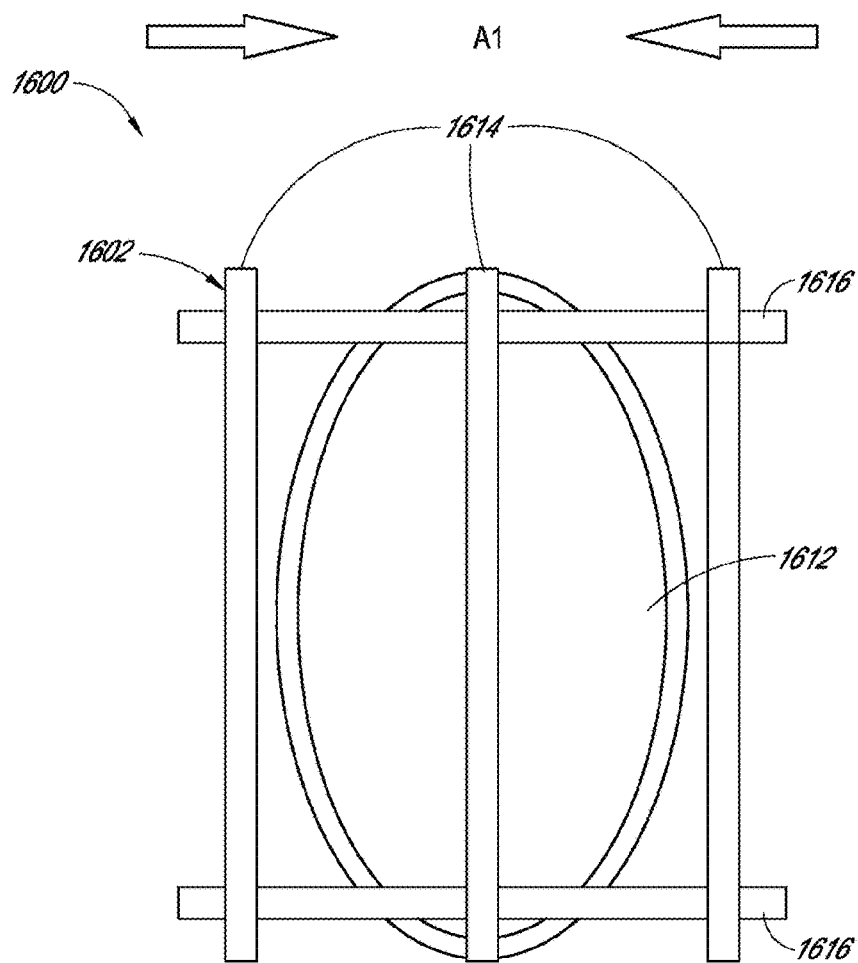
FIG. 30B is a top view of the embodiment of the support member of FIG. 30A.

FIGS. 30A and 30B are a side view and a top view, respectively, of another embodiment of a wound dressing 1600 having a wound filler member 1612 that can have any of the materials, features, or details of any of the other wound filler embodiments disclosed herein. Further, any embodiments of the dressing 1600 and the support member(s) 1602 can have any of the features, materials, sizes, shapes, components, or other details of any of the other embodiments disclosed herein, such as without limitation the dressing 100 and support member 102 and/or dressing 1000 and support member 1002.

The support members 1614 can provide vertical support or stiffness to the dressing 1600 to prevent or inhibit the collapse of the filler member 1612 or the drape 1606 in the vertical direction under the application of reduced pressure, while only minimally inhibiting the lateral contraction of the sides of the wound toward one another (if at all). In other words, the support members 1614 can provide stiffness to the dressing 1600 in a vertical direction (generally perpendicular to the skin surface surrounding the wound) while permitting the wound filler member to be flexible in the lateral direction so that the sides of the wound can contract toward one another (in the direction represented by arrows A1 in FIGS. 30A and 30B). The support members 1614 can be positioned to extend laterally across the wound, extending from one lateral side of the wound to or toward the other.

The support members 1614 can therefore provide additional support to prevent the cover member or drape 1606 from collapsing vertically into the wound under the application of reduced pressure. The support members 1614 can extend completely across the wound or partially across the wound and are positionable over the filler member 1612 and/or over the cover member after the filler member and/or cover member have been positioned in or over the wound. Additionally, in some embodiments, the support members 1614 can be integrated or embedded into, or otherwise attached to, the cover member 1606 prior to placement of the cover member over the wound. For example, in some embodiments, the cover member 1606 can be attached to or supported by the support member using sutures, straps, loops, tape, or any other securing mechanisms 1620 attached to the cover member 1606 and the support member 1602. In any embodiments disclosed herein, the wound filler can comprise at least one of foam, gauze, a deflatable hollow member, a sealed enclosure, a sealed enclosure having a collapsible structure therein, and any combination of the foregoing.

Additionally, in some embodiments, the dressing can have one or more rail members 1616 (also referred to herein as girder or beam members) generally perpendicularly arranged relative to the support members 1614. The one or more rail members 1616 can provide support to the support members to elevate the support members above the skin surface. The support members 1614 can slide in the direction represented by arrows A1 in FIG. 30B relative to the rail members 1616, as the wound contracts in the same direction. The rails can also be configured to raise the support members 1614 away from the skin surface to minimize or prevent the support members 1614 from irritating or pinching the skin surface.

Further, in some embodiments, either or both of the support members 1614 or rail members 1616 can be arc shaped or otherwise shaped to have greater resistance to bending along a length of either or both of the support members 1614 or rail members 1616, to inhibit the support members 1614 and/or rail members 1616 from flexing or bending into the wound filler 1612. Additionally or alternatively, either or both of the support members 1614 or rail members 1616 (of which there can be more than two in any embodiments) can have a changing profile along a length thereof, having the largest area moment of inertia (such as by increasing the vertical height or profile of one or more of the support member or members or rail member or members) in a middle portion of the support members and/or rail members so as to provide the greatest amount of bending resistance in a middle portion of the dressing. Thus, in some embodiments, the support members 1614 and/or rail members 1616 can have an arc shaped or curved shape in addition to having an increased area moment of inertia in a middle portion of the support members and/or rail members. The support members 1614 can be configured to slide laterally relative to the rail members 1616 to allow the support members to slide as the walls of the wound contract.

The support members and rail members in each dressing kit or embodiment can have a variety of lengths, depending on the shape of the wound, position of the support member, shape and profile of the wound filler, etc. Additionally, the number and position of the support members can vary. In some embodiments, there can be from 3 to 10 support members positioned over a wound, in any of a variety of positions and having a variety of lengths and shapes.

Some embodiments of the cover can have adhesive along all or a portion of the skin facing surface thereof. Some embodiments of the cover can have adhesive around the perimeter of the cover member, and be adhesive-free in a middle portion of the cover member so that the adhesive does not stick to the support members 1614. Additionally, in some embodiments, the support members 1614 and/or rail members 1616 can be positioned, embedded, or integrated within or attached or adhered to the cover member 1606. Further, as with any of the dressing embodiments disclosed herein, the support members 1614 can be configured to be positioned over and above at least a portion of the cover member such that the cover member is attached or tethered to the support members 1614. If the cover member is positioned below the support member, the dressing can be configured such that the support member supports the cover member out of contact with the wound surface or filler member, or at least so as to minimize the contact with the wound surface or filler member. Loops, slots (such as the slots in a tent structure), pockets, cords, threads, or other suitable features can be integrated into or added to any of the cover member embodiments disclosed herein to permit the cover member to be supported by the support member and/or to permit the support member to be integrated into the cover member.

In any embodiments disclosed herein, the support member can have one or more tissue anchors, fixation mesh, tissue connectors, and/or other tissue engaging elements configured to engage one or more of the tissue layers adjacent to the legs of the support member. For example, in some embodiments, a plurality of tissue anchors can be supported by the legs, panels, the inflatable bladder or filler positioned in the wound, or any other component or feature of the support member or dressing member disclosed herein.

In some embodiments, one or more tissue anchors, mesh, or other tissue engaging elements can be tethered to the legs, panels, the inflatable bladder or filler positioned in the wound, or any other component or feature of the support member or dressing member disclosed herein. The tissue anchors can be tethered to the legs, panels, the inflatable bladder or filler positioned in the wound, or any other component or feature of the support member or dressing member disclosed herein using sutures, clips, strands, tape, or other tethering mechanisms.

Examples of attachment mechanisms for engaging tissue include adhesive, grippers or barbs, Velcro, hooks of Velcro, mushroom shaped hooks of Velcro, or other attachment mechanism known in the art.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A method of closing a wound, comprising:
   placing a support member over a wound, the support member comprising a plurality of first side supports and a plurality of second side supports, the first side supports and second side supports coupled with an elongate member extending a distance generally parallel to the wound, the elongate member comprising a longitudinal axis, the first side supports and the second side supports configured to rotate about the longitudinal axis;
   fluidically connecting the wound to a source of negative pressure;
   applying negative pressure to the wound via the source of negative pressure; and
   wherein the negative pressure is applied to a space under a cover layer positioned over the support member, the cover layer comprising a port.

2. The method of claim 1, wherein the cover layer is adhered to the skin surrounding the wound.

3. The method of claim 1, wherein the cover layer is a fluid impermeable drape.

4. The method of claim 1, further comprising positioning a porous member between the cover layer and the support member.

5. The method of claim 4, wherein the porous member is a foam.

6. The method of claim 1, further comprising positioning a porous member beneath the support member.

7. The method of claim 1, wherein the source of negative pressure comprises a vacuum pump.

8. The method of claim 1, wherein the first side support is configured to rotate around the elongate member.

9. The method of claim 8, wherein the second side support is configured to rotate around the elongate member.

10. The method of claim 9, wherein the first side support and the second side support are configured to rotate about the same axis of rotation.

11. The method of claim 9, wherein the first side support and the second side support are configured to rotate independently.

12. The method of claim 1, wherein the first side support and the second side support branch from the elongate member.

13. The method of claim 1, wherein the support member comprises a cross-support coupled to the first side support and the second side support.

14. The method of claim 1, wherein the port is fluidically connected to a conduit.

15. The method of claim 1, wherein the first side support and the second side support are configured to rotate in response to the application of negative pressure.

16. A method of closing a wound, comprising:
   placing a support member over a wound, the support member comprising a plurality of first side supports and a plurality of second side supports, the first side supports and second side supports coupled with an elongate member extending a distance generally parallel to the wound, the elongate member comprising a longitudinal axis, the first side supports and the second side supports configured to rotate about the longitudinal axis;

fluidically connecting the wound to a source of negative pressure;

applying negative pressure to the wound via the source of negative pressure; and wherein the negative pressure is applied to a space under a cover layer positioned over the support member, the cover layer adhered to the skin surrounding the wound.

17. A method of closing a wound, comprising:

placing a support member over a wound, the support member comprising a plurality of first side supports and a plurality of second side supports, the first side supports and second side supports coupled with an elongate member extending a distance generally parallel to the wound, the elongate member comprising a longitudinal axis, the first side supports and the second side supports configured to rotate about the longitudinal axis in response to the application of negative pressure;

fluidically connecting the wound to a source of negative pressure;

applying negative pressure to the wound via the source of negative pressure; and wherein the negative pressure is applied to a space under a cover layer positioned over the support member.

* * * * *